(12) United States Patent
Choi et al.

(10) Patent No.: US 6,204,040 B1
(45) Date of Patent: Mar. 20, 2001

(54) GLUCONOBACTER SUBOXYDANS SORBITOL DEHYDROGENASE, GENES AND METHODS OF USE THEREOF

(75) Inventors: Eui-Sung Choi, Taejon; Sang-Ki Rhee, Seoul; Eun-Hae Lee, Taejon, all of (KR)

(73) Assignees: Korea Research Institute of Bioscience and Biotechnology, Taejon (KR); Archer-Daniels-Midland Company, Decatur, IL (US)

( * ) Notice: Subject to any disclaimer, the term of this patent is extended or adjusted under 35 U.S.C. 154(b) by 0 days.

(21) Appl. No.: 09/296,284

(22) Filed: Apr. 22, 1999

(51) Int. Cl.$^7$ ........................................ C12N 9/04
(52) U.S. Cl. .................. 435/190; 435/72; 435/320.1; 435/252.3; 435/254.11; 435/419; 435/254.2; 536/23.2
(58) Field of Search .................. 536/23.2; 435/320.1, 435/252.3, 254.11, 419, 254.2, 190, 72

(56) References Cited

U.S. PATENT DOCUMENTS

| | | | |
|---|---|---|---|
| 4,935,359 | 6/1990 | Yin et al. | 435/138 |
| 4,960,695 | 10/1990 | Hoshino et al. | 435/42 |
| 5,312,741 | 5/1994 | Hoshino et al. | 435/42 |
| 5,541,108 | 7/1996 | Fujiwara et al. | 435/252.1 |
| 5,747,301 | 5/1998 | Hoshino et al. | 435/105 |
| 5,753,481 | 5/1998 | Niwa et al. | 435/190 |
| 5,834,263 | 11/1998 | Niwa et al. | 435/138 |
| 5,861,292 | 1/1999 | Niwa et al. | 435/190 |
| 5,888,786 | 3/1999 | Niwa et al. | 435/138 |

FOREIGN PATENT DOCUMENTS 0 897 984 A2  2/1999  (EP).
98-069057   10/1998  (KR).

OTHER PUBLICATIONS

GenBank Accession No. E03223 (Jun. 1997).*
GenBank Accession No. E04355 (Jun. 1997).*
GenBank Accession No. AC005387 (Aug. 1998).*
GenBank Accession No. D86375 (Apr. 1997).*
Choi, E.–S. et al. "Purification of a membrane–bound sorbitol dehydrogenase from *Gluoconobacter suboxydans,*" *FEMS Microbiol. Letts.* 125:45–50 (1995).
Shinagawa, E. et al. "Purification and Characterization of D–Sorbitol Dehydrogenase from Membrane of *Gluconobacter suboxydans* ver α," *Agric. Biol. Chem.* 46:135–141 (1982).
Kondo, K. and S. Horinouchi, "Characterization of the Genes Encoding the Three–Component Membrane–Bound Alcohol Dehydrogenase from *Gluconobacter suboxydans* and Their Expression in *Acetobacter pasteurianus,*" *Appl. Environ. Microbiol.* 63:1131–1138 (Mar. 1997).
International Search Report for International Application No. PCT/IB99/00736, mailed Feb. 18, 2000.

* cited by examiner

*Primary Examiner*—Ponnathapu Achutamurthy
(74) *Attorney, Agent, or Firm*—Sterne, Kessler, Goldstein & Fox P.L.L.C.

(57) ABSTRACT

The invention relates to the fields of molecular biology, bacteriology and industrial fermentation. More specifically, the invention provides isolated nucleic acid molecules encoding the three subunits of a novel, membrane-bound, Gluconobacter oxydans sorbitol dehydrogenase (SDH) of the invention and vectors and host cells containing said isolated nucleic acid molecules. The invention further provides isolated polypeptides for the three subunits of the SDH enzyme of the invention, and processes for the production of L-sorbose and 2 keto-L-gulonic acid.

29 Claims, 19 Drawing Sheets

```
         10         20         30         40         50         60
CGAGAACGGAAGCCCGCTGAAATCGACCCGTTCCCCATCAAAATACTTTTCGAGAAGATC 70         80         90        100        110        120
ACGAACCTTCACCAGGAGCGGCGTCTCTTCCTGATCGCGCCCCACCCCCAATCGAGAGC 130        140        150        160        170        180
AACAATACGCCCGTCATCTTCACTGATGGTCAGGGCTCCGAGATGGGAATGGCAGGAAAG 190        200        210        220        230        240
CTGTGGCATACAGATACGCTGCCCCATCCCCCGGAAAGCGTCAATCATGCTTCCCTAAAA 250        260        270        280        290        300
GAGTCCCTGAGAAAAAAATACATGCGTGTCACGCATATGCAGGGAGGCCGGTATTCTCAA 310        320        330        340        350        360
ATAACATATGGGATCATTTTTGTATGATTTCATGAAATATTACGCACTTTGTTGAGAAAC 370        380        390        400        410        420
TGCCATTTTTTGTGTCAAACCTGCGACAGACACTAAAGCTGTTTTGGTTGTTTGGTTATT 430        440        450        460        470        480
AAGAATAATTCTCATGTAATTAAGCGAGCGATTTTACGCGGATAGTGCTCACGGAGACGT 490        500        510        520        530        540
CAGAAGCCCACGTTTCCGACAAACAATAAAATAAGCGAGTAGTAAGTTCACGCGATGCTA 550        560        570        580        590        600
CGTTTTCCAGACGACTTGGAGAAACTGAGGAGCACCTAGGCACCCACAGAGGCGCCTATC 610        620        630        640        650        660
AGGACTTGGATTACGTCTGAATACCATTAACAGGAACAGTCTTTGCAAAA AGGA CAGTCG 670        680        690        700        710        720
GATCATGGTTTCTGGTCTACTGACGCCGATCAACGTTACGAAGAAGCGCCTTCTGGGTTG
     M  V  S  G  L  L  T  P  I  N  V  T  K  K  R  L  L  G  C 730        740        750        760      ▼ 770        780
CGCTGCTGCTCTGGCATTCTGCGCCACCTCTCCTGTCGCCCTGGCTGAGGACACAGGAAC
 A  A  A  L  A  F  C  A  T  S  P  V  A  L  A  E  D  T  G  T
```

FIG. 8A

```
       790       800       810       820       830       840
AGCCATTACAAACGCCGACCAGCATCCGGGTGACTGGATGAGCTATGGCCGGACCTATTC
 A  I  T  N  A  D  Q  H  P  G  D  W  M  S  Y  G  R  T  Y  S 850       860       870       880       890       900
CGAGCAGCGCTACAGCCCGCTGGATCAGATCACCAAGGACAATGCGAGCAATCTGAAGCT
 E  Q  R  Y  S  P  L  D  Q  I  T  K  D  N  A  S  N  L  K  L 910       920       930       940       950       960
GGCATGGCACTACGATCTGGATACCAACCGTGGTCAGGAAGGTACGCCGCTGATCGTTGA
 A  W  H  Y  D  L  D  T  N  R  G  Q  E  G  T  P  L  I  V  D 970       980       990      1000      1010      1020
TGGCGTCATGTACGCCACCACAAACTGGAGCAAGATGAAGGCTCTGGATGCAGCTACGGG
 G  V  M  Y  A  T  T  N  W  S  K  M  K  A  L  D  A  A  T  G 1030      1040      1050      1060      1070      1080
CAAGCTGCTGTGGTCTTACGATCCAAAGGTTCCAGGCAACATCGCCGACCGCGGCTGCTG
 K  L  L  W  S  Y  D  P  K  V  P  G  N  I  A  D  R  G  C  C 1090      1100      1110      1120      1130      1140
CGATACGGTCAACCGTGGTGCAGCCTACTGGAACGGCAAAGTCTATTTCGGCACCTTCGA
 D  T  V  N  R  G  A  A  Y  W  N  G  K  V  Y  F  G  T  F  D 1150      1160      1170      1180      1190      1200
CGGTCGCCTGATTGCCCTGGATGCCAAGACCGGCAAGCTGGTCTGGAGCGTCTATACGGT
 G  R  L  I  A  L  D  A  K  T  G  K  L  V  W  S  V  Y  T  V 1210      1220      1230      1240      1250      1260
TCCCAAGGAAGCGCAGCTGGGTCACCAGCGCTCCTACACGGTTGACGGTGCTCCCCGTAT
 P  K  E  A  Q  L  G  H  Q  R  S  Y  T  V  D  G  A  P  R  I 1270      1280      1290      1300      1310      1320
CGCCAAGGGCAAGGTCATCATCGGCAACGGCGGTGCAGAGTTCGGCGCCCGTGGCTTCGT
 A  K  G  K  V  I  I  G  N  G  G  A  E  F  G  A  R  G  F  V 1330      1340      1350      1360      1370      1380
GACGGCGTATGACGCTGAAACGGGAAAGATGGACTGGCGCTTCTTCACCGTTCCGAACCC
 T  A  Y  D  A  E  T  G  K  M  D  W  R  F  F  T  V  P  N  P 1390      1400      1410      1420      1430      1440
TGACAACAAGCCGGACGGCGCAGCGTCTGACGACGTGCTGATGTCCAAGGCTTATCCGAC
 D  N  K  P  D  G  A  A  S  D  D  V  L  M  S  K  A  Y  P  T 1450      1460      1470      1480      1490      1500
ATGGGGCAAGGGCGGCGCGTGGAAGCAGCAGGGCGGTGGCGGTACCGTCTGGGATTCGCT
 W  G  K  G  G  A  W  K  Q  Q  G  G  G  T  V  W  D  S  L 1510      1520      1530      1540      1550      1560
GATCTATGACCCTGTAACGGATCTCGTCTATCTGGGCGTCGGTAACGGCTCGCCATGGAA
 I  Y  D  P  V  T  D  L  V  Y  L  G  V  G  N  G  S  P  W  N
```

FIG. 8B

```
      1570        1580        1590        1600        1610        1620
CTACAAGTTCCGTTCTGAAGGAAAAGGCAACAACCTCTTCCTCGGCAGCATCGTGGCCAT
 Y  K  F  R  S  E  G  K  G  N  N  L  F  L  G  S  I  V  A  I 1630        1640        1650        1660        1670        1680
CAATCCTGACACCGGCAAATACGTCTGGCATTTCCAGGAAACGCCAATGGACCAGTGGGA
 N  P  D  T  G  K  Y  V  W  H  F  Q  E  T  P  M  D  Q  W  D 1690        1700        1710        1720        1730        1740
TTATACCTCGGTTCAGCAGATCATGGCCCTCGACATGCCGGTCAATGGCGAAATGCGCCA
 Y  T  S  V  Q  Q  I  M  A  L  D  M  P  V  N  G  E  M  R  H 1750        1760        1770        1780        1790        1800
TGTGCTCGTGCATGCGCCGAAGAACGGCTTCTTCTATATCATTGATGCCAAGACCGGTAA
 V  L  V  H  A  P  K  N  G  F  F  Y  I  I  D  A  K  T  G  K 1810        1820        1830        1840        1850        1860
GTTCATCTCCGGCAAGCCGTACACCTACGAGAACTGGGCCAATGGCCTCGATCCGGTAAC
 F  I  S  G  K  P  Y  T  Y  E  N  W  A  N  G  L  D  P  V  T 1870        1880        1890        1900        1910        1920
GGGTCGTCCGAACTACAATCCAGATGCTCTCTGGACGCTGAACGGCAAGCCCTGGTACGG
 G  R  P  N  Y  N  P  D  A  L  W  T  L  N  G  K  P  W  Y  G 1930        1940        1950        1960        1970        1980
CATCCCCGGCGATCTGGGTGGTCATAACTTCGCTGCCATGGCTTACAGCCCACAGACGAA
 I  P  G  D  L  G  G  H  N  F  A  A  M  A  Y  S  P  Q  T  K 1990        2000        2010        2020        2030        2040
GCTGGTTTACATTCCCGCCCAGCAGGTTCCCTTCGTTTACGATCCGCAGAAGGGTGGCTT
 L  V  Y  I  P  A  Q  Q  V  P  F  V  Y  D  P  Q  K  G  G  F 2050        2060        2070        2080        2090        2100
CAAGGCTCACCACGACAGCTGGAACCTTGGCCTCGACATGAACAAGATCGGCCTGCTTGA
 K  A  H  H  D  S  W  N  L  G  L  D  M  N  K  I  G  L  L  D 2110        2120        2130        2140        2150        2160
TGACAACGATCCACAGCACAAGGCTGACAAGGCCCAGTTCCTGAAGGATCTGAAGGGCTG
 D  N  D  P  Q  H  K  A  D  K  A  Q  F  L  K  D  L  K  G  W 2170        2180        2190        2200        2210        2220
GATCGTTGCATGGGATCCGCAGAAGCAGCAGGCAGCCTTCACGGTTGACCACAAGGGTCC
 I  V  A  W  D  P  Q  K  Q  Q  A  A  F  T  V  D  H  K  G  P 2230        2240        2250        2260        2270        2280
GTGGAATGGCGGTCTTCTGGCAACGGCTGGTGGCGTTCTGTTCCAGGGTCTCGCCAACGG
 W  N  G  G  L  L  A  T  A  G  G  V  L  F  Q  G  L  A  N  G 2290        2300        2310        2320        2330        2340
TGAGTTCCACGCCTACGACGCGACGACGGGTAAGGATCTCTTCACCTTCCCAGCACAGAG
 E  F  H  A  Y  D  A  T  T  G  K  D  L  F  T  F  P  A  Q  S
```

FIG. 8C

```
        2350      2360      2370      2380      2390      2400
CGCCATCATTGCCCCGCCAGTCACCTACACAGCCAACGGCAAGCAGTATGTTGCGGTTGA
  A  I  I  A  P  P  V  T  Y  T  A  N  G  K  Q  Y  V  A  V  E 2410      2420      2430      2440      2450      2460
AGTGGGCTGGGGCGGTATCTATCCGTTCTTCCTGGGCGGCGTAGCCCGTACGTCCGGCTG
  V  G  W  G  G  I  Y  P  F  F  L  G  G  V  A  R  T  S  G  W 2470      2480      2490      2500      2510      2520
GACCGTCAACCACTCCCGGATCATCGCGTTCGCTCTGGACGGCAACGACAAGCTGCCAGC
  T  V  N  H  S  R  I  I  A  F  A  L  D  G  N  D  K  L  P  A 2530      2540      2550      2560      2570      2580
CAAGAACGAGCTCGGCTTCGTTCCAGTGAAGCCGCCTGAGAAATGGGATGAAGCCAAGAT
  K  N  E  L  G  F  V  P  V  K  P  P  E  K  W  D  E  A  K  I 2590      2600      2610      2620      2630      2640
CAAGGACGGCTACTTCCAGTTCCAGACCTATTGCGCAGCCTGCCATGGTGACAACGGTAT
  K  D  G  Y  F  Q  F  Q  T  Y  C  A  A  C  H  G  D  N  G  I 2650      2660      2670      2680      2690      2700
CTCCGGCGGTGTTCTGCCAGACCTGCGCTGGTCCGGTGCGATCCGTGGAGAGGAGAAGTT
  S  G  G  V  L  P  D  L  R  W  S  G  A  I  R  G  E  E  K  F 2710      2720      2730      2740      2750      2760
CTACAAGCTCGTCGGCAAGGGTGCTCTAACGGCCTACGGTATGGACCGTTTCGACACGTC
  Y  K  L  V  G  K  G  A  L  T  A  Y  G  M  D  R  F  D  T  S 2770      2780      2790      2800      2810      2820
CATGTCGCCAGCTGAAATCGAAGACATCCGCAACTTCCTTGTGAAGCGCGCCAACGAGTC
  M  S  P  A  E  I  E  D  I  R  N  F  L  V  K  R  A  N  E  S 2830      2840      2850      2860      2870      2880
CTACGCAGACGAAGTCAAGGCCCGAAAGAATGAGGCAGGCGTCCCTAACGGCGAATTCCT
  Y  A  D  E  V  K  A  R  K  N  E  A  G  V  P  N  G  E  F  L 2890      2900      2910      2920      2930      2940
CAACGTCCCTCAGGGTTCGGTTGCGCCTGCAACGCCGGACCATCCGTAACGGGAAACCGT
  N  V  P  Q  G  S  V  A  P  A  T  P  D  H  P  *

2950      2960      2970      2980      2990      3000
CACGCTGAAAGGAATGACGTGACATGCTCAAGGCATTAACTCGGGACAGACTGGTATCTG
                      M  L  K  A  L  T  R  D  R  L  V  S  E 3010      3020      3030      3040      3050      3060
AGATGAAACAGGGATGGAAATACGCGGCCGCAGTCGGCCTCATGGCAGTGTCTTTCGGTG
  M  K  Q  G  W  K  Y  A  A  A  V  G  L  M  A  V  S  F  G  A

3070▼     3080      3090      3100      3110      3120
CTGCCCAAGCCCAGGACGCTGATGACGCCCTGATTCAGCGCGGTGCCTACGTGGCCCGCC
  A  Q  A  Q  D  A  D  D  A  L  I  Q  R  G  A  Y  V  A  R  L
```

FIG. 8D

```
       3130      3140      3150      3160      3170      3180
TGTCTGACTGCGTTGCCTGCCATACCGCACTACACGGCCAGCCTTTTGCTGGTGGTCTGG
  S   D   C   V   A   C   H   T   A   L   H   G   Q   P   F   A   G   G   L   E 3190      3200      3210      3220      3230      3240
AGATCAAGAGCCCGATCGGCACGATCTACTCCACCAACATCACGCCTGACCCGAAATACG
  I   K   S   P   I   G   T   I   Y   S   T   N   I   T   P   D   P   K   Y   G 3250      3260      3270      3280      3290      3300
GTATCGGCAACTATACACTCGAAGATTTCACGAAGGCGATCCGTAAGGGTATCCGCAAGG
  I   G   N   Y   T   L   E   D   F   T   K   A   I   R   K   G   I   R   K   D 3310      3320      3330      3340      3350      3360
ACGGCGCGACGGTTTATCCGGCCATGCCGTATCCTGAGTTCGCTCGCCTGTCTGATGACG
  G   A   T   V   Y   P   A   M   P   Y   P   E   F   A   R   L   S   D   D   D 3370      3380      3390      3400      3410      3420
ACATCAAGGCCATGTATGCCTTCTTCATGCATGGCGTGAAGCCGGTCGCCCTTCAGAACA
  I   K   A   M   Y   A   F   F   M   H   G   V   K   P   V   A   L   Q   N   K 3430      3440      3450      3460      3470      3480
AGCAGCCGGACATCTCCTGGCCGATGAACATGCGCTGGCCGTTGGCCATCTGGCGCGCGA
  Q   P   D   I   S   W   P   M   N   M   R   W   P   L   A   I   W   R   A   M 3490      3500      3510      3520      3530      3540
TGTTTGTTCCGACTGTCACACCAGGCCTCGACAAGAGCATCTCCGATCCGGAAGTGGCGC
  F   V   P   T   V   T   P   G   L   D   K   S   I   S   D   P   E   V   A   R 3550      3560      3570      3580      3590      3600
GTGGCGAATACCTCGTGAATGGCCCAGGCCATTGTGGCGAGTGTCATACGCCCCGTGGCA
  G   E   Y   L   V   N   G   P   G   H   C   G   E   C   H   T   P   R   G   M 3610      3620      3630      3640      3650      3660
TGGCCATGCAGGTCAAGGGCTATACGGCCAAGGACGGCAACGCTTACCTCTCCGGTGGCG
  A   M   Q   V   K   G   Y   T   A   K   D   G   N   A   Y   L   S   G   G   A 3670      3680      3690      3700      3710      3720
CACCGATCGACAACTGGATTGCTCCCAGCCTGCGTAGCAATAGCGACACGGGTCTGGGTC
  P   I   D   N   W   I   A   P   S   L   R   S   N   S   D   T   G   L   G   R 3730      3740      3750      3760      3770      3780
GCTGGTCTGAAGACGACATTGCCGAGTTCCTGAAGAGCGGCCGTATCGACCATTCTGCCG
  W   S   E   D   D   I   A   E   F   L   K   S   G   R   I   D   H   S   A   V 3790      3800      3810      3820      3830      3840
TCTTCGGTGGCATGGCTGACGTGGTGGCCTACAGCACCCAGCACTGGACCGACGACGATC
  F   G   G   M   A   D   V   V   A   Y   S   T   Q   H   W   T   D   D   D   L 3850      3860      3870      3880      3890      3900
TGCACGCAACGGCCAAGTACCTGAAGAGCATGCCGGCCGTTCCGGAAGGCAAAAACCTGG
  H   A   T   A   K   Y   L   K   S   M   P   A   V   P   E   G   K   N   L   G
```

FIG. 8E

```
      3910      3920      3930      3940      3950      3960
GTCAGGATGACGGCAAGGCCACGGCCCTGCTCGAAGCCGGTGGCAAGGGTGATGCAGGCG
  Q  D  D  G  K  A  T  A  L  L  E  A  G  G  K  G  D  A  G  A 3970      3980      3990      4000      4010      4020
CAGAGGTTTACCTCCACAACTGTGCCATCTGCCATATGAACGATGGCACTGGTGTCAACC
  E  V  Y  L  H  N  C  A  I  C  H  M  N  D  G  T  G  V  N  R 4030      4040      4050      4060      4070      4080
GCATGTTCCCGCCGCTGGCTGGCAACCCGGTCGTCATCACGGACAATGCAACCTCAATGG
  M  F  P  P  L  A  G  N  P  V  V  I  T  D  N  A  T  S  M  A 4090      4100      4110      4120      4130      4140
CCAACATCGTGACATTCGGCGGTATTCTGCCTCCGACGAATACGGCGCCATCTGCTGTTG
  N  I  V  T  F  G  G  I  L  P  P  T  N  T  A  P  S  A  V  A 4150      4160      4170      4180      4190      4200
CCATGCCGGGCTTCCGCGATCATCTGTCTGACCAGCAGATCGCCGATGTTGTGAACTTCA
  M  P  G  F  R  D  H  L  S  D  Q  Q  I  A  D  V  V  N  F  M 4210      4220      4230      4240      4250      4260
TGCGCAAGAGCTGGGGCAACCAGGCTCCGGGAACCCTGTCTGCCTCGGATATCCGCAAGC
  R  K  S  W  G  N  Q  A  P  G  T  L  S  A  S  D  I  R  K  L 4270      4280      4290      4300      4310      4320
TCCGCACATCGGGTACTGCGGTTTCCACGGCCGGCTGGAACGTCTCTTCCAAGGGCTGGA
  R  T  S  G  T  A  V  S  T  A  G  W  N  V  S  S  K  G  W  M 4330      4340      4350      4360      4370      4380
TGGCCTACATGCCGCAGCCTTATGGCGAAGGCTGGACCTTCTCCCCGCAGACACACACGG
  A  Y  M  P  Q  P  Y  G  E  G  W  T  F  S  P  Q  T  H  T  G 4390      4400      4410      4420      4430      4440
GCGTGGATCAGGCTCAGTAAGCCTCTCCAGACCCTGTCAGTCTGACAGAAAAGGGCGGTC
  V  D  Q  A  Q  *

4450      4460      4470      4480      4490      4500
CGGATACGGGCCGCCTTTTTCTTTTGTATTCAGGCCGTTTTCACAGGATGGCATCCTGCA 4510      4520      4530      4540      4550      4560
CTACATATGAAGGCATGACTCCCTTCTCGTCTTCTGCTCCGCAGTCAGTTTTTCCTTTGG 4570      4580      4590      4600      4610      4620
CAACAGGCGCAGGCCGCGCAGCATTGCCATCATGCGCGCCAGGACCCGGAAGCGCCGAGC 4630      4640      4650      4660      4670      4680
TTCTCAAGAGCCTCTGCGGTTCCCTTCCTGACCCTCGACGCGCCACCTGCGCAGCTGCGC
```

FIG. 8F

```
         4690      4700      4710      4720      4730      4740
CATCAAGGCGAAGTGCTGGATCATGCCGTGGTTCTCTGGCTTCCTGGACCGAAATCCTAC 4750      4760      4770      4780      4790      4800
ACCGGCGAAGACGGGTGTCGAACTCCACCTTCATGCTGGACCCGCTGTTATCACTCGCGT 4810      4820      4830
TGCGGATGCTCTGACCGATCTGGGTGCACG
```

FIG. 8G

```
          10        20        30        40        50        60
CGAAGCGATCGGGACTTTTCAGGGAGCCGGGAAGCTGGCCGCCTGTCTGGATCTTCTCGC 70        80        90       100       110       120
CACACTGACGTCTGCTCCGTTCAGGACGCTGTCCCTCAAAGGGGAGACCAAGGCTCTCAA 130       140       150       160       170       180
CAGCCCGGAAATGCAGCGGATAAGCGGTGTCATCACATCCCTGATGGCCATGGACCCATC 190       200       210       220       230       240
CGAAATCCGGCATGACCATCTGGCGCAGGATCTGGGCCTCTGCGCATCCACCTTCTCTCG 250       260       270       280       290       300
CCAGTTCCGTTCTGCGACGGGCGACACATTCATGTCTTTCCTGCATCGGCTGCGGGTGTG 310       320       330       340       350       360
TCACGCGTGCCATCTGCTGGCCAGTTCCACACTCTCAATCACGGAAATCGGGGCTGCTTC 370       380       390       400       410       420
CGGCTTCAACAACCTGTCCAATTTTAACCGCATCTTCCTGCGCCTGCGTGGCTGCACGCC 430       440       450       460       470       480
ACGGGAATACCGCCGTCATGCCCGCGAAATGACAGCCCTTTCGCCGACAGACGCCGCAGA 490       500       510       520       530       540
TTTCCTGAACTGACCGACAAGGGAAAACAGATCATGCCAACACTTCCACAACGTTTTTCC 550       560       570       580       590       600
CTCGATGGTCGCAAAGCTCTTGTCACGGGTGCATCCGCGGGCTTGGTGTTACGATCTGC 610       620       630       640       650       660
GACGTTCTGAGTGCTGCGGGGGCCGATATTGTCGCCGTTGCGCGTTCTGAAACCGACATG 670       680       690       700       710       720
GCCGCCACATGCCGGATCGTGGAAGGCCATGGTCGTCAATGCCTCACGGTTGTTGCCGAT 730       740       750       760       770       780
CTCAGTGATCCGATGGCTCCGGACGCTGTCGCGCAGACAGTGAACGCAGCGTGGGGTGGG
```

FIG.10A

```
         790       800       810       820       830       840
GTGGATATTGTCGTCAACAATGCTGGCGTCAGTTTCCCTCGCCCTCTGGTGGAACAGACC 850       860       870       880       890       900
GTCGAGGAGTGGGACACCGTGCAGGCCATTAACCTGCGTGCGCCATGGCTTCTCGCCCGT 910       920       930       940       950       960
GTCTTCGCTCCGGGCATGATTGAACGCAAGCGTGGGAAAATCATCAACATCAGTTCCCAG 970       980       990      1000      1010      1020
GCCAGCTCTGTCGCGCTGATTGACCATGGTGCTTACGTCGCATCCAAGGCCGGTCTGAAC 1030      1040      1050      1060      1070      1080
GGTCTCACCAAGGTCATGACGGCGGAATGGGCGGCTCATAACATACAGGCCAATGCCATC 1090      1100      1110      1120      1130      1140
TGCCCCACAGTCGTCTGGACGCCCATGGGTGAACGCGTCTGGAGCGTTGGGAACAAGCTG 1150      1160      1170      1180      1190      1200
GAAAAGCTACTGGAAAAGATCCCCGCTGGCCGTGTCGCAACACCGGAAGATGTCGCGGAT 1210      1220      1230      1240      1250      1260
ATAGTTCTGTATCTCGCCTCCGACGCGTCGAGCATGGTCAACGGGCAGGAAATATTTGTC 1270      1280      1290      1300      1310      1320
GATGGCGGATACACAGCCCTTTAGGCCGCCACATCTTCAAATAAAGACATGTGATTTTAC 1330      1340      1350      1360      1370      1380
GGTTTTAACAAGGCCATGTGCAGGGAATGGCCTGCGCATTTCATGCAGATCAAC|AGG|TGT 1390      1400      1410      1420      1430      1440
AACATGAAGACCAAGACGCTTCCGCTGGCCCTTCTGTCTCTCGCTCTTGGCGGGACGGCC
     M  K  T  K  T  L  P  L  A  L  L  S  L  A  L  G  G  T  A 1450      1460▼    1470      1480      1490      1500
CTGTCAGACCCGGCTGCCGCAGCTGGAACCCCGCTGAAAATTGGCGTTTCCTTTCAGGAA
  L  S  D  P  A  A  A  A  G  T  P  L  K  I  G  V  S  F  Q  E 1510      1520      1530      1540      1550      1560
ATGAACAATCCGTACTTCGTCACCATGAAGGACGCATTGCAGGAAGCCGCTGGCACGATC
  M  N  N  P  Y  F  V  T  M  K  D  A  L  Q  E  A  A  G  T  I
```

FIG. 10B

```
       1570      1580      1590      1600      1610      1620
GGTGCGAATGTCATCATCAGTGATGCGCATCATGATGTTTCCAAGCAGGTGAGTGACATT
 G   A   N   V   I   I   S   D   A   H   H   D   V   S   K   Q   V   S   D   I 1630      1640      1650      1660      1670      1680
GAGGACATGATCCAGCAGGGCGCGCAGATCATCATCATCAACCCGACCGATACAGTAGGC
 E   D   M   I   Q   Q   G   A   Q   I   I   I   I   N   P   T   D   T   V   G 1690      1700      1710      1720      1730      1740
GTCACGTCCGTCGTAAAGAGCGTTCATGACAAGAACATCCCGATCGTCTCGGTGGATGCT
 V   T   S   V   V   K   S   V   H   D   K   N   I   P   I   V   S   V   D   A 1750      1760      1770      1780      1790      1800
CAGGCTGGCGGTCCGCTCGATGCGTTTGTGGGGTCCAAGAACTATGATGCCGGCTTCAAG
 Q   A   G   G   P   L   D   A   F   V   G   S   K   N   Y   D   A   G   F   K 1810      1820      1830      1840      1850      1860
GCCTGCGAGTATCTCGCCACGACGATCAAGAGCGGCAATATCGGAATCATCGACGGTATC
 A   C   E   Y   L   A   T   T   I   K   S   G   N   I   G   I   I   D   G   I 1870      1880      1890      1900      1910      1920
CCGGTCGTTCCCATTCTTGAGCGTGTCAAAGGCTGCAAAAACGCTATCGCCAAGCATTCA
 P   V   V   P   I   L   E   R   V   K   G   C   K   N   A   I   A   K   H   S 1930      1940      1950      1960      1970      1980
GATATCAAGATTGTCAGCGTTCAGAACGGCAAGCAGGAGCGCGATGAGGCTCTGACGGTG
 D   I   K   I   V   S   V   Q   N   G   K   Q   E   R   D   E   A   L   T   V 1990      2000      2010      2020      2030      2040
GCTGAAAACATGCTCCAGGCCAACCCGGATCTGAAAGGTATCTTCAGCGTCAATGACAAC
 A   E   N   M   L   Q   A   N   P   D   L   K   G   I   F   S   V   N   D   N 2050      2060      2070      2080      2090      2100
GGATCGCTCGGTGTGCTGTCCGCTATCGAATCCAGTGGTTCAGACGTGAAGCTGGTCAGC
 G   S   L   G   V   L   S   A   I   E   S   S   G   S   D   V   K   L   V   S 2110      2120      2130      2140      2150      2160
GTTGATGGCAACCCGGAAGCCGTGAAGGCCATCTACAAGCCAGGCTCTCATTTCATCGCT
 V   D   G   N   P   E   A   V   K   A   I   Y   K   P   G   S   H   F   I   A 2170      2180      2190      2200      2210      2220
ACGGCTGCGCAGTTCCCCCGGCAGGATATCCGTCTGGCACTGGCGCTCGCCCTTGCCAGG
 T   A   A   Q   F   P   R   Q   D   I   R   L   A   L   A   L   A   R 2230      2240      2250      2260      2270      2280
AAATGGGGCGCAGGCGTGCCGAAGGTCCTGCCTGTTGATGTCGAGCTGATCGACGCGACG
 K   W   G   A   G   V   P   K   V   L   P   V   D   V   E   L   I   D   A   T 2290      2300      2310      2320      2330      2340
AAAGCCAAGACGTTCAGCTGGTAAATTCCGAAGGCGGCCCCGAATTCCGGAGGGAACATT
 K   A   K   T   F   S   W   *
```

FIG. 10C

```
          2350      2360      2370      2380      2390      2400
ATGACTGAATCCAGTCAGACATCTCCAGAACTTCTTCTGGCGCTTGAGGGAATCTCCAAG 2410      2420      2430      2440      2450      2460
AGTTTTCCGGGAGTCCGGGCGTTGCGGAATGTCAGCCTCAGCCTGGAGCGTGGAGAAATC 2470      2480      2490      2500      2510      2520
CATGCTCTGCTGGGGGAAAACGGCGCTGGAAAATCCACGATCATCAAGATCATGGGCGGT 2530      2540      2550      2560      2570      2580
ATCCAGTCTCAGGATGAAGGGCAGATCTTTCTCAACGGAAAGGAGCGCCACTTCTCCAGC 2590      2600      2610      2620      2630      2640
TACAAGGATGCCATCAGCGCAGGTATCGGGATTGTTTTCAGGAATTCAGCCTGATTCCT 2650      2660      2670      2680      2690      2700
GAACTCGATGCCGTGGATAATATTTTCCTCGGTCGTGAGATGCGGAACGCTCTTGGCTTT
```

FIG. 10D

SEQUENCE LISTING

<160> NUMBER OF SEQ ID NOS: 87

<210> SEQ ID NO 1
<211> LENGTH: 2265
<212> TYPE: DNA
<213> ORGANISM: Gluconobacter suboxydans

<400> SEQUENCE: 1

```
atggtttctg gtctactgac gccgatcaac gttacgaaga agcgccttct gggttgcgct      60
gctgctctgg cattctgcgc cacctctcct gtcgccctgg ctgaggacac aggaacagcc     120
```

-continued

| | |
|---|---|
| attacaaacg ccgaccagca tccgggtgac tggatgagct atggccggac ctattccgag | 180 |
| cagcgctaca gcccgctgga tcagatcacc aaggacaatg cgagcaatct gaagctggca | 240 |
| tggcactacg atctggatac caaccgtggt caggaaggta cgccgctgat cgttgatggc | 300 |
| gtcatgtacg ccaccacaaa ctggagcaag atgaaggctc tggatgcagc tacgggcaag | 360 |
| ctgctgtggt cttacgatcc aaaggttcca ggcaacatcg ccgaccgcgg ctgctgcgat | 420 |
| acggtcaacc gtggtgcagc ctactggaac ggcaaagtct atttcggcac cttcgacggt | 480 |
| cgcctgattg ccctggatgc caagaccggc aagctggtct ggagcgtcta tacggttccc | 540 |
| aaggaagcgc agctgggtca ccagcgctcc tacacggttg acggtgctcc ccgtatcgcc | 600 |
| aagggcaagg tcatcatcgg caacggcggt gcagagttcg cgcccgtgg cttcgtgacg | 660 |
| gcgtatgacg ctgaaacggg aaagatggac tggcgcttct tcaccgttcc gaaccctgac | 720 |
| aacaagccgg acggcgcagc gtcctgacgac gtgctgatgt ccaaggctta tccgacatgg | 780 |
| ggcaagggcg gcgcgtggaa gcagcagggc ggtggcggta ccgtctggga ttcgctgatc | 840 |
| tatgaccctg taacggatct cgtctatctg gcgtcggta acggctcgcc atggaactac | 900 |
| aagttccgtt ctgaaggaaa aggcaacaac ctcttcctcg gcagcatcgt ggccatcaat | 960 |
| cctgacaccg gcaaatacgt ctggcatttc caggaaacgc caatggacca gtgggattat | 1020 |
| acctcggttc agcagatcat ggccctcgac atgccggtca atggcgaaat cgccatgtg | 1080 |
| ctcgtgcatg cgccgaagaa cggcttcttc tatatcattg atgccaagac cggtaagttc | 1140 |
| atctccggca agccgtacac ctacgagaac tgggccaatg gcctcgatcc ggtaacgggt | 1200 |
| cgtccgaact acaatccaga tgctctctgg acgctgaacg gcaagccctg gtacggcatc | 1260 |
| cccgcgatc tgggtggtca taacttcgct gccatggctt acagcccaca gacgaagctg | 1320 |
| gtttacattc ccgcccagca ggttcccttc gtttacgatc cgcagaaggg tggcttcaag | 1380 |
| gctcaccacg acagctggaa ccttggcctc gacatgaaca gatcggcct gcttgatgac | 1440 |
| aacgatccac agcacaaggc tgacaaggcc cagttcctga aggatctgaa gggctggatc | 1500 |
| gttgcatggg atccgcagaa gcagcaggca gccttcacgg ttgaccacaa gggtccgtgg | 1560 |
| aatggcggtc ttctggcaac ggctggtggc gttctgttcc agggtctcgc caacggtgag | 1620 |
| ttccacgcct acgacgcgac gacgggtaag gatctcttca ccttcccagc acagagcgcc | 1680 |
| atcattgccc cgccagtcac ctacacagcc aacggcaagc agtatgttgc ggttgaagtg | 1740 |
| ggctgggcg gtatctatcc gttcttcctg gcggcgtag cccgtacgtc cggctggacc | 1800 |
| gtcaaccact cccggatcat cgcgttcgct ctggacggca acgacaagct gccagccaag | 1860 |
| aacgagctcg gcttcgttcc agtgaagccg cctgagaaat gggatgaagc caagatcaag | 1920 |
| gacggctact ccagttcca gacctattgc gcagcctgcc atggtgacaa cggtatctcc | 1980 |
| ggcggtgttc tgccagacct cgctggtcc ggtgcgatcc gtggagagga gaagttctac | 2040 |
| aagctcgtcg gcaagggtgc tctaacggcc tacggtatgg accgtttcga cacgtccatg | 2100 |
| tcgccagctg aaatcgaaga catccgcaac ttccttgtga agcgcgccaa cgagtcctac | 2160 |
| gcagacgaag tcaaggcccg aaagaatgag gcaggcgtcc ctaacggcga attcctcaac | 2220 |
| gtccctcagg gttcggttgc gcctgcaacg ccggaccatc cgtaa | 2265 |

<210> SEQ ID NO 2
<211> LENGTH: 1437
<212> TYPE: DNA
<213> ORGANISM: Gluconobacter suboxydans

<400> SEQUENCE: 2

```
atgctcaagg cattaactcg ggacagactg gtatctgaga tgaaacaggg atggaaatac    60
gcggccgcag tcggcctcat ggcagtgtct ttcggtgctg cccaagccca ggacgctgat   120
gacgccctga ttcagcgcgg tgcctacgtg gcccgcctgt ctgactgcgt tgcctgccat   180
accgcactac acggccagcc ttttgctggt ggtctggaga tcaagagccc gatcggcacg   240
atctactcca ccaacatcac gcctgacccg aaatacggta tcggcaacta cactcgaa    300 gatttcacga aggcgatccg taagggtatc cgcaaggacg gcgcgacggt ttatccggcc   360
atgccgtatc ctgagttcgc tcgcctgtct gatgacgaca tcaaggccat gtatgccttc   420
ttcatgcatg gcgtgaagcc ggtcgccctt cagaacaagc agccggacat ctcctggccg   480
atgaacatgc gctggccgtt ggccatctgg cgcgcgatgt ttgttccgac tgtcacacca   540
ggcctcgaca gagcatctc cgatccggaa gtggcgcgtg gcgaatacct cgtgaatggc   600
ccaggccatt gtggcgagtg tcatacgccc gtggcatgg ccatgcaggt caagggctat   660
acggccaagg acggcaacgc ttacctctcc ggtggcgcac cgatcgacaa ctggattgct   720
cccagcctgc gtagcaatag cgacacgggt ctgggtcgct ggtctgaaga cgacattgcc   780
gagttcctga agagcggccg tatcgaccat tctgccgtct tcggtggcat ggctgacgtg   840
gtggcctaca gcacccagca ctggaccgac gacgatctgc acgcaacggc caagtacctg   900
aagagcatgc cggccgttcc ggaaggcaaa aacctgggtc aggatgacgg caaggccacg   960
gccctgctcg aagccggtgg caaggtgat gcaggcgcag aggtttacct ccacaactgt   1020
gccatctgcc atatgaacga tggcactggt gtcaaccgca tgttcccgcc gctggctggc   1080
aacccggtcg tcatcacgga caatgcaacc tcaatggcca acatcgtgac attcggcggt   1140
attctgcctc cgacgaatac ggcgccatct gctgttgcca tgccgggctt ccgcgatcat   1200
ctgtctgacc agcagatcgc cgatgttgtg aacttcatgc gcaagagctg gggcaaccag   1260
gctccgggaa ccctgtctgc ctcggatatc cgcaagctcc gcacatcggg tactgcggtt   1320 tccacgccg gctggaacgt ctcttccaag ggctggatgg cctacatgcc gcagccttat   1380
ggcgaaggct ggaccttctc cccgcagaca cacacgggcg tggatcaggc tcagtaa     1437
```

<210> SEQ ID NO 3
<211> LENGTH: 921
<212> TYPE: DNA
<213> ORGANISM: Gluconobacter suboxydans

<400> SEQUENCE: 3

```
atgaagacca agacgcttcc gctggcccctt ctgtctctcg ctcttggcgg gacggccctg    60
tcagacccgg ctgccgcagc tggaaccccg ctgaaaattg gcgtttcctt tcaggaaatg   120
aacaatccgt acttcgtcac catgaaggac gcattgcagg aagccgctgg cacgatcggt   180
gcgaatgtca tcatcagtga tgcgcatcat gatgtttcca agcaggtgag tgacattgag   240
gacatgatcc agcagggcgc gcagatcatc atcatcaacc cgaccgatac agtaggcgtc   300
acgtccgtcg taaagagcgt tcatgacaag aacatcccga tcgtctcggt ggatgctcag   360
gctggcggtc cgctcgatgc gtttgtgggg tccaagaact atgatgccgg cttcaaggcc   420
tgcgagtatc tcgccacgac gatcaagagc ggcaatatcg gaatcatcga cggtatcccg   480
gtcgttccca ttcttgagcg tgtcaaaggc tgcaaaaacg ctatcgccaa gcattcagat   540
atcaagattg tcagcgttca gaacggcaag caggagcgcg atgaggctct gacggtggct   600
gaaaacatgc tccaggccaa cccggatctg aaaggtatct tcagcgtcaa tgacaacgga   660
```

```
tcgctcggtg tgctgtccgc tatcgaatcc agtggttcag acgtgaagct ggtcagcgtt    720
gatggcaacc cggaagccgt gaaggccatc tacaagccag gctctcattt catcgctacg    780
gctgcgcagt tccccggca ggatatccgt ctggcactgg cgctcgccct tgccaggaaa    840 tgggcgcag gcgtgccgaa ggtcctgcct gttgatgtcg agctgatcga cgcgacgaaa    900
gccaagacgt tcagctggta a                                              921
```

<210> SEQ ID NO 4
<211> LENGTH: 754
<212> TYPE: PRT
<213> ORGANISM: Gluconobacter suboxydans

<400> SEQUENCE: 4

```
Met Val Ser Gly Leu Leu Thr Pro Ile Asn Val Thr Lys Lys Arg Leu
 1               5                  10                  15

Leu Gly Cys Ala Ala Ala Leu Ala Phe Cys Ala Thr Ser Pro Val Ala
            20                  25                  30

Leu Ala Glu Asp Thr Gly Thr Ala Ile Thr Asn Ala Asp Gln His Pro
        35                  40                  45

Gly Asp Trp Met Ser Tyr Gly Arg Thr Tyr Ser Glu Gln Arg Tyr Ser
    50                  55                  60

Pro Leu Asp Gln Ile Thr Lys Asp Asn Ala Ser Asn Leu Lys Leu Ala
65                  70                  75                  80

Trp His Tyr Asp Leu Asp Thr Asn Arg Gly Gln Glu Gly Thr Pro Leu
                85                  90                  95

Ile Val Asp Gly Val Met Tyr Ala Thr Thr Asn Trp Ser Lys Met Lys
            100                 105                 110

Ala Leu Asp Ala Ala Thr Gly Lys Leu Leu Trp Ser Tyr Asp Pro Lys
        115                 120                 125

Val Pro Gly Asn Ile Ala Asp Arg Gly Cys Cys Asp Thr Val Asn Arg
    130                 135                 140

Gly Ala Ala Tyr Trp Asn Gly Lys Val Tyr Phe Gly Thr Phe Asp Gly
145                 150                 155                 160

Arg Leu Ile Ala Leu Asp Ala Lys Thr Gly Lys Leu Val Trp Ser Val
                165                 170                 175

Tyr Thr Val Pro Lys Glu Ala Gln Leu Gly His Gln Arg Ser Tyr Thr
            180                 185                 190

Val Asp Gly Ala Pro Arg Ile Ala Lys Gly Lys Val Ile Ile Gly Asn
        195                 200                 205

Gly Gly Ala Glu Phe Gly Ala Arg Gly Phe Val Thr Ala Tyr Asp Ala
    210                 215                 220

Glu Thr Gly Lys Met Asp Trp Arg Phe Phe Thr Val Pro Asn Pro Asp
225                 230                 235                 240

Asn Lys Pro Asp Gly Ala Ala Ser Asp Asp Val Leu Met Ser Lys Ala
                245                 250                 255

Tyr Pro Thr Trp Gly Lys Gly Ala Trp Lys Gln Gly Gly Gly
            260                 265                 270

Gly Thr Val Trp Asp Ser Leu Ile Tyr Asp Pro Val Thr Asp Leu Val
        275                 280                 285

Tyr Leu Gly Val Gly Asn Gly Ser Pro Trp Asn Tyr Lys Phe Arg Ser
    290                 295                 300

Glu Gly Lys Gly Asn Asn Leu Phe Leu Gly Ser Ile Val Ala Ile Asn
305                 310                 315                 320

Pro Asp Thr Gly Lys Tyr Val Trp His Phe Gln Glu Thr Pro Met Asp
```

```
                    325                 330                 335
Gln Trp Asp Tyr Thr Ser Val Gln Gln Ile Met Ala Leu Asp Met Pro
                340                 345                 350
Val Asn Gly Glu Met Arg His Val Leu Val His Ala Pro Lys Asn Gly
            355                 360                 365
Phe Phe Tyr Ile Ile Asp Ala Lys Thr Gly Lys Phe Ile Ser Gly Lys
        370                 375                 380
Pro Tyr Thr Tyr Glu Asn Trp Ala Asn Gly Leu Asp Pro Val Thr Gly
385                 390                 395                 400
Arg Pro Asn Tyr Asn Pro Asp Ala Leu Trp Thr Leu Asn Gly Lys Pro
                405                 410                 415
Trp Tyr Gly Ile Pro Gly Asp Leu Gly Gly His Asn Phe Ala Ala Met
            420                 425                 430
Ala Tyr Ser Pro Gln Thr Lys Leu Val Tyr Ile Pro Ala Gln Gln Val
        435                 440                 445
Pro Phe Val Tyr Asp Pro Gln Lys Gly Gly Phe Lys Ala His His Asp
    450                 455                 460
Ser Trp Asn Leu Gly Leu Asp Met Asn Lys Ile Gly Leu Leu Asp Asp
465                 470                 475                 480
Asn Asp Pro Gln His Lys Ala Asp Lys Ala Gln Phe Leu Lys Asp Leu
                485                 490                 495
Lys Gly Trp Ile Val Ala Trp Asp Pro Gln Lys Gln Ala Ala Phe
            500                 505                 510
Thr Val Asp His Lys Gly Pro Trp Asn Gly Gly Leu Leu Ala Thr Ala
        515                 520                 525
Gly Gly Val Leu Phe Gln Gly Leu Ala Asn Gly Glu Phe His Ala Tyr
    530                 535                 540
Asp Ala Thr Thr Gly Lys Asp Leu Phe Thr Phe Pro Ala Gln Ser Ala
545                 550                 555                 560
Ile Ile Ala Pro Pro Val Thr Thr Ala Asn Gly Lys Gln Tyr Val
                565                 570                 575
Ala Val Glu Val Gly Trp Gly Gly Ile Tyr Pro Phe Phe Leu Gly Gly
            580                 585                 590
Val Ala Arg Thr Ser Gly Trp Thr Val Asn His Ser Arg Ile Ile Ala
        595                 600                 605
Phe Ala Leu Asp Gly Asn Asp Lys Leu Pro Ala Lys Asn Glu Leu Gly
    610                 615                 620
Phe Val Pro Val Lys Pro Pro Glu Lys Trp Asp Glu Ala Lys Ile Lys
625                 630                 635                 640
Asp Gly Tyr Phe Gln Phe Gln Thr Tyr Cys Ala Ala Cys His Gly Asp
                645                 650                 655
Asn Gly Ile Ser Gly Gly Val Leu Pro Asp Leu Arg Trp Ser Gly Ala
            660                 665                 670
Ile Arg Gly Glu Glu Lys Phe Tyr Lys Leu Val Gly Lys Gly Ala Leu
        675                 680                 685
Thr Ala Tyr Gly Met Asp Arg Phe Asp Thr Ser Met Ser Pro Ala Glu
    690                 695                 700
Ile Glu Asp Ile Arg Asn Phe Leu Val Lys Arg Ala Asn Glu Ser Tyr
705                 710                 715                 720
Ala Asp Glu Val Lys Ala Arg Lys Asn Glu Ala Gly Val Pro Asn Gly
                725                 730                 735
Glu Phe Leu Asn Val Pro Gln Gly Ser Val Ala Pro Ala Thr Pro Asp
            740                 745                 750
```

His Pro

<210> SEQ ID NO 5
<211> LENGTH: 478
<212> TYPE: PRT
<213> ORGANISM: Gluconobacter suboxydans

<400> SEQUENCE: 5

```
Met Leu Lys Ala Leu Thr Arg Asp Arg Leu Val Ser Glu Met Lys Gln
  1               5                  10                  15

Gly Trp Lys Tyr Ala Ala Val Gly Leu Met Ala Val Ser Phe Gly
                 20                  25                  30

Ala Ala Gln Ala Gln Asp Ala Asp Asp Ala Leu Ile Gln Arg Gly Ala
             35                  40                  45

Tyr Val Ala Arg Leu Ser Asp Cys Val Ala Cys His Thr Ala Leu His
 50                  55                  60

Gly Gln Pro Phe Ala Gly Gly Leu Glu Ile Lys Ser Pro Ile Gly Thr
 65                  70                  75                  80

Ile Tyr Ser Thr Asn Ile Thr Pro Asp Pro Lys Tyr Gly Ile Gly Asn
                 85                  90                  95

Tyr Thr Leu Glu Asp Phe Thr Lys Ala Ile Arg Lys Gly Ile Arg Lys
            100                 105                 110

Asp Gly Ala Thr Val Tyr Pro Ala Met Pro Tyr Pro Glu Phe Ala Arg
            115                 120                 125

Leu Ser Asp Asp Ile Lys Ala Met Tyr Ala Phe Phe Met His Gly
130                 135                 140

Val Lys Pro Val Ala Leu Gln Asn Lys Gln Pro Asp Ile Ser Trp Pro
145                 150                 155                 160

Met Asn Met Arg Trp Pro Leu Ala Ile Trp Arg Ala Met Phe Val Pro
                165                 170                 175

Thr Val Thr Pro Gly Leu Asp Lys Ser Ile Ser Asp Pro Glu Val Ala
            180                 185                 190

Arg Gly Glu Tyr Leu Val Asn Gly Pro Gly His Cys Gly Glu Cys His
            195                 200                 205

Thr Pro Arg Gly Met Ala Met Gln Val Lys Gly Tyr Thr Ala Lys Asp
210                 215                 220

Gly Asn Ala Tyr Leu Ser Gly Ala Pro Ile Asp Asn Trp Ile Ala
225                 230                 235                 240

Pro Ser Leu Arg Ser Asn Ser Asp Thr Gly Leu Gly Arg Trp Ser Glu
                245                 250                 255

Asp Asp Ile Ala Glu Phe Leu Lys Ser Gly Arg Ile Asp His Ser Ala
            260                 265                 270

Val Phe Gly Gly Met Ala Asp Val Val Ala Tyr Ser Thr Gln His Trp
            275                 280                 285

Thr Asp Asp Asp Leu His Ala Thr Ala Lys Tyr Leu Lys Ser Met Pro
290                 295                 300

Ala Val Pro Glu Gly Lys Asn Leu Gly Gln Asp Gly Lys Ala Thr
305                 310                 315                 320

Ala Leu Leu Glu Ala Gly Gly Lys Gly Asp Ala Gly Ala Glu Val Tyr
                325                 330                 335

Leu His Asn Cys Ala Ile Cys His Met Asn Asp Gly Thr Gly Val Asn
            340                 345                 350

Arg Met Phe Pro Pro Leu Ala Gly Asn Pro Val Val Ile Thr Asp Asn
            355                 360                 365
```

```
Ala Thr Ser Met Ala Asn Ile Val Thr Phe Gly Ile Leu Pro Pro
    370                 375                 380

Thr Asn Thr Ala Pro Ser Ala Val Ala Met Pro Gly Phe Arg Asp His
385                 390                 395                 400

Leu Ser Asp Gln Gln Ile Ala Asp Val Val Asn Phe Met Arg Lys Ser
                405                 410                 415

Trp Gly Asn Gln Ala Pro Gly Thr Leu Ser Ala Ser Asp Ile Arg Lys
                420                 425                 430

Leu Arg Thr Ser Gly Thr Ala Val Ser Thr Ala Gly Trp Asn Val Ser
            435                 440                 445

Ser Lys Gly Trp Met Ala Tyr Met Pro Gln Pro Tyr Gly Glu Gly Trp
    450                 455                 460

Thr Phe Ser Pro Gln Thr His Thr Gly Val Asp Gln Ala Gln
465                 470                 475

<210> SEQ ID NO 6
<211> LENGTH: 306
<212> TYPE: PRT
<213> ORGANISM: Gluconobacter suboxydans

<400> SEQUENCE: 6

Met Lys Thr Lys Thr Leu Pro Leu Ala Leu Leu Ser Leu Ala Leu Gly
  1               5                  10                  15

Gly Thr Ala Leu Ser Asp Pro Ala Ala Ala Gly Thr Pro Leu Lys
             20                  25                  30

Ile Gly Val Ser Phe Gln Glu Met Asn Asn Pro Tyr Phe Val Thr Met
             35                  40                  45

Lys Asp Ala Leu Gln Glu Ala Ala Gly Thr Ile Gly Ala Asn Val Ile
    50                  55                  60

Ile Ser Asp Ala His His Asp Val Ser Lys Gln Val Ser Asp Ile Glu
65                  70                  75                  80

Asp Met Ile Gln Gln Gly Ala Gln Ile Ile Ile Asn Pro Thr Asp
                85                  90                  95

Thr Val Gly Val Thr Ser Val Val Lys Ser Val His Asp Lys Asn Ile
            100                 105                 110

Pro Ile Val Ser Val Asp Ala Gln Ala Gly Gly Pro Leu Asp Ala Phe
            115                 120                 125

Val Gly Ser Lys Asn Tyr Asp Ala Gly Phe Lys Ala Cys Glu Tyr Leu
130                 135                 140

Ala Thr Thr Ile Lys Ser Gly Asn Ile Gly Ile Ile Asp Gly Ile Pro
145                 150                 155                 160

Val Val Pro Ile Leu Glu Arg Val Lys Gly Cys Lys Asn Ala Ile Ala
                165                 170                 175

Lys His Ser Asp Ile Lys Ile Val Ser Val Gln Asn Gly Lys Gln Glu
            180                 185                 190

Arg Asp Glu Ala Leu Thr Val Ala Glu Asn Met Leu Gln Ala Asn Pro
        195                 200                 205

Asp Leu Lys Gly Ile Phe Ser Val Asn Asp Asn Gly Ser Leu Gly Val
    210                 215                 220

Leu Ser Ala Ile Glu Ser Ser Gly Ser Asp Val Lys Leu Val Ser Val
225                 230                 235                 240

Asp Gly Asn Pro Glu Ala Val Lys Ala Ile Tyr Lys Pro Gly Ser His
                245                 250                 255

Phe Ile Ala Thr Ala Ala Gln Phe Pro Arg Gln Asp Ile Arg Leu Ala
```

-continued

```
                260                 265                 270
Leu Ala Leu Ala Leu Ala Arg Lys Trp Gly Ala Gly Val Pro Lys Val
                    275                 280                 285

Leu Pro Val Asp Val Glu Leu Ile Asp Ala Thr Lys Ala Lys Thr Phe
        290                 295                 300

Ser Trp
305
```

<210> SEQ ID NO 7
<211> LENGTH: 4830
<212> TYPE: DNA
<213> ORGANISM: Gluconobacter suboxydans

<400> SEQUENCE: 7

| | | | | |
|---|---|---|---|---|
| cgagaacgga | agcccgctga | aatcgacccg | ttccccatca | aaatactttt | cgagaagatc |   60 |
| acgaaccttc | accaggagcg | gcgtctcttc | ctgatcgcgc | ccccacccc | aatcgagagc |  120 |
| aacaatacgc | ccgtcatctt | cactgatggt | cagggctccg | agatgggaat | ggcaggaaag |  180 |
| ctgtggcata | cagatacgct | gccccatccc | ccggaaagcg | tcaatcatgc | ttccctaaaa |  240 |
| gagtccctga | aaaaaaata | catgcgtgtc | acgcatatgc | agggaggccg | gtattctcaa |  300 |
| ataacatatg | ggatcatttt | tgtatgattt | catgaaatat | tacgcacttt | gttgagaaac |  360 |
| tgccattttt | tgtgtcaaac | ctgcgacaga | cactaaagct | gttttggttg | tttggttatt |  420 |
| aagaataatt | ctcatgtaat | taagcgagcg | attttacgcg | gatagtgctc | acggagacgt |  480 |
| cagaagccca | cgtttccgac | aaacaataaa | ataagcgagt | agtaagttca | cgcgatgcta |  540 |
| cgttttccag | acgacttgga | gaaactgagg | agcacctagg | cacccacaga | ggcgcctatc |  600 |
| aggacttgga | ttacgtctga | ataccattaa | caggaacagt | ctttgcaaaa | aggacagtcg |  660 |
| gatcatggtt | tctggtctac | tgacgccgat | caacgttacg | aagaagcgcc | ttctgggttg |  720 |
| cgctgctgct | ctggcattct | gcgccacctc | tcctgtcgcc | ctggctgagg | acacaggaac |  780 |
| agccattaca | aacgccgacc | agcatccggg | tgactggatg | agctatggcc | ggacctattc |  840 |
| cgagcagcgc | tacagcccgc | tggatcagat | caccaaggac | aatgcgagca | atctgaagct |  900 |
| ggcatggcac | tacgatctgg | ataccaaccg | tggtcaggaa | ggtacgccgc | tgatcgttga |  960 |
| tggcgtcatg | tacgccacca | caaactggag | caagatgaag | gctctggatg | cagctacggg | 1020 |
| caagctgctg | tggtcttacg | atccaaaggt | tccaggcaac | atcgccgacc | gcggctgctg | 1080 |
| cgatacggtc | aaccgtggtg | cagcctactg | gaacggcaaa | gtctatttcg | gcaccttcga | 1140 |
| cggtcgcctg | attgccctgg | atgccaagac | cggcaagctg | gtctggagcg | tctatacggt | 1200 |
| tcccaaggaa | gcgcagctgg | gtcaccagcg | ctcctacacg | gttgacggtg | ctccccgtat | 1260 |
| cgccaagggc | aaggtcatca | tcggcaacgg | cggtgcagag | ttcggcgccc | gtggcttcgt | 1320 |
| gacggcgtat | gacgctgaaa | cgggaaagat | ggactggcgc | ttcttcaccg | ttccgaaccc | 1380 |
| tgacaacaag | ccggacggcg | cagcgtctga | cgacgtgctg | atgtccaagg | cttatccgac | 1440 |
| atggggcaag | ggcggcgcgt | ggaagcagca | gggcggtggc | ggtaccgtct | gggattcgct | 1500 |
| gatctatgac | cctgtaacgg | atctcgtcta | tctgggcgtc | ggtaacggct | cgccatggaa | 1560 |
| ctacaagttc | cgttctgaag | gaaaaggcaa | caacctcttc | ctcggcagca | tcgtggccat | 1620 |
| caatcctgac | accggcaaat | acgtctggca | tttccaggaa | acgccaatgg | accagtggga | 1680 |
| ttatacctcg | gttcagcaga | tcatggccct | cgacatgccg | gtcaatggcg | aaatgcgcca | 1740 |
| tgtgctcgtg | catgcgccga | agaacggctt | cttctatatc | attgatgcca | agaccggtaa | 1800 |

-continued

```
gttcatctcc ggcaagccgt acacctacga gaactgggcc aatggcctcg atccggtaac    1860
gggtcgtccg aactacaatc cagatgctct ctggacgctg aacggcaagc cctggtacgg    1920
catccccggc gatctggtg gtcataactt cgctgccatg gcttacagcc cacagacgaa     1980
gctggtttac attcccgccc agcaggttcc cttcgtttac gatccgcaga agggtggctt    2040
caaggctcac cacgacagct ggaaccttgg cctcgacatg aacaagatcg gcctgcttga    2100
tgacaacgat ccacagcaca aggctgacaa ggcccagttc ctgaaggatc tgaagggctg    2160
gatcgttgca tgggatccgc agaagcagca ggcagccttc acggttgacc acaagggtcc    2220
gtggaatggc ggtcttctgg caacggctgg tggcgttctg ttccagggtc tcgccaacgg    2280
tgagttccac gcctacgacg cgacgacggg taaggatctc ttcaccttcc cagcacagag    2340
cgccatcatt gccccgccag tcacctacac agccaacggc aagcagtatg ttgcggttga    2400
agtgggctgg ggcggtatct atccgttctt cctgggcggc gtagcccgta cgtccggctg    2460
gaccgtcaac cactcccgga tcatcgcgtt cgctctggac ggcaacgaca agctgccagc    2520
caagaacgag ctcggcttcg ttccagtgaa gccgcctgag aaatgggatg aagccaagat    2580
caaggacggc tacttccagt tccagaccta ttgcgcagcc tgccatggtg acaacggtat    2640
ctccggcggt gttctgccag acctgcgctg gtccggtgcg atccgtggag aggagaagtt    2700
ctacaagctc gtcggcaagg gtgctctaac ggcctacggt atggaccgtt tcgacacgtc    2760
catgtcgcca gctgaaatcg aagacatccg caacttcctt gtgaagcgcg ccaacgagtc    2820
ctacgcagac gaagtcaagg cccgaaagaa tgaggcaggc gtccctaacg gcgaattcct    2880
caacgtccct cagggttcgg ttgcgcctgc aacgccggac catccgtaac gggaaaccgt    2940
cacgctgaaa ggaatgacgt gacatgctca aggcattaac tcgggacaga ctggtatctg    3000
agatgaaaca gggatggaaa tacgcggccg cagtcggcct catggcagtg tctttcggtg    3060
ctgcccaagc ccaggacgct gatgacgccc tgattcagcg cggtgcctac gtggcccgcc    3120
tgtctgactg cgttgcctgc cataccgcac tacacggcca gccttttgct ggtggtctgg    3180
agatcaagag cccgatcggc acgatctact ccaccaacat cacgcctgac cgaaaatacg    3240
gtatcggcaa ctatacactc gaagatttca cgaaggcgat ccgtaagggt atccgcaagg    3300
acggcgcgac ggtttatccg gccatgccgt atcctgagtt cgctcgcctg tctgatgacg    3360
acatcaaggc catgtatgcc ttcttcatgc atggcgtgaa gccggtcgcc cttcagaaca    3420
agcagccgga catctcctgg ccgatgaaca tgcgctggcc gttggccatc tggcgcgcga    3480
tgtttgttcc gactgtcaca ccaggcctcg acaagagcat ctccgatccg gaagtggcgc    3540
gtggcgaata cctcgtgaat ggcccaggcc attgtggcga tgtcatacg ccccgtggca    3600 tggccatgca ggtcaagggc tatacggcca aggacggcaa cgcttacctc tccggtggcg    3660
caccgatcga caactggatt gctcccagcc tgcgtagcaa tagcgacacg ggtctgggtc    3720
gctggtctga agacgacatt gccgagttcc tgaagagcgg ccgtatcgac cattctgccg    3780
tcttcggtgg catggctgac gtggtggcct acagcaccca gcactggacc gacgacgatc    3840
tgcacgcaac ggccaagtac ctgaagagca tgccggccgt tccggaaggc aaaaacctgg    3900
gtcaggatga cggcaaggcc acggccctgc tcgaagccgg tggcaagggt gatgcaggcg    3960
cagaggttta cctccacaac tgtgccatct gccatatgaa cgatggcact ggtgtcaacc    4020
gcatgttccc gccgctggct ggcaacccgg tcgtcatcac ggacaatgca acctcaatgg    4080
ccaacatcgt gacattcggc ggtattctgc ctccgacgaa tacggcgcca tctgctgttg    4140
ccatgccggg cttccgcgat catctgtctg accagcagat cgccgatgtt gtgaacttca    4200
```

```
tgcgcaagag ctggggcaac caggctccgg gaaccctgtc tgcctcggat atccgcaagc    4260
tccgcacatc gggtactgcg gtttccacgg ccggctggaa cgtctcttcc aagggctgga    4320
tggcctacat gccgcagcct tatggcgaag gctggacctt ctccccgcag acacacacgg    4380
gcgtggatca ggctcagtaa gcctctccag accctgtcag tctgacagaa aagggcggtc    4440
cggatacggg ccgccttttt cttttgtatt caggccgttt tcacaggatg gcatcctgca    4500
ctacatatga aggcatgact cccttctcgt cttctgctcc gcagtcagtt tttcctttgg    4560
caacaggcgc aggccgcgca gcattgccat catgcgcgcc aggacccgga agcgccgagc    4620
ttctcaagag cctctgcggt tcccttcctg accctcgacg cgccacctgc gcagctgcgc    4680
catcaaggca agtgctgga tcatgccgtg gttctctggc ttcctggacc gaaatcctac    4740
accggcgaag acgggtgtcg aactccacct tcatgctgga cccgctgtta tcactcgcgt    4800
tgcggatgct ctgaccgatc tgggtgcacg                                     4830

<210> SEQ ID NO 8
<211> LENGTH: 2700
<212> TYPE: DNA
<213> ORGANISM: Gluconobacter suboxydans

<400> SEQUENCE: 8
cgaagcgatc gggactttc agggagccgg gaagctggcc gcctgtctgg atcttctcgc      60
cacactgacg tctgctccgt tcaggacgct gtccctcaaa ggggagacca aggctctcaa    120
cagcccggaa atgcagcgga taagcggtgt catcacatcc ctgatggcca tggacccatc    180
cgaaatccgg catgaccatc tggcgcagga tctgggcctc tgcgcatcca ccttctctcg    240
ccagttccgt tctgcgacgg gcgacacatt catgtctttc ctgcatcggc tgcgggtgtg    300
tcacgcgtgc catctgctgg ccagttccac actctcaatc acggaaatcg gggctgcttc    360
cggcttcaac aacctgtcca atttaaccg catcttcctg cgcctgcgtg gctgcacgcc    420
acgggaatac cgccgtcatg cccgcgaaat gacagcccct tcgccgacag acgccgcaga    480
tttcctgaac tgaccgacaa gggaaaacag atcatgccaa cacttccaca cgttttttcc    540
ctcgatggtc gcaaagctct tgtcacgggt gcatcccgcg ggcttggtgt acgatctgc    600 gacgttctga gtgctgcggg ggccgatatt gtcgccgttg cgcgttctga aaccgacatg    660
gccgccacat gccggatcgt ggaaggccat ggtcgtcaat gcctcacggt tgttgccgat    720
ctcagtgatc cgatggctcc ggacgctgtc gcgcagacag tgaacgcagc gtggggtggg    780
gtggatattg tcgtcaacaa tgctggcgtc agtttccctc gccctctggt ggaacagacc    840
gtcgaggagt gggacaccgt gcaggccatt aacctgcgtg cgccatggct ctcgcccgt    900 gtcttcgctc cggcatgat tgaacgcaag cgtgggaaaa tcatcaacat cagttcccag    960
gccagctctg tcgcgctgat tgaccatggt gcttacgtcg catccaaggc cggtctgaac   1020
ggtctcacca aggtcatgac ggcggaatgg gcggctcata acatacaggc caatgccatc   1080
tgccccacag tcgtctggac gcccatgggt gaacgcgtct ggagcgttgg gaacaagctg   1140
gaaaagctac tggaaagat ccccgctggc cgtgtcgcaa caccggaaga tgtcgcggat   1200
atagttctgt atctcgcctc cgacgcgtcg agcatggtca acgggcagga aatatttgtc   1260
gatggcggat acacagccct ttaggccgcc acatcttcaa ataaagacat gtgattttac   1320
ggttttaaca aggccatgtg cagggaatgg cctgcgcatt tcatgcagat caacaggtgt   1380
aacatgaaga ccaagacgct tccgctggcc cttctgtctc tcgctcttgg cgggacggcc   1440
```

-continued

```
ctgtcagacc cggctgccgc agctggaacc ccgctgaaaa ttggcgtttc ctttcaggaa    1500
atgaacaatc cgtacttcgt caccatgaag gacgcattgc aggaagccgc tggcacgatc    1560
ggtgcgaatg tcatcatcag tgatgcgcat catgatgttt ccaagcaggt gagtgacatt    1620
gaggacatga tccagcaggg cgcgcagatc atcatcatca acccgaccga tacagtaggc    1680
gtcacgtccg tcgtaaagag cgttcatgac aagaacatcc cgatcgtctc ggtggatgct    1740
caggctggcg gtccgctcga tgcgtttgtg ggtccaaga actatgatgc cggcttcaag    1800
gcctgcgagt atctcgccac gacgatcaag agcggcaata tcggaatcat cgacggtatc    1860
ccggtcgttc ccattcttga gcgtgtcaaa ggctgcaaaa acgctatcgc caagcattca    1920
gatatcaaga ttgtcagcgt tcagaacggc aagcaggagc gcgatgaggc tctgacggtg    1980
gctgaaaaca tgctccaggc caacccggat ctgaaaggta tcttcagcgt caatgacaac    2040
ggatcgctcg gtgtgctgtc cgctatcgaa tccagtggtt cagacgtgaa gctggtcagc    2100
gttgatggca acccggaagc cgtgaaggcc atctacaagc aggctctcga tttcatcgct    2160
acggctgcgc agttccccg gcaggatatc cgtctggcac tggcgctcgc ccttgccagg    2220
aaatggggcg caggcgtgcc gaaggtcctg cctgttgatg tcgagctgat cgacgcgacg    2280
aaagccaaga cgttcagctg gtaaattccg aaggcggccc cgaattccgg agggaacatt    2340
atgactgaat ccagtcagac atctccagaa cttcttctgg cgcttgaggg aatctccaag    2400
agttttccgg gagtccgggc gttgcggaat gtcagcctca gcctggagcg tggagaaatc    2460
catgctctgc tggggaaaaa cggcgctgga aaatccacga tcatcaagat catgggcggt    2520
atccagtctc aggatgaagg gcagatcttt ctcaacggaa aggagcgcca cttctccagc    2580
tacaaggatg ccatcagcgc aggtatcggg attgtttttc aggaattcag cctgattcct    2640
gaactcgatg ccgtggataa tattttcctc ggtcgtgaga tgcggaacgc tcttggcttt    2700
```

<210> SEQ ID NO 9
<211> LENGTH: 15
<212> TYPE: PRT
<213> ORGANISM: Gluconobacter suboxydans

<400> SEQUENCE: 9

Glu Asp Thr Gly Thr Ala Ile Thr Asn Ala Asp Gln His Pro Gly
1               5                   10                  15

<210> SEQ ID NO 10
<211> LENGTH: 10
<212> TYPE: PRT
<213> ORGANISM: Gluconobacter suboxydans

<400> SEQUENCE: 10

Asp Ala Asp Asp Ala Leu Ile Gln Arg Gly
1               5                   10

<210> SEQ ID NO 11
<211> LENGTH: 25
<212> TYPE: PRT
<213> ORGANISM: Gluconobacter suboxydans

<400> SEQUENCE: 11

Ala Gly Thr Pro Leu Lys Ile Gly Val Ser Phe Gln Glu Met Asn Asn
1               5                   10                  15

Pro Tyr Phe Val Thr Met Lys Asp Ala
            20                  25

```
<210> SEQ ID NO 12
<211> LENGTH: 5
<212> TYPE: PRT
<213> ORGANISM: Gluconobacter suboxydans

<400> SEQUENCE: 12

His Ser Asp Ile Lys
  1               5

<210> SEQ ID NO 13
<211> LENGTH: 7
<212> TYPE: PRT
<213> ORGANISM: Gluconobacter suboxydans

<400> SEQUENCE: 13

Asn Tyr Asp Ala Gly Phe Lys
  1               5

<210> SEQ ID NO 14
<211> LENGTH: 8
<212> TYPE: PRT
<213> ORGANISM: Gluconobacter suboxydans

<400> SEQUENCE: 14

Lys Trp Gly Ala Gly Val Pro Lys
  1               5

<210> SEQ ID NO 15
<211> LENGTH: 26
<212> TYPE: DNA
<213> ORGANISM: Gluconobacter suboxydans
<220> FEATURE:
<221> NAME/KEY: modified_base
<222> LOCATION: (18)
<223> OTHER INFORMATION: i
<221> NAME/KEY: modified_base
<222> LOCATION: (21)
<223> OTHER INFORMATION: i
<221> NAME/KEY: modified_base
<222> LOCATION: (24)
<223> OTHER INFORMATION: i

<400> SEQUENCE: 15
ccggaattcg argayacngg nacngc                                      26

<210> SEQ ID NO 16
<211> LENGTH: 23
<212> TYPE: DNA
<213> ORGANISM: Gluconobacter suboxydans
<220> FEATURE:
<221> NAME/KEY: modified_base
<222> LOCATION: (6)
<223> OTHER INFORMATION: i
<221> NAME/KEY: modified_base
<222> LOCATION: (12)
<223> OTHER INFORMATION: i

<400> SEQUENCE: 16
athacnaayg cngaycarca rcc                                         23

<210> SEQ ID NO 17
<211> LENGTH: 29
<212> TYPE: PRT
<213> ORGANISM: Gluconobacter suboxydans
<220> FEATURE:
<221> NAME/KEY: UNSURE
<222> LOCATION: (1)
<223> OTHER INFORMATION: may be D, E, or N
<221> NAME/KEY: UNSURE
```

```
<222> LOCATION: (3)..(5)
<223> OTHER INFORMATION: may be any amino acid
<221> NAME/KEY: UNSURE
<222> LOCATION: (7)
<223> OTHER INFORMATION: may be R or K
<221> NAME/KEY: UNSURE
<222> LOCATION: (8)..(13)
<223> OTHER INFORMATION: may be any amino acid
<221> NAME/KEY: UNSURE
<222> LOCATION: (14)
<223> OTHER INFORMATION: may be F, Y, or W
<221> NAME/KEY: UNSURE
<222> LOCATION: (16)..(19)
<223> OTHER INFORMATION: may be any amino acid
<221> NAME/KEY: UNSURE
<222> LOCATION: (20)
<223> OTHER INFORMATION: may be L, I, V, or M
<221> NAME/KEY: UNSURE
<222> LOCATION: (21)..(23)
<223> OTHER INFORMATION: may be any amino acid
<221> NAME/KEY: UNSURE
<222> LOCATION: (25)..(27)
<223> OTHER INFORMATION: may be any amino acid
<221> NAME/KEY: UNSURE
<222> LOCATION: (29)
<223> OTHER INFORMATION: may be R or K

<400> SEQUENCE: 17

Xaa Trp Xaa Xaa Xaa Gly Xaa Xaa Xaa Xaa Xaa Xaa Xaa Xaa Ser Xaa
 1               5                   10                  15

Xaa Xaa Xaa Xaa Xaa Xaa Xaa Asn Xaa Xaa Xaa Leu Xaa
            20                  25

<210> SEQ ID NO 18
<211> LENGTH: 22
<212> TYPE: PRT
<213> ORGANISM: Gluconobacter suboxydans
<220> FEATURE:
<221> NAME/KEY: UNSURE
<222> LOCATION: (2)..(5)
<223> OTHER INFORMATION: may be any amino acid
<221> NAME/KEY: UNSURE
<222> LOCATION: (8)..(10)
<223> OTHER INFORMATION: may be any amino acid
<221> NAME/KEY: UNSURE
<222> LOCATION: (11)
<223> OTHER INFORMATION: may be D or N
<221> NAME/KEY: UNSURE
<222> LOCATION: (12)..(15)
<223> OTHER INFORMATION: may be L, I, V, M, F, or Y
<221> NAME/KEY: UNSURE
<222> LOCATION: (16)..(17)
<223> OTHER INFORMATION: may be any amino acid
<221> NAME/KEY: UNSURE
<222> LOCATION: (19)..(20)
<223> OTHER INFORMATION: may be any amino acid
<221> NAME/KEY: UNSURE
<222> LOCATION: (21)
<223> OTHER INFORMATION: may be S, T, or A

<400> SEQUENCE: 18

Trp Xaa Xaa Xaa Xaa Tyr Asp Xaa Xaa Xaa Xaa Xaa Xaa Xaa Xaa Xaa
 1               5                   10                  15

Xaa Gly Xaa Xaa Xaa Pro
            20

<210> SEQ ID NO 19
<211> LENGTH: 5
<212> TYPE: PRT
<213> ORGANISM: Gluconobacter suboxydans
<220> FEATURE:
<221> NAME/KEY: UNSURE
<222> LOCATION: (2)
```

<223> OTHER INFORMATION: may be any amino acid
<221> NAME/KEY: UNSURE
<222> LOCATION: (3)
<223> OTHER INFORMATION: may be any amino acid different from the
      amino acid in position 2

<400> SEQUENCE: 19

Cys Xaa Xaa Cys His
 1               5

<210> SEQ ID NO 20
<211> LENGTH: 25
<212> TYPE: DNA
<213> ORGANISM: Gluconobacter suboxydans

<400> SEQUENCE: 20
gggaattctt ycargaratg aayaa                                           25

<210> SEQ ID NO 21
<211> LENGTH: 25
<212> TYPE: DNA
<213> ORGANISM: Gluconobacter suboxydans

<400> SEQUENCE: 21
gggaattctt gaarccngcr tcrta                                           25

<210> SEQ ID NO 22
<211> LENGTH: 2163
<212> TYPE: DNA
<213> ORGANISM: Gluconobacter suboxydans

<400> SEQUENCE: 22
gaggacacag gaacagccat tacaaacgcc gaccagcatc cgggtgactg gatgagctat       60
ggccggacct attccgagca gcgctacagc ccgctggatc agatcaccaa ggacaatgcg      120
agcaatctga agctggcatg gcactacgat ctggatacca accgtggtca ggaaggtacg      180
ccgctgatcg ttgatggcgt catgtacgcc accacaaaact ggagcaagat gaaggctctg     240
gatgcagcta cgggcaagct gctgtggtct tacgatccaa aggttccagg caacatcgcc      300
gaccgcggct gctgcgatac ggtcaaccgt ggtgcagcct actggaacgg caaagtctat      360
ttcggcacct cgacggtcg cctgattgcc ctggatgcca agaccggcaa gctggtctgg       420
agcgtctata cggttcccaa ggaagcgcag ctgggtcacc agcgctccta cacggttgac      480
ggtgctcccc gtatcgccaa gggcaaggtc atcatcggca acgcggtgc agagttcggc       540 gcccgtggct tcgtgacggc gtatgacgct gaaacgggaa agatggactg gcgcttcttc     600
accgttccga accctgacaa caagccggac ggcgcagcgt ctgacgacgt gctgatgtcc     660
aaggcttatc cgacatgggg caagggcggc gcgtggaagc agcagggcgg tggcggtacc    720
gtctgggatt cgctgatcta tgaccctgta acggatctcg tctatctggg cgtcggtaac    780
ggctcgccat ggaactacaa gttccgttct gaaggaaaag caacaacct cttcctcggc     840 agcatcgtgg ccatcaatcc tgacaccggc aaatacgtct ggcatttcca ggaaacgcca    900
atggaccagt gggattatac ctcggttcag cagatcatgg ccctcgacat gccggtcaat    960
ggcgaaatgc gccatgtgct cgtgcatgcg ccgaagaacg gcttcttcta tcattgat     1020 gccaagaccg gtaagttcat ctccggcaag ccgtacacct acgagaactg ggccaatggc   1080
ctcgatccgg taacgggtcg tccgaactac aatccagatg ctctctggac gctgaacggc   1140
aagccctggt acggcatccc cggcgatctg ggtggtcata acttcgctgc catggcttac   1200

-continued

| | |
|---|---|
| agcccacaga cgaagctggt ttacattccc gcccagcagg ttcccttcgt ttacgatccg | 1260 |
| cagaagggtg gcttcaaggc tcaccacgac agctggaacc ttggcctcga catgaacaag | 1320 |
| atcggcctgc ttgatgacaa cgatccacag acaaggctg acaaggccca gttcctgaag | 1380 |
| gatctgaagg gctggatcgt tgcatgggat ccgcagaagc agcaggcagc cttcacggtt | 1440 |
| gaccacaagg gtccgtggaa tggcggtctt ctggcaacgg ctggtggcgt tctgttccag | 1500 |
| ggtctcgcca acggtgagtt ccacgcctac gacgcgacga cgggtaagga tctcttcacc | 1560 |
| ttcccagcac agagcgccat cattgccccg ccagtcacct acacagccaa cggcaagcag | 1620 |
| tatgttgcgg ttgaagtggg ctggggcggt atctatccgt tcttcctggg cggcgtagcc | 1680 |
| cgtacgtccg gctggaccgt caaccactcc cggatcatcg cgttcgctct ggacggcaac | 1740 |
| gacaagctgc cagccaagaa cgagctcggc ttcgttccag tgaagccgcc tgagaaatgg | 1800 |
| gatgaagcca agatcaagga cggctacttc cagttccaga cctattgcgc agcctgccat | 1860 |
| ggtgacaacg gtatctccgg cggtgttctg ccagacctgc gctggtccgg tgcgatccgt | 1920 |
| ggagaggaga agttctacaa gctcgtcggc aagggtgctc taacggccta cggtatggac | 1980 |
| cgtttcgaca cgtccatgtc gccagctgaa atcgaagaca tccgcaactt ccttgtgaag | 2040 |
| cgcgccaacg agtcctacgc agacgaagtc aaggcccgaa agaatgaggc aggcgtccct | 2100 |
| aacggcgaat tcctcaacgt ccctcagggt tcggttgcgc ctgcaacgcc ggaccatccg | 2160 |
| taa | 2163 |

<210> SEQ ID NO 23
<211> LENGTH: 1329
<212> TYPE: DNA
<213> ORGANISM: Gluconobacter suboxydans

<400> SEQUENCE: 23

| | |
|---|---|
| caggacgctg atgacgccct gattcagcgc ggtgcctacg tggcccgcct gtctgactgc | 60 |
| gttgcctgcc ataccgcact acacggccag cctttgctg gtggtctgga gatcaagagc | 120 |
| ccgatcggca cgatctactc caccaacatc acgcctgacc cgaaatacgg tatcggcaac | 180 |
| tatacactcg aagatttcac gaaggcgatc cgtaagggta tccgcaagga cggcgcgacg | 240 |
| gtttatccgg ccatgccgta tcctgagttc gctcgcctgt ctgatgacga catcaaggcc | 300 |
| atgtatgcct tcttcatgca tggcgtgaag ccggtcgccc ttcagaacaa gcagccggac | 360 |
| atctcctggc cgatgaacat cgctggccg ttggccatct ggcgcgcgat gtttgttccg | 420 |
| actgtcacac caggcctcga caagagcatc tccgatccgg aagtggcgcg tggcgaatac | 480 |
| ctcgtgaatg gccaggcca ttgtggcgag tgtcatacgc ccgtggcat ggccatgcag | 540 |
| gtcaagggct ataccggcaa ggacggcaac gcttacctct ccggtggcgc accgatcgac | 600 |
| aactggattc tcccagcct gcgtagcaat agcgacacgg gtctggtcg ctggtctgaa | 660 |
| gacgacattg ccgagttcct gaagagcggc cgtatcgacc attctgccgt cttcggtggc | 720 |
| atggctgacg tggtggccta cagcacccag cactggaccg acgacgatct gcacgcaacg | 780 |
| gccaagtacc tgaagagcat gccggccgtt ccggaaggca aaaacctggg tcaggatgac | 840 |
| ggcaaggcca cggccctgct cgaagccggt ggcaagggtg atgcaggcgc agaggtttac | 900 |
| ctccacaact gtgccatctg ccatatgaac gatggcactg tgtcaaccg catgttcccg | 960 |
| ccgctggctg gcaacccggt cgtcatcacg gacaatgcaa cctcaatggc caacatcgtg | 1020 |
| acattcggcg gtattctgcc tccgacgaat acggcgccat ctgctgttgc catgccgggc | 1080 |
| ttccgcgatc atctgtctga ccagcagatc gccgatgttg tgaacttcat gcgcaagagc | 1140 |

| | | | |
|---|---|---|---|
| tggggcaacc | aggctccggg | aaccctgtct | gcctcggata tccgcaagct ccgcacatcg | 1200 |
| ggtactgcgg | tttccacggc | cggctggaac | gtctcttcca agggctggat ggcctacatg | 1260 |
| ccgcagcctt | atggcgaagg | ctggaccttc | tccccgcaga cacacacggg cgtggatcag | 1320 |
| gctcagtaa | | | | 1329 |

<210> SEQ ID NO 24
<211> LENGTH: 843
<212> TYPE: DNA
<213> ORGANISM: Gluconobacter suboxydans

<400> SEQUENCE: 24

| | | | | |
|---|---|---|---|---|
| gctggaaccc | cgctgaaaat | tggcgtttcc | tttcaggaaa tgaacaatcc gtacttcgtc | 60 |
| accatgaagg | acgcattgca | ggaagccgct | ggcacgatcg gtgcgaatgt catcatcagt | 120 |
| gatgcgcatc | atgatgtttc | caagcaggtg | agtgacattg aggacatgat ccagcagggc | 180 |
| gcgcagatca | tcatcatcaa | cccgaccgat | acagtaggcg tcacgtccgt cgtaaagagc | 240 |
| gttcatgaca | agaacatccc | gatcgtctcg | gtggatgctc aggctggcgg tccgctcgat | 300 |
| gcgtttgtgg | ggtccaagaa | ctatgatgcc | ggcttcaagg cctgcgagta tctcgccacg | 360 |
| acgatcaaga | gcggcaatat | cggaatcatc | gacggtatcc cggtcgttcc cattcttgag | 420 |
| cgtgtcaaag | gctgcaaaaa | cgctatcgcc | aagcattcag atatcaagat tgtcagcgtt | 480 |
| cagaacggca | gcaggagcg | cgatgaggct | ctgacggtgg ctgaaaacat gctccaggcc | 540 |
| aacccggatc | tgaaaggtat | cttcagcgtc | aatgacaacg gatcgctcgg tgtgctgtcc | 600 |
| gctatcgaat | ccagtggttc | agacgtgaag | ctggtcagcg ttgatggcaa cccggaagcc | 660 |
| gtgaaggcca | tctacaagcc | aggctctcat | ttcatcgcta cggctgcgca gttccccgg | 720 |
| caggatatcc | gtctggcact | ggcgctcgcc | cttgccagga atggggcgc aggcgtgccg | 780 |
| aaggtcctgc | ctgttgatgt | cgagctgatc | gacgcgacga aagccaagac gttcagctgg | 840 |
| taa | | | | 843 |

<210> SEQ ID NO 25
<211> LENGTH: 720
<212> TYPE: PRT
<213> ORGANISM: Gluconobacter suboxydans

<400> SEQUENCE: 25

Glu Asp Thr Gly Thr Ala Ile Thr Asn Ala Asp Gln His Pro Gly Asp
 1               5                  10                  15

Trp Met Ser Tyr Gly Arg Thr Tyr Ser Glu Gln Arg Tyr Ser Pro Leu
            20                  25                  30

Asp Gln Ile Thr Lys Asp Asn Ala Ser Asn Leu Lys Leu Ala Trp His
        35                  40                  45

Tyr Asp Leu Asp Thr Asn Arg Gly Gln Glu Gly Thr Pro Leu Ile Val
    50                  55                  60

Asp Gly Val Met Tyr Ala Thr Thr Asn Trp Ser Lys Met Lys Ala Leu
65                  70                  75                  80

Asp Ala Ala Thr Gly Lys Leu Leu Trp Ser Tyr Asp Pro Lys Val Pro
                85                  90                  95

Gly Asn Ile Ala Asp Arg Gly Cys Cys Asp Thr Val Asn Arg Gly Ala
            100                 105                 110

Ala Tyr Trp Asn Gly Lys Val Tyr Phe Gly Thr Phe Asp Gly Arg Leu
        115                 120                 125

-continued

```
Ile Ala Leu Asp Ala Lys Thr Gly Lys Leu Val Trp Ser Val Tyr Thr
    130                 135                 140
Val Pro Lys Glu Ala Gln Leu Gly His Gln Arg Ser Tyr Thr Val Asp
145                 150                 155                 160
Gly Ala Pro Arg Ile Ala Lys Gly Lys Val Ile Ile Gly Asn Gly Gly
                165                 170                 175
Ala Glu Phe Gly Ala Arg Gly Phe Val Thr Ala Tyr Asp Ala Glu Thr
            180                 185                 190
Gly Lys Met Asp Trp Arg Phe Phe Thr Val Pro Asn Pro Asp Asn Lys
        195                 200                 205
Pro Asp Gly Ala Ala Ser Asp Asp Val Leu Met Ser Lys Ala Tyr Pro
    210                 215                 220
Thr Trp Gly Lys Gly Gly Ala Trp Lys Gln Gln Gly Gly Gly Gly Thr
225                 230                 235                 240
Val Trp Asp Ser Leu Ile Tyr Asp Pro Val Thr Asp Leu Val Tyr Leu
                245                 250                 255
Gly Val Gly Asn Gly Ser Pro Trp Asn Tyr Lys Phe Arg Ser Glu Gly
            260                 265                 270
Lys Gly Asn Asn Leu Phe Leu Gly Ser Ile Val Ala Ile Asn Pro Asp
        275                 280                 285
Thr Gly Lys Tyr Val Trp His Phe Gln Glu Thr Pro Met Asp Gln Trp
    290                 295                 300
Asp Tyr Thr Ser Val Gln Gln Ile Met Ala Leu Asp Met Pro Val Asn
305                 310                 315                 320
Gly Glu Met Arg His Val Leu Val His Ala Pro Lys Asn Gly Phe Phe
                325                 330                 335
Tyr Ile Ile Asp Ala Lys Thr Gly Lys Phe Ile Ser Gly Lys Pro Tyr
            340                 345                 350
Thr Tyr Glu Asn Trp Ala Asn Gly Leu Asp Pro Val Thr Gly Arg Pro
        355                 360                 365
Asn Tyr Asn Pro Asp Ala Leu Trp Thr Leu Asn Gly Lys Pro Trp Tyr
    370                 375                 380
Gly Ile Pro Gly Asp Leu Gly Gly His Asn Phe Ala Ala Met Ala Tyr
385                 390                 395                 400
Ser Pro Gln Thr Lys Leu Val Tyr Ile Pro Ala Gln Gln Val Pro Phe
                405                 410                 415
Val Tyr Asp Pro Gln Lys Gly Gly Phe Lys Ala His His Asp Ser Trp
            420                 425                 430
Asn Leu Gly Leu Asp Met Asn Lys Ile Gly Leu Leu Asp Asp Asn Asp
        435                 440                 445
Pro Gln His Lys Ala Asp Lys Ala Gln Phe Leu Lys Asp Leu Lys Gly
    450                 455                 460
Trp Ile Ala Trp Asp Pro Gln Lys Gln Ala Ala Phe Thr Val
465                 470                 475                 480
Asp His Lys Gly Pro Trp Asn Gly Gly Leu Leu Ala Thr Ala Gly Gly
                485                 490                 495
Val Leu Phe Gln Gly Leu Ala Asn Gly Glu Phe His Ala Tyr Asp Ala
            500                 505                 510
Thr Thr Gly Lys Asp Leu Phe Thr Phe Pro Ala Gln Ser Ala Ile Ile
        515                 520                 525
Ala Pro Pro Val Thr Tyr Thr Ala Asn Gly Lys Gln Tyr Val Ala Val
    530                 535                 540
Glu Val Gly Trp Gly Gly Ile Tyr Pro Phe Phe Leu Gly Gly Val Ala
```

-continued

```
545                 550                 555                 560
Arg Thr Ser Gly Trp Thr Val Asn His Ser Arg Ile Ile Ala Phe Ala
                565                 570                 575

Leu Asp Gly Asn Asp Lys Leu Pro Ala Lys Asn Glu Leu Gly Phe Val
                580                 585                 590

Pro Val Lys Pro Pro Glu Lys Trp Asp Glu Ala Lys Ile Lys Asp Gly
                595                 600                 605

Tyr Phe Gln Phe Gln Thr Tyr Cys Ala Ala Cys His Gly Asp Asn Gly
                610                 615                 620

Ile Ser Gly Gly Val Leu Pro Asp Leu Arg Trp Ser Gly Ala Ile Arg
625                 630                 635                 640

Gly Glu Glu Lys Phe Tyr Lys Leu Val Gly Lys Gly Ala Leu Thr Ala
                645                 650                 655

Tyr Gly Met Asp Arg Phe Asp Thr Ser Met Ser Pro Ala Glu Ile Glu
                660                 665                 670

Asp Ile Arg Asn Phe Leu Val Lys Arg Ala Asn Glu Ser Tyr Ala Asp
                675                 680                 685

Glu Val Lys Ala Arg Lys Asn Glu Ala Gly Val Pro Asn Gly Glu Phe
                690                 695                 700

Leu Asn Val Pro Gln Gly Ser Val Ala Pro Thr Pro Asp His Pro
705                 710                 715                 720

<210> SEQ ID NO 26
<211> LENGTH: 442
<212> TYPE: PRT
<213> ORGANISM: Gluconobacter suboxydans

<400> SEQUENCE: 26

Gln Asp Ala Asp Ala Leu Ile Gln Arg Gly Ala Tyr Val Ala Arg
 1               5                  10                  15

Leu Ser Asp Cys Val Ala Cys His Thr Ala Leu His Gly Gln Pro Phe
                20                  25                  30

Ala Gly Gly Leu Glu Ile Lys Ser Pro Ile Gly Thr Ile Tyr Ser Thr
                35                  40                  45

Asn Ile Thr Pro Asp Pro Lys Tyr Gly Ile Gly Asn Tyr Thr Leu Glu
        50                  55                  60

Asp Phe Thr Lys Ala Ile Arg Lys Gly Ile Arg Lys Asp Gly Ala Thr
65                  70                  75                  80

Val Tyr Pro Ala Met Pro Tyr Pro Glu Phe Ala Arg Leu Ser Asp Asp
                85                  90                  95

Asp Ile Lys Ala Met Tyr Ala Phe Phe Met His Gly Val Lys Pro Val
                100                 105                 110

Ala Leu Gln Asn Lys Gln Pro Asp Ile Ser Trp Pro Met Asn Met Arg
                115                 120                 125

Trp Pro Leu Ala Ile Trp Arg Ala Met Phe Val Pro Thr Val Thr Pro
            130                 135                 140

Gly Leu Asp Lys Ser Ile Ser Asp Pro Glu Val Ala Arg Gly Glu Tyr
145                 150                 155                 160

Leu Val Asn Gly Pro Gly His Cys Gly Glu Cys His Thr Pro Arg Gly
                165                 170                 175

Met Ala Met Gln Val Lys Gly Tyr Thr Ala Lys Asp Gly Asn Ala Tyr
                180                 185                 190

Leu Ser Gly Gly Ala Pro Ile Asp Asn Trp Ile Ala Pro Ser Leu Arg
                195                 200                 205
```

```
Ser Asn Ser Asp Thr Gly Leu Gly Arg Trp Ser Glu Asp Asp Ile Ala
    210                 215                 220

Glu Phe Leu Lys Ser Gly Arg Ile Asp His Ser Ala Val Phe Gly Gly
225                 230                 235                 240

Met Ala Asp Val Val Ala Tyr Ser Thr Gln His Trp Thr Asp Asp Asp
                245                 250                 255

Leu His Ala Thr Ala Lys Tyr Leu Lys Ser Met Pro Ala Val Pro Glu
            260                 265                 270

Gly Lys Asn Leu Gly Gln Asp Asp Gly Lys Ala Thr Ala Leu Leu Glu
        275                 280                 285

Ala Gly Gly Lys Gly Asp Ala Gly Ala Glu Val Tyr Leu His Asn Cys
290                 295                 300

Ala Ile Cys His Met Asn Asp Gly Thr Gly Val Asn Arg Met Phe Pro
305                 310                 315                 320

Pro Leu Ala Gly Asn Pro Val Val Ile Thr Asp Asn Ala Thr Ser Met
                325                 330                 335

Ala Asn Ile Val Thr Phe Gly Gly Ile Leu Pro Pro Thr Asn Thr Ala
            340                 345                 350

Pro Ser Ala Val Ala Met Pro Gly Phe Arg Asp His Leu Ser Asp Gln
        355                 360                 365

Gln Ile Ala Asp Val Val Asn Phe Met Arg Lys Ser Trp Gly Asn Gln
370                 375                 380

Ala Pro Gly Thr Leu Ser Ala Ser Asp Ile Arg Lys Leu Arg Thr Ser
385                 390                 395                 400

Gly Thr Ala Val Ser Thr Ala Gly Trp Asn Val Ser Ser Lys Gly Trp
                405                 410                 415

Met Ala Tyr Met Pro Gln Pro Tyr Gly Glu Gly Trp Thr Phe Ser Pro
            420                 425                 430

Gln Thr His Thr Gly Val Asp Gln Ala Gln
        435                 440

<210> SEQ ID NO 27
<211> LENGTH: 280
<212> TYPE: PRT
<213> ORGANISM: Gluconobacter suboxydans

<400> SEQUENCE: 27

Ala Gly Thr Pro Leu Lys Ile Gly Val Ser Phe Gln Glu Met Asn Asn
1               5                   10                  15

Pro Tyr Phe Val Thr Met Lys Asp Ala Leu Gln Glu Ala Ala Gly Thr
                20                  25                  30

Ile Gly Ala Asn Val Ile Ile Ser Asp Ala His Asp Val Ser Lys
            35                  40                  45

Gln Val Ser Asp Ile Glu Asp Met Ile Gln Gln Gly Ala Gln Ile Ile
        50                  55                  60

Ile Ile Asn Pro Thr Asp Thr Val Gly Val Thr Ser Val Val Lys Ser
65                  70                  75                  80

Val His Asp Lys Asn Ile Pro Ile Val Ser Val Asp Ala Gln Ala Gly
                85                  90                  95

Gly Pro Leu Asp Ala Phe Val Gly Ser Lys Asn Tyr Asp Ala Gly Phe
            100                 105                 110

Lys Ala Cys Glu Tyr Leu Ala Thr Thr Ile Lys Ser Gly Asn Ile Gly
        115                 120                 125

Ile Ile Asp Gly Ile Pro Val Val Pro Ile Leu Glu Arg Val Lys Gly
130                 135                 140
```

```
Cys Lys Asn Ala Ile Ala Lys His Ser Asp Ile Lys Ile Val Ser Val
145                 150                 155                 160

Gln Asn Gly Lys Gln Glu Arg Asp Glu Ala Leu Thr Val Ala Glu Asn
            165                 170                 175

Met Leu Gln Ala Asn Pro Asp Leu Lys Gly Ile Phe Ser Val Asn Asp
        180                 185                 190

Asn Gly Ser Leu Gly Val Leu Ser Ala Ile Glu Ser Ser Gly Ser Asp
            195                 200                 205

Val Lys Leu Val Ser Val Asp Gly Asn Pro Glu Ala Val Lys Ala Ile
        210                 215                 220

Tyr Lys Pro Gly Ser His Phe Ile Ala Thr Ala Ala Gln Phe Pro Arg
225                 230                 235                 240

Gln Asp Ile Arg Leu Ala Leu Ala Leu Ala Leu Ala Arg Lys Trp Gly
                245                 250                 255

Ala Gly Val Pro Lys Val Leu Pro Val Asp Val Glu Leu Ile Asp Ala
            260                 265                 270

Thr Lys Ala Lys Thr Phe Ser Trp
        275                 280

<210> SEQ ID NO 28
<211> LENGTH: 664
<212> TYPE: DNA
<213> ORGANISM: Gluconobacter suboxydans

<400> SEQUENCE: 28
cgagaacgga agcccgctga aatcgacccg ttccccatca aaatactttt cgagaagatc      60
acgaaccttc accaggagcg gcgtctcttc ctgatcgcgc ccccaccccc aatcgagagc     120
aacaatacgc ccgtcatctt cactgatggt cagggctccg agatgggaat ggcaggaaag     180
ctgtggcata cagatacgct gccccatccc ccggaaagcg tcaatcatgc ttccctaaaa     240
gagtccctga gaaaaaaata catgcgtgtc acgcatatgc agggaggccg gtattctcaa     300
ataacatatg ggatcatttt tgtatgattt catgaaatat tacgcacttt gttgagaaac     360
tgccattttt tgtgtcaaac ctgcgacaga cactaaagct gttttggttg tttggttatt     420
aagaataatt ctcatgtaat taagcgagcg attttacgcg gatagtgctc acggagacgt     480
cagaagccca cgtttccgac aaacaataaa ataagcgagt agtaagttca cgcgatgcta     540
cgttttccag acgacttgga gaaactgagg agcacctagg cacccacaga ggcgcctatc     600
aggacttgga ttacgtctga ataccattaa caggaacagt ctttgcaaaa aggacagtcg     660
gatc                                                                 664

<210> SEQ ID NO 29
<211> LENGTH: 615
<212> TYPE: DNA
<213> ORGANISM: Gluconobacter suboxydans

<400> SEQUENCE: 29
tcgagaagat cacgaacctt caccaggagc ggcgtctctt cctgatcgcg ccccaccccc      60 aatcgagag caacaatacg cccgtcatct tcactgatgg tcagggctcc gagatgggaa     120
tggcaggaaa gctgtggcat acagatacgc tgccccatcc ccggaaagc gtcaatcatg     180 cttccctaaa agagtccctg agaaaaaaat acatgcgtgt cacgcatatg cagggaggcc     240
ggtattctca aataacatat gggatcattt ttgtatgatt tcatgaaata ttacgcactt     300
tgttgagaaa ctgccatttt ttgtgtcaaa cctgcgacag acactaaagc tgttttggtt     360
```

```
gtttggttat taagaataat tctcatgtaa ttaagcgagc gattttacgc ggatagtgct      420
cacggagacg tcagaagccc acgtttccga caaacaataa aataagcgag tagtaagttc      480
acgcgatgct acgttttcca gacgacttgg agaaactgag gagcacctag gcacccacag      540
aggcgcctat caggacttgg attacgtctg aataccatta acaggaacag tctttgcaaa      600
aaggacagtc ggatc                                                       615

<210> SEQ ID NO 30
<211> LENGTH: 565
<212> TYPE: DNA
<213> ORGANISM: Gluconobacter suboxydans

<400> SEQUENCE: 30
cccccacccc caatcgagag caacaatacg cccgtcatct tcactgatgg tcagggctcc       60
gagatgggaa tggcaggaaa gctgtggcat acagatacgc tgccccatcc cccggaaagc      120
gtcaatcatg cttccctaaa agagtccctg agaaaaaaat acatgcgtgt cacgcatatg      180
cagggaggcc ggtattctca aataacatat gggatcattt ttgtatgatt tcatgaaata      240
ttacgcactt tgttgagaaa ctgccatttt ttgtgtcaaa cctgcgacag acactaaagc      300
tgttttggtt gtttggttat taagaataat tctcatgtaa ttaagcgagc gattttacgc      360
ggatagtgct cacggagacg tcagaagccc acgtttccga caaacaataa aataagcgag      420
tagtaagttc acgcgatgct acgttttcca gacgacttgg agaaactgag gagcacctag      480
gcacccacag aggcgcctat caggacttgg attacgtctg aataccatta acaggaacag      540
tctttgcaaa aaggacagtc ggatc                                            565

<210> SEQ ID NO 31
<211> LENGTH: 515
<212> TYPE: DNA
<213> ORGANISM: Gluconobacter suboxydans

<400> SEQUENCE: 31
tcagggctcc gagatgggaa tggcaggaaa gctgtggcat acagatacgc tgccccatcc       60
cccggaaagc gtcaatcatg cttccctaaa agagtccctg agaaaaaaat acatgcgtgt      120
cacgcatatg cagggaggcc ggtattctca aataacatat gggatcattt ttgtatgatt      180
tcatgaaata ttacgcactt tgttgagaaa ctgccatttt ttgtgtcaaa cctgcgacag      240
acactaaagc tgttttggtt gtttggttat taagaataat tctcatgtaa ttaagcgagc      300
gattttacgc ggatagtgct cacggagacg tcagaagccc acgtttccga caaacaataa      360
aataagcgag tagtaagttc acgcgatgct acgttttcca gacgacttgg agaaactgag      420
gagcacctag gcacccacag aggcgcctat caggacttgg attacgtctg aataccatta      480
acaggaacag tctttgcaaa aaggacagtc ggatc                                 515

<210> SEQ ID NO 32
<211> LENGTH: 465
<212> TYPE: DNA
<213> ORGANISM: Gluconobacter suboxydans

<400> SEQUENCE: 32
tgccccatcc cccggaaagc gtcaatcatg cttccctaaa agagtccctg agaaaaaaat       60
acatgcgtgt cacgcatatg cagggaggcc ggtattctca aataacatat gggatcattt      120
ttgtatgatt tcatgaaata ttacgcactt tgttgagaaa ctgccatttt ttgtgtcaaa      180
```

```
cctgcgacag acactaaagc tgttttggtt gtttggttat taagaataat tctcatgtaa    240
ttaagcgagc gattttacgc ggatagtgct cacggagacg tcagaagccc acgtttccga    300
caaacaataa aataagcgag tagtaagttc acgcgatgct acgttttcca gacgacttgg    360
agaaactgag gagcacctag gcacccacag aggcgcctat caggacttgg attacgtctg    420
aataccatta acaggaacag tctttgcaaa aaggacagtc ggatc                    465

<210> SEQ ID NO 33
<211> LENGTH: 415
<212> TYPE: DNA
<213> ORGANISM: Gluconobacter suboxydans

<400> SEQUENCE: 33
agaaaaaaat acatgcgtgt cacgcatatg cagggaggcc ggtattctca aataacatat     60
gggatcattt ttgtatgatt tcatgaaata ttacgcactt tgttgagaaa ctgccatttt    120
ttgtgtcaaa cctgcgacag acactaaagc tgttttggtt gtttggttat taagaataat    180
tctcatgtaa ttaagcgagc gattttacgc ggatagtgct cacggagacg tcagaagccc    240
acgtttccga caaacaataa aataagcgag tagtaagttc acgcgatgct acgttttcca    300
gacgacttgg agaaactgag gagcacctag gcacccacag aggcgcctat caggacttgg    360
attacgtctg aataccatta acaggaacag tctttgcaaa aaggacagtc ggatc         415

<210> SEQ ID NO 34
<211> LENGTH: 365
<212> TYPE: DNA
<213> ORGANISM: Gluconobacter suboxydans

<400> SEQUENCE: 34
aataacatat gggatcattt ttgtatgatt tcatgaaata ttacgcactt tgttgagaaa     60
ctgccatttt ttgtgtcaaa cctgcgacag acactaaagc tgttttggtt gtttggttat    120
taagaataat tctcatgtaa ttaagcgagc gattttacgc ggatagtgct cacggagacg    180
tcagaagccc acgtttccga caaacaataa aataagcgag tagtaagttc acgcgatgct    240
acgttttcca gacgacttgg agaaactgag gagcacctag gcacccacag aggcgcctat    300
caggacttgg attacgtctg aataccatta acaggaacag tctttgcaaa aaggacagtc    360
ggatc                                                                365

<210> SEQ ID NO 35
<211> LENGTH: 315
<212> TYPE: DNA
<213> ORGANISM: Gluconobacter suboxydans

<400> SEQUENCE: 35
tgttgagaaa ctgccatttt ttgtgtcaaa cctgcgacag acactaaagc tgttttggtt     60
gtttggttat taagaataat tctcatgtaa ttaagcgagc gattttacgc ggatagtgct    120
cacggagacg tcagaagccc acgtttccga caaacaataa aataagcgag tagtaagttc    180
acgcgatgct acgttttcca gacgacttgg agaaactgag gagcacctag gcacccacag    240
aggcgcctat caggacttgg attacgtctg aataccatta acaggaacag tctttgcaaa    300
aaggacagtc ggatc                                                     315

<210> SEQ ID NO 36
<211> LENGTH: 265
<212> TYPE: DNA
<213> ORGANISM: Gluconobacter suboxydans
```

<400> SEQUENCE: 36

```
tgttttggtt gtttggttat taagaataat tctcatgtaa ttaagcgagc gattttacgc      60
ggatagtgct cacggagacg tcagaagccc acgtttccga caaacaataa aataagcgag     120
tagtaagttc acgcgatgct acgttttcca gacgacttgg agaaactgag gagcacctag     180
gcacccacag aggcgcctat caggacttgg attacgtctg aataccatta acaggaacag     240
tctttgcaaa aaggacagtc ggatc                                           265
```

<210> SEQ ID NO 37
<211> LENGTH: 215
<212> TYPE: DNA
<213> ORGANISM: Gluconobacter suboxydans

<400> SEQUENCE: 37

```
gattttacgc ggatagtgct cacggagacg tcagaagccc acgtttccga caaacaataa      60
aataagcgag tagtaagttc acgcgatgct acgttttcca gacgacttgg agaaactgag     120
gagcacctag gcacccacag aggcgcctat caggacttgg attacgtctg aataccatta     180
acaggaacag tctttgcaaa aaggacagtc ggatc                                215
```

<210> SEQ ID NO 38
<211> LENGTH: 165
<212> TYPE: DNA
<213> ORGANISM: Gluconobacter suboxydans

<400> SEQUENCE: 38

```
caaacaataa aataagcgag tagtaagttc acgcgatgct acgttttcca gacgacttgg      60
agaaactgag gagcacctag gcacccacag aggcgcctat caggacttgg attacgtctg     120
aataccatta acaggaacag tctttgcaaa aaggacagtc ggatc                     165
```

<210> SEQ ID NO 39
<211> LENGTH: 115
<212> TYPE: DNA
<213> ORGANISM: Gluconobacter suboxydans

<400> SEQUENCE: 39

```
gacgacttgg agaaactgag gagcacctag gcacccacag aggcgcctat caggacttgg      60
attacgtctg aataccatta acaggaacag tctttgcaaa aaggacagtc ggatc          115
```

<210> SEQ ID NO 40
<211> LENGTH: 65
<212> TYPE: DNA
<213> ORGANISM: Gluconobacter suboxydans

<400> SEQUENCE: 40

```
caggacttgg attacgtctg aataccatta acaggaacag tctttgcaaa aaggacagtc      60
ggatc                                                                  65
```

<210> SEQ ID NO 41
<211> LENGTH: 34
<212> TYPE: DNA
<213> ORGANISM: Gluconobacter suboxydans

<400> SEQUENCE: 41

```
cgggaaaccg tcacgctgaa aggaatgacg tgac                                  34
```

<210> SEQ ID NO 42

```
<211> LENGTH: 51
<212> TYPE: DNA
<213> ORGANISM: Gluconobacter suboxydans

<400> SEQUENCE: 42
gcctctccag accctgtcag tctgacagaa aagggcggtc cggatacggg c          51

<210> SEQ ID NO 43
<211> LENGTH: 101
<212> TYPE: DNA
<213> ORGANISM: Gluconobacter suboxydans

<400> SEQUENCE: 43
gcctctccag accctgtcag tctgacagaa aagggcggtc cggatacggg ccgccttttt  60
cttttgtatt caggccgttt tcacaggatg gcatcctgca c                    101

<210> SEQ ID NO 44
<211> LENGTH: 151
<212> TYPE: DNA
<213> ORGANISM: Gluconobacter suboxydans

<400> SEQUENCE: 44
gcctctccag accctgtcag tctgacagaa aagggcggtc cggatacggg ccgccttttt  60
cttttgtatt caggccgttt tcacaggatg gcatcctgca ctacatatga aggcatgact 120
cccttctcgt cttctgctcc gcagtcagtt t                               151

<210> SEQ ID NO 45
<211> LENGTH: 201
<212> TYPE: DNA
<213> ORGANISM: Gluconobacter suboxydans

<400> SEQUENCE: 45
gcctctccag accctgtcag tctgacagaa aagggcggtc cggatacggg ccgccttttt  60
cttttgtatt caggccgttt tcacaggatg gcatcctgca ctacatatga aggcatgact 120
cccttctcgt cttctgctcc gcagtcagtt tttcctttgg caacaggcgc aggccgcgca 180
gcattgccat catgcgcgcc a                                          201

<210> SEQ ID NO 46
<211> LENGTH: 251
<212> TYPE: DNA
<213> ORGANISM: Gluconobacter suboxydans

<400> SEQUENCE: 46
gcctctccag accctgtcag tctgacagaa aagggcggtc cggatacggg ccgccttttt  60
cttttgtatt caggccgttt tcacaggatg gcatcctgca ctacatatga aggcatgact 120
cccttctcgt cttctgctcc gcagtcagtt tttcctttgg caacaggcgc aggccgcgca 180
gcattgccat catgcgcgcc aggacccgga agcgccgagc ttctcaagag cctctgcggt 240
tcccttcctg a                                                     251

<210> SEQ ID NO 47
<211> LENGTH: 301
<212> TYPE: DNA
<213> ORGANISM: Gluconobacter suboxydans

<400> SEQUENCE: 47
gcctctccag accctgtcag tctgacagaa aagggcggtc cggatacggg ccgccttttt  60
cttttgtatt caggccgttt tcacaggatg gcatcctgca ctacatatga aggcatgact 120
```

```
ccctctcgt cttctgctcc gcagtcagtt tttccttttgg caacaggcgc aggccgcgca      180
gcattgccat catgcgcgcc aggacccgga agcgccgagc ttctcaagag cctctgcggt      240
tcccttcctg accctcgacg cgccacctgc gcagctgcgc catcaaggcg aagtgctgga      300
t                                                                     301
```

```
<210> SEQ ID NO 48
<211> LENGTH: 351
<212> TYPE: DNA
<213> ORGANISM: Gluconobacter suboxydans

<400> SEQUENCE: 48
gcctctccag accctgtcag tctgacagaa aagggcggtc cggatacggg ccgccttttt       60
cttttgtatt caggccgttt tcacaggatg gcatcctgca ctacatatga aggcatgact      120 ccctctcgt cttctgctcc gcagtcagtt tttccttttgg caacaggcgc aggccgcgca      180
gcattgccat catgcgcgcc aggacccgga agcgccgagc ttctcaagag cctctgcggt      240
tcccttcctg accctcgacg cgccacctgc gcagctgcgc catcaaggcg aagtgctgga      300
tcatgccgtg gttctctggc ttcctggacc gaaatcctac accggcgaag a              351
```

```
<210> SEQ ID NO 49
<211> LENGTH: 401
<212> TYPE: DNA
<213> ORGANISM: Gluconobacter suboxydans

<400> SEQUENCE: 49
gcctctccag accctgtcag tctgacagaa aagggcggtc cggatacggg ccgccttttt       60
cttttgtatt caggccgttt tcacaggatg gcatcctgca ctacatatga aggcatgact      120 ccctctcgt cttctgctcc gcagtcagtt tttccttttgg caacaggcgc aggccgcgca      180
gcattgccat catgcgcgcc aggacccgga agcgccgagc ttctcaagag cctctgcggt      240
tcccttcctg accctcgacg cgccacctgc gcagctgcgc catcaaggcg aagtgctgga      300
tcatgccgtg gttctctggc ttcctggacc gaaatcctac accggcgaag acgggtgtcg      360
aactccacct tcatgctgga cccgctgtta tcactcgcgt t                         401
```

```
<210> SEQ ID NO 50
<211> LENGTH: 430
<212> TYPE: DNA
<213> ORGANISM: Gluconobacter suboxydans

<400> SEQUENCE: 50
gcctctccag accctgtcag tctgacagaa aagggcggtc cggatacggg ccgccttttt       60
cttttgtatt caggccgttt tcacaggatg gcatcctgca ctacatatga aggcatgact      120 ccctctcgt cttctgctcc gcagtcagtt tttccttttgg caacaggcgc aggccgcgca      180
gcattgccat catgcgcgcc aggacccgga agcgccgagc ttctcaagag cctctgcggt      240
tcccttcctg accctcgacg cgccacctgc gcagctgcgc catcaaggcg aagtgctgga      300
tcatgccgtg gttctctggc ttcctggacc gaaatcctac accggcgaag acgggtgtcg      360
aactccacct tcatgctgga cccgctgtta tcactcgcgt tgcggatgct ctgaccgatc      420
tgggtgcacg                                                            430
```

```
<210> SEQ ID NO 51
<211> LENGTH: 1383
<212> TYPE: DNA
```

<213> ORGANISM: Gluconobacter suboxydans

<400> SEQUENCE: 51

| | | | | | |
|---|---|---|---|---|---|
| cgaagcgatc | gggacttttc | agggagccgg | gaagctggcc | gcctgtctgg | atcttctcgc | 60 |
| cacactgacg | tctgctccgt | tcaggacgct | gtccctcaaa | ggggagacca | aggctctcaa | 120 |
| cagcccggaa | atgcagcgga | taagcggtgt | catcacatcc | ctgatggcca | tggacccatc | 180 |
| cgaaatccgg | catgaccatc | tggcgcagga | tctgggcctc | tgcgcatcca | ccttctctcg | 240 |
| ccagttccgt | tctgcgacgg | gcgacacatt | catgtctttc | ctgcatcggc | tgcgggtgtg | 300 |
| tcacgcgtgc | catctgctgg | ccagttccac | actctcaatc | acggaaatcg | ggctgcttc | 360 |
| cggcttcaac | aacctgtcca | attttaaccg | catcttcctg | cgcctgcgtg | gctgcacgcc | 420 |
| acgggaatac | cgccgtcatg | cccgcgaaat | gacagccctt | tcgccgacag | acgccgcaga | 480 |
| tttcctgaac | tgaccgacaa | gggaaaacag | atcatgccaa | cacttccaca | acgttttcc | 540 |
| ctcgatggtc | gcaaagctct | tgtcacgggt | gcatcccgcg | ggcttggtgt | tacgatctgc | 600 |
| gacgttctga | gtgctgcggg | ggccgatatt | gtcgccgttg | cgcgttctga | aaccgacatg | 660 |
| gccgccacat | gccggatcgt | ggaaggccat | ggtcgtcaat | gcctcacggt | tgttgccgat | 720 |
| ctcagtgatc | cgatggctcc | ggacgctgtc | gcgcagacag | tgaacgcagc | gtggggtggg | 780 |
| gtggatattg | tcgtcaacaa | tgctggcgtc | agtttccctc | gccctctggt | ggaacagacc | 840 |
| gtcgaggagt | gggacaccgt | gcaggccatt | aacctgcgtg | cgccatggct | tctcgcccgt | 900 |
| gtcttcgctc | cgggcatgat | tgaacgcaag | cgtgggaaaa | tcatcaacat | cagttcccag | 960 |
| gccagctctg | tcgcgctgat | tgaccatggt | gcttacgtcg | catccaaggc | cggtctgaac | 1020 |
| ggtctcacca | aggtcatgac | ggcggaatgg | gcggctcata | acatacaggc | caatgccatc | 1080 |
| tgccccacag | tcgtctggac | gcccatgggt | gaacgcgtct | ggagcgttgg | gaacaagctg | 1140 |
| gaaaagctac | tggaaaagat | ccccgctggc | cgtgtcgcaa | caccggaaga | tgtcgcggat | 1200 |
| atagttctgt | atctcgcctc | cgacgcgtcg | agcatggtca | acgggcagga | aatatttgtc | 1260 |
| gatggcggat | acacagccct | ttaggccgcc | acatcttcaa | ataaagacat | gtgattttac | 1320 |
| ggttttaaca | aggccatgtg | cagggaatgg | cctgcgcatt | tcatgcagat | caacaggtgt | 1380 |
| aac | | | | | | 1383 |

<210> SEQ ID NO 52
<211> LENGTH: 1334
<212> TYPE: DNA
<213> ORGANISM: Gluconobacter suboxydans

<400> SEQUENCE: 52

| | | | | | |
|---|---|---|---|---|---|
| gatcttctcg | ccacactgac | gtctgctccg | ttcaggacgc | tgtccctcaa | agggagacc | 60 |
| aaggctctca | acagcccgga | aatgcagcgg | ataagcggtg | tcatcacatc | cctgatggcc | 120 |
| atggacccat | ccgaaatccg | gcatgaccat | ctggcgcagg | atctgggcct | ctgcgcatcc | 180 |
| accttctctc | gccagttccg | ttctgcgacg | ggcgacacat | tcatgtcttt | cctgcatcgg | 240 |
| ctgcgggtgt | gtcacgcgtg | ccatctgctg | gccagttcca | cactctcaat | cacggaaatc | 300 |
| ggggctgctt | ccggcttcaa | caacctgtcc | aattttaacc | gcatcttcct | gcgcctgcgt | 360 |
| ggctgcacgc | cacgggaata | ccgccgtcat | gcccgcgaaa | tgacagccct | tcgccgaca | 420 |
| gacgccgcag | atttcctgaa | ctgaccgaca | agggaaaaca | gatcatgcca | acacttccac | 480 |
| aacgttttc | cctcgatggt | cgcaaagctc | ttgtcacggg | tgcatcccgc | gggcttggtg | 540 |
| ttacgatctg | cgacgttctg | agtgctgcgg | gggccgatat | tgtcgccgtt | gcgcgttctg | 600 |

```
aaaccgacat ggccgccaca tgccggatcg tggaaggcca tggtcgtcaa tgcctcacgg      660
ttgttgccga tctcagtgat ccgatggctc cggacgctgt cgcgcagaca gtgaacgcag      720
cgtggggtgg ggtggatatt gtcgtcaaca atgctggcgt cagtttccct cgccctctgg      780
tggaacagac cgtcgaggag tgggacaccg tgcaggccat taacctgcgt gcgccatggc      840
ttctcgcccg tgtcttcgct ccgggcatga ttgaacgcaa gcgtgggaaa atcatcaaca      900
tcagttccca ggccagctct gtcgcgctga ttgaccatgg tgcttacgtc gcatccaagg      960
ccggtctgaa cggtctcacc aaggtcatga cggcggaatg ggcggctcat aacatacagg     1020
ccaatgccat ctgccccaca gtcgtctgga cgcccatggg tgaacgcgtc tggagcgttg     1080
ggaacaagct ggaaaagcta ctggaaaaga tccccgctgg ccgtgtcgca acaccggaag     1140
atgtcgcgga tatagttctg tatctcgcct ccgacgcgtc gagcatggtc aacgggcagg     1200
aaatatttgt cgatggcgga tacacagccc tttaggccgc cacatcttca aataaagaca     1260
tgtgatttta cggttttaac aaggccatgt gcagggaatg gcctgcgcat ttcatgcaga     1320
tcaacaggtg taac                                                       1334

<210> SEQ ID NO 53
<211> LENGTH: 1284
<212> TYPE: DNA
<213> ORGANISM: Gluconobacter suboxydans

<400> SEQUENCE: 53 agggagacc aaggctctca acagcccgga aatgcagcgg ataagcggtg tcatcacatc       60
cctgatggcc atggacccat ccgaaatccg gcatgaccat ctggcgcagg atctgggcct     120
ctgcgcatcc accttctctc gccagttccg ttctgcgacg ggcgacacat tcatgtcttt     180
cctgcatcgg ctgcgggtgt gtcacgcgtg ccatctgctg gccagttcca cactctcaat     240
cacggaaatc ggggctgctt ccggcttcaa caacctgtcc aattttaacc gcatcttcct     300
gcgcctgcgt ggctgcacgc cacgggaata ccgccgtcat gcccgcgaaa tgacagccct     360
ttcgccgaca gacgccgcag atttcctgaa ctgaccgaca agggaaaaca gatcatgcca     420
acacttccac aacgttttc cctcgatggt cgcaaagctc ttgtcacggg tgcatcccgc      480
gggcttggtg ttacgatctg cgacgttctg agtgctgcgg gggccgatat tgtcgccgtt     540
gcgcgttctg aaaccgacat ggccgccaca tgccggatcg tggaaggcca tggtcgtcaa     600
tgcctcacgg ttgttgccga tctcagtgat ccgatggctc cggacgctgt cgcgcagaca     660
gtgaacgcag cgtggggtgg ggtggatatt gtcgtcaaca atgctggcgt cagtttccct     720
cgccctctgg tggaacagac cgtcgaggag tgggacaccg tgcaggccat taacctgcgt     780
gcgccatggc ttctcgcccg tgtcttcgct ccgggcatga ttgaacgcaa gcgtgggaaa     840
atcatcaaca tcagttccca ggccagctct gtcgcgctga ttgaccatgg tgcttacgtc     900
gcatccaagg ccggtctgaa cggtctcacc aaggtcatga cggcggaatg ggcggctcat     960
aacatacagg ccaatgccat ctgccccaca gtcgtctgga cgcccatggg tgaacgcgtc    1020
tggagcgttg ggaacaagct ggaaaagcta ctggaaaaga tccccgctgg ccgtgtcgca    1080
acaccggaag atgtcgcgga tatagttctg tatctcgcct ccgacgcgtc gagcatggtc    1140
aacgggcagg aaatatttgt cgatggcgga tacacagccc tttaggccgc cacatcttca    1200
aataaagaca tgtgatttta cggttttaac aaggccatgt gcagggaatg gcctgcgcat    1260
ttcatgcaga tcaacaggtg taac                                           1284
```

<210> SEQ ID NO 54
<211> LENGTH: 1234
<212> TYPE: DNA
<213> ORGANISM: Gluconobacter suboxydans

<400> SEQUENCE: 54

```
tcatcacatc cctgatggcc atggacccat ccgaaatccg gcatgaccat ctggcgcagg     60
atctgggcct ctgcgcatcc accttctctc gccagttccg ttctgcgacg ggcgacacat    120
tcatgtcttt cctgcatcgg ctgcgggtgt gtcacgcgtg ccatctgctg ccagttcca    180
cactctcaat cacggaaatc ggggctgctt ccggcttcaa caacctgtcc aattttaacc    240
gcatcttcct gcgcctgcgt ggctgcacgc cacgggaata ccgccgtcat gcccgcgaaa    300
tgacagccct ttcgccgaca gacgccgcag atttcctgaa ctgaccgaca agggaaaaca    360
gatcatgcca acacttccac aacgtttttc cctcgatggt cgcaaagctc ttgtcacggg    420
tgcatcccgc gggcttggtg ttacgatctg cgacgttctg agtgctgcgg gggccgatat    480
tgtcgccgtt gcgcgttctg aaaccgacat ggccgccaca tgccggatcg tggaaggcca    540
tggtcgtcaa tgcctcacgg ttgttgccga tctcagtgat ccgatggctc cggacgctgt    600
cgcgcagaca gtgaacgcag cgtggggtgg ggtggatatt gtcgtcaaca atgctggcgt    660
cagtttccct cgccctctgg tggaacagac cgtcgaggag tgggacaccg tgcaggccat    720
taacctgcgt gcgccatggc ttctcgcccg tgtcttcgct ccgggcatga ttgaacgcaa    780
gcgtgggaaa atcatcaaca tcagttccca ggccagctct gtcgcgctga ttgaccatgg    840
tgcttacgtc gcatccaagg ccggtctgaa cggtctcacc aaggtcatga cggcggaatg    900
ggcggctcat aacatacagg ccaatgccat ctgccccaca gtcgtctgga cgcccatggg    960
tgaacgcgtc tggagcgttg ggaacaagct ggaaaagcta ctggaaaaga tccccgctgg   1020
ccgtgtcgca acaccggaag atgtcgcgga tatagttctg tatctcgcct ccgacgcgtc   1080
gagcatggtc aacgggcagg aaatatttgt cgatgcggga tacacagccc tttaggccgc   1140
cacatcttca aataaagaca tgtgatttta cggttttaac aaggccatgt gcagggaatg   1200
gcctgcgcat tcatgcagat caacaggtg taac                                1234
```

<210> SEQ ID NO 55
<211> LENGTH: 1184
<212> TYPE: DNA
<213> ORGANISM: Gluconobacter suboxydans

<400> SEQUENCE: 55

```
ctggcgcagg atctgggcct ctgcgcatcc accttctctc gccagttccg ttctgcgacg     60
ggcgacacat tcatgtcttt cctgcatcgg ctgcgggtgt gtcacgcgtg ccatctgctg    120
gccagttcca cactctcaat cacggaaatc ggggctgctt ccggcttcaa caacctgtcc    180
aattttaacc gcatcttcct gcgcctgcgt ggctgcacgc cacgggaata ccgccgtcat    240
gcccgcgaaa tgacagccct ttcgccgaca gacgccgcag atttcctgaa ctgaccgaca    300
agggaaaaca gatcatgcca acacttccac aacgtttttc cctcgatggt cgcaaagctc    360
ttgtcacggg tgcatcccgc gggcttggtg ttacgatctg cgacgttctg agtgctgcgg    420
gggccgatat tgtcgccgtt gcgcgttctg aaaccgacat ggccgccaca tgccggatcg    480
tggaaggcca tggtcgtcaa tgcctcacgg ttgttgccga tctcagtgat ccgatggctc    540
cggacgctgt cgcgcagaca gtgaacgcag cgtggggtgg ggtggatatt gtcgtcaaca    600
atgctggcgt cagtttccct cgccctctgg tggaacagac cgtcgaggag tgggacaccg    660
```

| | | | | |
|---|---|---|---|---|
| tgcaggccat | taacctgcgt | gcgccatggc | ttctcgcccg | tgtcttcgct |
| ccgggcatga | | | | 720 |
| ttgaacgcaa | gcgtgggaaa | atcatcaaca | tcagttccca | ggccagctct |
| gtcgcgctga | | | | 780 |
| ttgaccatgg | tgcttacgtc | gcatccaagg | ccggtctgaa | cggtctcacc |
| aaggtcatga | | | | 840 |
| cggcggaatg | ggcggctcat | aacatacagg | ccaatgccat | ctgccccaca |
| gtcgtctgga | | | | 900 |
| cgcccatggg | tgaacgcgtc | tggagcgttg | ggaacaagct | ggaaaagcta |
| ctggaaaaga | | | | 960 |
| tccccgctgg | ccgtgtcgca | acaccggaag | atgtcgcgga | tatagttctg |
| tatctcgcct | | | | 1020 |
| ccgacgcgtc | gagcatggtc | aacgggcagg | aaatatttgt | cgatggcgga |
| tacacagccc | | | | 1080 |
| tttaggccgc | cacatcttca | aataaagaca | tgtgatttta | cggttttaac |
| aaggccatgt | | | | 1140 |
| gcagggaatg | gcctgcgcat | ttcatgcaga | tcaacaggtg | taac | 1184 |

<210> SEQ ID NO 56
<211> LENGTH: 1134
<212> TYPE: DNA
<213> ORGANISM: Gluconobacter suboxydans

<400> SEQUENCE: 56

| | | | | |
|---|---|---|---|---|
| ttctgcgacg | ggcgacacat | tcatgtcttt | cctgcatcgg | ctgcgggtgt |
| gtcacgcgtg | | | | 60 |
| ccatctgctg | gccagttcca | cactctcaat | cacggaaatc | ggggctgctt |
| ccggcttcaa | | | | 120 |
| caacctgtcc | aattttaacc | gcatcttcct | gcgcctgcgt | ggctgcacgc |
| cacgggaata | | | | 180 |
| ccgccgtcat | gcccgcgaaa | tgacagccct | tcgccgaca | dacgccgcag |
| atttcctgaa | | | | 240 |
| ctgaccgaca | agggaaaaca | gatcatgcca | acacttccac | aacgttttc |
| cctcgatggt | | | | 300 |
| cgcaaagctc | ttgtcacggg | tgcatcccgc | gggcttggtg | ttacgatctg |
| cgacgttctg | | | | 360 |
| agtgctgcgg | gggccgatat | tgtcgccgtt | gcgcgttctg | aaaccgacat |
| ggccgccaca | | | | 420 |
| tgccggatcg | tggaaggcca | tggtcgtcaa | tgcctcacgg | ttgttgccga |
| tctcagtgat | | | | 480 |
| ccgatggctc | cggacgctgt | cgcgcagaca | gtgaacgcag | cgtggggtgg |
| ggtggatatt | | | | 540 |
| gtcgtcaaca | atgctggcgt | cagtttccct | cgccctctgg | tggaacagac |
| cgtcgaggag | | | | 600 |
| tgggacaccg | tgcaggccat | taacctgcgt | gcgccatggc | ttctcgcccg |
| tgtcttcgct | | | | 660 |
| ccgggcatga | ttgaacgcaa | gcgtgggaaa | atcatcaaca | tcagttccca |
| ggccagctct | | | | 720 |
| gtcgcgctga | ttgaccatgg | tgcttacgtc | gcatccaagg | ccggtctgaa |
| cggtctcacc | | | | 780 |
| aaggtcatga | cggcggaatg | ggcggctcat | aacatacagg | ccaatgccat |
| ctgccccaca | | | | 840 |
| gtcgtctgga | cgcccatggg | tgaacgcgtc | tggagcgttg | ggaacaagct |
| ggaaaagcta | | | | 900 |
| ctggaaaaga | tccccgctgg | ccgtgtcgca | acaccggaag | atgtcgcgga |
| tatagttctg | | | | 960 |
| tatctcgcct | ccgacgcgtc | gagcatggtc | aacgggcagg | aaatatttgt |
| cgatggcgga | | | | 1020 |
| tacacagccc | tttaggccgc | cacatcttca | aataaagaca | tgtgatttta |
| cggttttaac | | | | 1080 |
| aaggccatgt | gcagggaatg | gcctgcgcat | ttcatgcaga | tcaacaggtg | taac | 1134 |

<210> SEQ ID NO 57
<211> LENGTH: 1084
<212> TYPE: DNA
<213> ORGANISM: Gluconobacter suboxydans

<400> SEQUENCE: 57

| | | | | |
|---|---|---|---|---|
| gtcacgcgtg | ccatctgctg | gccagttcca | cactctcaat | cacggaaatc |
| ggggctgctt | | | | 60 |
| ccggcttcaa | caacctgtcc | aattttaacc | gcatcttcct | gcgcctgcgt |
| ggctgcacgc | | | | 120 |
| cacgggaata | ccgccgtcat | gcccgcgaaa | tgacagccct | tcgccgaca |
| dacgccgcag | | | | 180 |

-continued

```
atttcctgaa ctgaccgaca agggaaaaca gatcatgcca acacttccac aacgttttc       240 cctcgatggt cgcaaagctc ttgtcacggg tgcatcccgc gggcttggtg ttacgatctg      300
cgacgttctg agtgctgcgg gggccgatat tgtcgccgtt gcgcgttctg aaaccgacat      360
ggccgccaca tgccggatcg tggaaggcca tggtcgtcaa tgcctcacgg ttgttgccga      420
tctcagtgat ccgatggctc cggacgctgt cgcgcagaca gtgaacgcag cgtggggtgg      480
ggtggatatt gtcgtcaaca atgctggcgt cagtttccct cgccctctgg tggaacagac      540
cgtcgaggag tgggacaccg tgcaggccat taacctgcgt gcgccatggc ttctcgcccg      600
tgtcttcgct ccgggcatga ttgaacgcaa gcgtgggaaa atcatcaaca tcagttccca      660
ggccagctct gtcgcgctga ttgaccatgg tgcttacgtc gcatccaagg ccggtctgaa      720
cggtctcacc aaggtcatga cggcggaatg gcggctcat aacatacagg ccaatgccat       780
ctgccccaca gtcgtctgga cgcccatggg tgaacgcgtc tggagcgttg ggaacaagct      840
ggaaaagcta ctggaaaaga tccccgctgg ccgtgtcgca acaccggaag atgtcgcgga      900
tatagttctg tatctcgcct ccgacgcgtc gagcatggtc aacgggcagg aaatatttgt      960
cgatggcgga tacacagccc tttaggccgc cacatcttca aataaagaca tgtgatttta     1020
cggttttaac aaggccatgt gcagggaatg gcctgcgcat ttcatgcaga tcaacaggtg     1080
taac                                                                  1084
```

<210> SEQ ID NO 58
<211> LENGTH: 1034
<212> TYPE: DNA
<213> ORGANISM: Gluconobacter suboxydans

<400> SEQUENCE: 58

```
ggggctgctt ccggcttcaa caacctgtcc aattttaacc gcatcttcct gcgcctgcgt       60
ggctgcacgc cacgggaata ccgccgtcat gcccgcgaaa tgacagccct ttcgccgaca      120
gacgccgcag atttcctgaa ctgaccgaca agggaaaaca gatcatgcca acacttccac      180 aacgttttc cctcgatggt cgcaaagctc ttgtcacggg tgcatcccgc gggcttggtg       240
ttacgatctg cgacgttctg agtgctgcgg gggccgatat tgtcgccgtt gcgcgttctg      300
aaaccgacat ggccgccaca tgccggatcg tggaaggcca tggtcgtcaa tgcctcacgg      360
ttgttgccga tctcagtgat ccgatggctc cggacgctgt cgcgcagaca gtgaacgcag      420
cgtggggtgg ggtggatatt gtcgtcaaca atgctggcgt cagtttccct cgccctctgg      480
tggaacagac cgtcgaggag tgggacaccg tgcaggccat taacctgcgt gcgccatggc      540
ttctcgcccg tgtcttcgct ccgggcatga ttgaacgcaa gcgtgggaaa atcatcaaca      600
tcagttccca ggccagctct gtcgcgctga ttgaccatgg tgcttacgtc gcatccaagg      660
ccggtctgaa cggtctcacc aaggtcatga cggcggaatg gcggctcat aacatacagg       720 ccaatgccat ctgccccaca gtcgtctgga cgcccatggg tgaacgcgtc tggagcgttg      780
ggaacaagct ggaaaagcta ctggaaaaga tccccgctgg ccgtgtcgca acaccggaag      840
atgtcgcgga tatagttctg tatctcgcct ccgacgcgtc gagcatggtc aacgggcagg      900
aaatatttgt cgatggcgga tacacagccc tttaggccgc cacatcttca aataaagaca      960
tgtgatttta cggttttaac aaggccatgt gcagggaatg gcctgcgcat ttcatgcaga     1020
tcaacaggtg taac                                                       1034
```

<210> SEQ ID NO 59
<211> LENGTH: 984

```
<212> TYPE: DNA
<213> ORGANISM: Gluconobacter suboxydans

<400> SEQUENCE: 59
gcgcctgcgt ggctgcacgc cacgggaata ccgccgtcat gcccgcgaaa tgacagccct      60
ttcgccgaca gacgccgcag atttcctgaa ctgaccgaca agggaaaaca gatcatgcca     120
acacttccac aacgtttttc cctcgatggt cgcaaagctc ttgtcacggg tgcatcccgc     180
gggcttggtg ttacgatctg cgacgttctg agtgctgcgg gggccgatat tgtcgccgtt     240
gcgcgttctg aaaccgacat ggccgccaca tgccggatcg tggaaggcca tggtcgtcaa     300
tgcctcacgg ttgttgccga tctcagtgat ccgatggctc cggacgctgt cgcgcagaca     360
gtgaacgcag cgtggggtgg ggtggatatt gtcgtcaaca atgctggcgt cagtttccct     420
cgccctctgg tggaacagac cgtcgaggag tgggacaccg tgcaggccat taacctgcgt     480
gcgccatggc ttctcgcccg tgtcttcgct ccgggcatga ttgaacgcaa gcgtgggaaa     540
atcatcaaca tcagttccca ggccagctct gtcgcgctga ttgaccatgg tgcttacgtc     600
gcatccaagg ccgtctgaa cggtctcacc aaggtcatga cggcggaatg ggcggctcat     660
aacatacagg ccaatgccat ctgccccaca gtcgtctgga cgcccatggg tgaacgcgtc     720
tggagcgttg ggaacaagct ggaaaagcta ctggaaaaga tccccgctgg ccgtgtcgca     780
acaccggaag atgtcgcgga tatagttctg tatctcgcct ccgacgcgtc gagcatggtc     840
aacgggcagg aaatatttgt cgatggcgga tacacagccc tttaggccgc cacatcttca     900
aataaagaca tgtgatttta cggttttaac aaggccatgt gcagggaatg gcctgcgcat     960
ttcatgcaga tcaacaggtg taac                                            984

<210> SEQ ID NO 60
<211> LENGTH: 934
<212> TYPE: DNA
<213> ORGANISM: Gluconobacter suboxydans

<400> SEQUENCE: 60
tgacagccct ttcgccgaca gacgccgcag atttcctgaa ctgaccgaca agggaaaaca      60
gatcatgcca acacttccac aacgtttttc cctcgatggt cgcaaagctc ttgtcacggg     120
tgcatcccgc gggcttggtg ttacgatctg cgacgttctg agtgctgcgg gggccgatat     180
tgtcgccgtt gcgcgttctg aaaccgacat ggccgccaca tgccggatcg tggaaggcca     240
tggtcgtcaa tgcctcacgg ttgttgccga tctcagtgat ccgatggctc cggacgctgt     300
cgcgcagaca gtgaacgcag cgtggggtgg ggtggatatt gtcgtcaaca atgctggcgt     360
cagtttccct cgccctctgg tggaacagac cgtcgaggag tgggacaccg tgcaggccat     420
taacctgcgt gcgccatggc ttctcgcccg tgtcttcgct ccgggcatga ttgaacgcaa     480
gcgtgggaaa atcatcaaca tcagttccca ggccagctct gtcgcgctga ttgaccatgg     540
tgcttacgtc gcatccaagg ccgtctgaa cggtctcacc aaggtcatga cggcggaatg     600
ggcggctcat aacatacagg ccaatgccat ctgccccaca gtcgtctgga cgcccatggg     660
tgaacgcgtc tggagcgttg ggaacaagct ggaaaagcta ctggaaaaga tccccgctgg     720
ccgtgtcgca acaccggaag atgtcgcgga tatagttctg tatctcgcct ccgacgcgtc     780
gagcatggtc aacgggcagg aaatatttgt cgatggcgga tacacagccc tttaggccgc     840
cacatcttca aataaagaca tgtgatttta cggttttaac aaggccatgt gcagggaatg     900
gcctgcgcat ttcatgcaga tcaacaggtg taac                                 934
```

<210> SEQ ID NO 61
<211> LENGTH: 884
<212> TYPE: DNA
<213> ORGANISM: Gluconobacter suboxydans

<400> SEQUENCE: 61

| | | | | | |
|---|---|---|---|---|---|
| agggaaaaca | gatcatgcca | acacttccac | aacgtttttc | cctcgatggt | cgcaaagctc | 60 |
| ttgtcacggg | tgcatcccgc | gggcttggtg | ttacgatctg | cgacgttctg | agtgctgcgg | 120 |
| gggccgatat | tgtcgccgtt | gcgcgttctg | aaaccgacat | ggccgccaca | tgccggatcg | 180 |
| tggaaggcca | tggtcgtcaa | tgcctcacgg | ttgttgccga | tctcagtgat | ccgatggctc | 240 |
| cggacgctgt | cgcgcagaca | gtgaacgcag | cgtggggtgg | ggtggatatt | gtcgtcaaca | 300 |
| atgctggcgt | cagtttccct | cgccctctgg | tggaacagac | cgtcgaggag | tgggacaccg | 360 |
| tgcaggccat | taacctgcgt | gcgccatggc | ttctcgcccg | tgtcttcgct | ccgggcatga | 420 |
| ttgaacgcaa | gcgtgggaaa | atcatcaaca | tcagttccca | ggccagctct | gtcgcgctga | 480 |
| ttgaccatgg | tgcttacgtc | gcatccaagg | ccggtctgaa | cggtctcacc | aaggtcatga | 540 |
| cggcggaatg | ggcggctcat | aacatacagg | ccaatgccat | ctgccccaca | gtcgtctgga | 600 |
| cgcccatggg | tgaacgcgtc | tggagcgttg | gaacaagct | ggaaaagcta | ctggaaaaga | 660 |
| tccccgctgg | ccgtgtcgca | acaccggaag | atgtcgcgga | tatagttctg | tatctcgcct | 720 |
| ccgacgcgtc | gagcatggtc | aacgggcagg | aaatatttgt | cgatggcgga | tacacagccc | 780 |
| tttaggccgc | cacatcttca | aataaagaca | tgtgatttta | cggttttaac | aaggccatgt | 840 |
| gcagggaatg | gcctgcgcat | tcatgcaga | tcaacaggtg | taac | | 884 |

<210> SEQ ID NO 62
<211> LENGTH: 834
<212> TYPE: DNA
<213> ORGANISM: Gluconobacter suboxydans

<400> SEQUENCE: 62

| | | | | | |
|---|---|---|---|---|---|
| cgcaaagctc | ttgtcacggg | tgcatcccgc | gggcttggtg | ttacgatctg | cgacgttctg | 60 |
| agtgctgcgg | gggccgatat | tgtcgccgtt | gcgcgttctg | aaaccgacat | ggccgccaca | 120 |
| tgccggatcg | tggaaggcca | tggtcgtcaa | tgcctcacgg | ttgttgccga | tctcagtgat | 180 |
| ccgatggctc | cggacgctgt | cgcgcagaca | gtgaacgcag | cgtggggtgg | ggtggatatt | 240 |
| gtcgtcaaca | atgctggcgt | cagtttccct | cgccctctgg | tggaacagac | cgtcgaggag | 300 |
| tgggacaccg | tgcaggccat | taacctgcgt | gcgccatggc | ttctcgcccg | tgtcttcgct | 360 |
| ccgggcatga | ttgaacgcaa | gcgtgggaaa | atcatcaaca | tcagttccca | ggccagctct | 420 |
| gtcgcgctga | ttgaccatgg | tgcttacgtc | gcatccaagg | ccggtctgaa | cggtctcacc | 480 |
| aaggtcatga | cggcggaatg | ggcggctcat | aacatacagg | ccaatgccat | ctgccccaca | 540 |
| gtcgtctgga | cgcccatggg | tgaacgcgtc | tggagcgttg | gaacaagct | ggaaaagcta | 600 |
| ctggaaaaga | tccccgctgg | ccgtgtcgca | acaccggaag | atgtcgcgga | tatagttctg | 660 |
| tatctcgcct | ccgacgcgtc | gagcatggtc | aacgggcagg | aaatatttgt | cgatggcgga | 720 |
| tacacagccc | tttaggccgc | cacatcttca | aataaagaca | tgtgatttta | cggttttaac | 780 |
| aaggccatgt | gcagggaatg | gcctgcgcat | tcatgcaga | tcaacaggtg | taac | 834 |

<210> SEQ ID NO 63
<211> LENGTH: 784
<212> TYPE: DNA
<213> ORGANISM: Gluconobacter suboxydans

<400> SEQUENCE: 63

```
cgacgttctg agtgctgcgg gggccgatat tgtcgccgtt gcgcgttctg aaaccgacat      60
ggccgccaca tgccggatcg tggaaggcca tggtcgtcaa tgcctcacgg ttgttgccga     120
tctcagtgat ccgatggctc cggacgctgt cgcgcagaca gtgaacgcag cgtggggtgg    180
ggtggatatt gtcgtcaaca atgctggcgt cagtttccct cgccctctgg tggaacagac    240
cgtcgaggag tgggacaccg tgcaggccat taacctgcgt gcgccatggc ttctcgcccg    300
tgtcttcgct ccgggcatga ttgaacgcaa gcgtgggaaa atcatcaaca tcagttccca    360
ggccagctct gtcgcgctga ttgaccatgg tgcttacgtc gcatccaagg ccggtctgaa    420
cggtctcacc aaggtcatga cggcggaatg ggcggctcat aacatacagg ccaatgccat    480
ctgccccaca gtcgtctgga cgcccatggg tgaacgcgtc tggagcgttg gaacaagct    540
ggaaaagcta ctggaaaaga tccccgctgg ccgtgtcgca acaccggaag atgtcgcgga    600
tatagttctg tatctcgcct ccgacgcgtc gagcatggtc aacgggcagg aaatatttgt    660
cgatggcgga tacacagccc tttaggccgc cacatcttca aataaagaca tgtgatttta    720
cggttttaac aaggccatgt gcagggaatg gcctgcgcat ttcatgcaga tcaacaggtg    780
taac                                                                 784
```

<210> SEQ ID NO 64
<211> LENGTH: 784
<212> TYPE: DNA
<213> ORGANISM: Gluconobacter suboxydans

<400> SEQUENCE: 64

```
cgacgttctg agtgctgcgg gggccgatat tgtcgccgtt gcgcgttctg aaaccgacat     60
ggccgccaca tgccggatcg tggaaggcca tggtcgtcaa tgcctcacgg ttgttgccga    120
tctcagtgat ccgatggctc cggacgctgt cgcgcagaca gtgaacgcag cgtggggtgg    180
ggtggatatt gtcgtcaaca atgctggcgt cagtttccct cgccctctgg tggaacagac    240
cgtcgaggag tgggacaccg tgcaggccat taacctgcgt gcgccatggc ttctcgcccg    300
tgtcttcgct ccgggcatga ttgaacgcaa gcgtgggaaa atcatcaaca tcagttccca    360
ggccagctct gtcgcgctga ttgaccatgg tgcttacgtc gcatccaagg ccggtctgaa    420
cggtctcacc aaggtcatga cggcggaatg ggcggctcat aacatacagg ccaatgccat    480
ctgccccaca gtcgtctgga cgcccatggg tgaacgcgtc tggagcgttg gaacaagct    540
ggaaaagcta ctggaaaaga tccccgctgg ccgtgtcgca acaccggaag atgtcgcgga    600
tatagttctg tatctcgcct ccgacgcgtc gagcatggtc aacgggcagg aaatatttgt    660
cgatggcgga tacacagccc tttaggccgc cacatcttca aataaagaca tgtgatttta    720
cggttttaac aaggccatgt gcagggaatg gcctgcgcat ttcatgcaga tcaacaggtg    780
taac                                                                 784
```

<210> SEQ ID NO 65
<211> LENGTH: 734
<212> TYPE: DNA
<213> ORGANISM: Gluconobacter suboxydans

<400> SEQUENCE: 65

```
aaaccgacat ggccgccaca tgccggatcg tggaaggcca tggtcgtcaa tgcctcacgg     60
ttgttgccga tctcagtgat ccgatggctc cggacgctgt cgcgcagaca gtgaacgcag    120
```

-continued

| | |
|---|---|
| cgtggggtgg ggtggatatt gtcgtcaaca atgctggcgt cagtttccct cgccctctgg | 180 |
| tggaacagac cgtcgaggag tgggacaccg tgcaggccat taacctgcgt gcgccatggc | 240 |
| ttctcgcccg tgtcttcgct ccgggcatga ttgaacgcaa gcgtgggaaa atcatcaaca | 300 |
| tcagttccca ggccagctct gtcgcgctga ttgaccatgg tgcttacgtc gcatccaagg | 360 |
| ccggtctgaa cggtctcacc aaggtcatga cggcggaatg ggcggctcat aacatacagg | 420 |
| ccaatgccat ctgccccaca gtcgtctgga cgcccatggg tgaacgcgtc tggagcgttg | 480 |
| ggaacaagct ggaaaagcta ctggaaaaga tccccgctgg ccgtgtcgca acaccggaag | 540 |
| atgtcgcgga tatagttctg tatctcgcct ccgacgcgtc gagcatggtc aacgggcagg | 600 |
| aaatatttgt cgatggcgga tacacagccc tttaggccgc cacatcttca aataaagaca | 660 |
| tgtgatttta cggttttaac aaggccatgt gcagggaatg gcctgcgcat ttcatgcaga | 720 |
| tcaacaggtg taac | 734 |

<210> SEQ ID NO 66
<211> LENGTH: 684
<212> TYPE: DNA
<213> ORGANISM: Gluconobacter suboxydans

<400> SEQUENCE: 66

| | |
|---|---|
| tgcctcacgg ttgttgccga tctcagtgat ccgatggctc cggacgctgt cgcgcagaca | 60 |
| gtgaacgcag cgtggggtgg ggtggatatt gtcgtcaaca atgctggcgt cagtttccct | 120 |
| cgccctctgg tggaacagac cgtcgaggag tgggacaccg tgcaggccat taacctgcgt | 180 |
| gcgccatggc ttctcgcccg tgtcttcgct ccgggcatga ttgaacgcaa gcgtgggaaa | 240 |
| atcatcaaca tcagttccca ggccagctct gtcgcgctga ttgaccatgg tgcttacgtc | 300 |
| gcatccaagg ccggtctgaa cggtctcacc aaggtcatga cggcggaatg ggcggctcat | 360 |
| aacatacagg ccaatgccat ctgccccaca gtcgtctgga cgcccatggg tgaacgcgtc | 420 |
| tggagcgttg ggaacaagct ggaaaagcta ctggaaaaga tccccgctgg ccgtgtcgca | 480 |
| acaccggaag atgtcgcgga tatagttctg tatctcgcct ccgacgcgtc gagcatggtc | 540 |
| aacgggcagg aaatatttgt cgatggcgga tacacagccc tttaggccgc cacatcttca | 600 |
| aataaagaca tgtgatttta cggttttaac aaggccatgt gcagggaatg gcctgcgcat | 660 |
| ttcatgcaga tcaacaggtg taac | 684 |

<210> SEQ ID NO 67
<211> LENGTH: 634
<212> TYPE: DNA
<213> ORGANISM: Gluconobacter suboxydans

<400> SEQUENCE: 67

| | |
|---|---|
| cgcgcagaca gtgaacgcag cgtggggtgg ggtggatatt gtcgtcaaca atgctggcgt | 60 |
| cagtttccct cgccctctgg tggaacagac cgtcgaggag tgggacaccg tgcaggccat | 120 |
| taacctgcgt gcgccatggc ttctcgcccg tgtcttcgct ccgggcatga ttgaacgcaa | 180 |
| gcgtgggaaa atcatcaaca tcagttccca ggccagctct gtcgcgctga ttgaccatgg | 240 |
| tgcttacgtc gcatccaagg ccggtctgaa cggtctcacc aaggtcatga cggcggaatg | 300 |
| ggcggctcat aacatacagg ccaatgccat ctgccccaca gtcgtctgga cgcccatggg | 360 |
| tgaacgcgtc tggagcgttg ggaacaagct ggaaaagcta ctggaaaaga tccccgctgg | 420 |
| ccgtgtcgca acaccggaag atgtcgcgga tatagttctg tatctcgcct ccgacgcgtc | 480 |
| gagcatggtc aacgggcagg aaatatttgt cgatggcgga tacacagccc tttaggccgc | 540 | cacatcttca aataaagaca tgtgatttta cggtttaac aaggccatgt gcagggaatg    600 gcctgcgcat tcatgcaga tcaacaggtg taac                               634

<210> SEQ ID NO 68
<211> LENGTH: 584
<212> TYPE: DNA
<213> ORGANISM: Gluconobacter suboxydans

<400> SEQUENCE: 68
atgctggcgt cagtttccct cgccctctgg tggaacagac cgtcgaggag tgggacaccg    60
tgcaggccat taacctgcgt gcgccatggc ttctcgcccg tgtcttcgct ccgggcatga   120
ttgaacgcaa gcgtgggaaa atcatcaaca tcagttccca ggccagctct gtcgcgctga   180
ttgaccatgg tgcttacgtc gcatccaagg ccggtctgaa cggtctcacc aaggtcatga   240
cggcggaatg ggcggctcat aacatacagg ccaatgccat ctgccccaca gtcgtctgga   300
cgcccatggg tgaacgcgtc tggagcgttg ggaacaagct ggaaaagcta ctggaaaaga   360
tccccgctgg ccgtgtcgca acaccggaag atgtcgcgga tatagttctg tatctcgcct   420
ccgacgcgtc gagcatggtc aacgggcagg aaatatttgt cgatggcgga tacacagccc   480
tttaggccgc cacatcttca aataaagaca tgtgatttta cggtttaac aaggccatgt   540 gcagggaatg gcctgcgcat tcatgcaga tcaacaggtg taac                    584

<210> SEQ ID NO 69
<211> LENGTH: 534
<212> TYPE: DNA
<213> ORGANISM: Gluconobacter suboxydans

<400> SEQUENCE: 69
tgggacaccg tgcaggccat taacctgcgt gcgccatggc ttctcgcccg tgtcttcgct    60
ccgggcatga ttgaacgcaa gcgtgggaaa atcatcaaca tcagttccca ggccagctct   120
gtcgcgctga ttgaccatgg tgcttacgtc gcatccaagg ccggtctgaa cggtctcacc   180
aaggtcatga cggcggaatg ggcggctcat aacatacagg ccaatgccat ctgccccaca   240
gtcgtctgga cgcccatggg tgaacgcgtc tggagcgttg ggaacaagct ggaaaagcta   300
ctggaaaaga tccccgctgg ccgtgtcgca acaccggaag atgtcgcgga tatagttctg   360
tatctcgcct ccgacgcgtc gagcatggtc aacgggcagg aaatatttgt cgatggcgga   420
tacacagccc tttaggccgc cacatcttca aataaagaca tgtgatttta cggtttaac   480 aaggccatgt gcagggaatg gcctgcgcat tcatgcaga tcaacaggtg taac         534

<210> SEQ ID NO 70
<211> LENGTH: 484
<212> TYPE: DNA
<213> ORGANISM: Gluconobacter suboxydans

<400> SEQUENCE: 70
tgtcttcgct ccgggcatga ttgaacgcaa gcgtgggaaa atcatcaaca tcagttccca    60
ggccagctct gtcgcgctga ttgaccatgg tgcttacgtc gcatccaagg ccggtctgaa   120
cggtctcacc aaggtcatga cggcggaatg ggcggctcat aacatacagg ccaatgccat   180
ctgccccaca gtcgtctgga cgcccatggg tgaacgcgtc tggagcgttg ggaacaagct   240
ggaaaagcta ctggaaaaga tccccgctgg ccgtgtcgca acaccggaag atgtcgcgga   300
tatagttctg tatctcgcct ccgacgcgtc gagcatggtc aacgggcagg aaatatttgt   360

-continued

| | |
|---|---|
| cgatggcgga tacacagccc tttaggccgc cacatcttca aataaagaca tgtgatttta | 420 |
| cggttttaac aaggccatgt gcagggaatg gcctgcgcat ttcatgcaga tcaacaggtg | 480 |
| taac | 484 |

<210> SEQ ID NO 71
<211> LENGTH: 434
<212> TYPE: DNA
<213> ORGANISM: Gluconobacter suboxydans

<400> SEQUENCE: 71

| | |
|---|---|
| tcagttccca ggccagctct gtcgcgctga ttgaccatgg tgcttacgtc gcatccaagg | 60 |
| ccggtctgaa cggtctcacc aaggtcatga cggcggaatg ggcggctcat aacatacagg | 120 |
| ccaatgccat ctgccccaca gtcgtctgga cgcccatggg tgaacgcgtc tggagcgttg | 180 |
| ggaacaagct ggaaaagcta ctggaaaaga tccccgctgg ccgtgtcgca acaccggaag | 240 |
| atgtcgcgga tatagttctg tatctcgcct ccgacgcgtc gagcatggtc aacgggcagg | 300 |
| aaatatttgt cgatggcgga tacacagccc tttaggccgc cacatcttca aataaagaca | 360 |
| tgtgatttta cggttttaac aaggccatgt gcagggaatg gcctgcgcat ttcatgcaga | 420 |
| tcaacaggtg taac | 434 |

<210> SEQ ID NO 72
<211> LENGTH: 384
<212> TYPE: DNA
<213> ORGANISM: Gluconobacter suboxydans

<400> SEQUENCE: 72

| | |
|---|---|
| gcatccaagg ccggtctgaa cggtctcacc aaggtcatga cggcggaatg ggcggctcat | 60 |
| aacatacagg ccaatgccat ctgccccaca gtcgtctgga cgcccatggg tgaacgcgtc | 120 |
| tggagcgttg ggaacaagct ggaaaagcta ctggaaaaga tccccgctgg ccgtgtcgca | 180 |
| acaccggaag atgtcgcgga tatagttctg tatctcgcct ccgacgcgtc gagcatggtc | 240 |
| aacgggcagg aaatatttgt cgatggcgga tacacagccc tttaggccgc cacatcttca | 300 |
| aataaagaca tgtgatttta cggttttaac aaggccatgt gcagggaatg gcctgcgcat | 360 |
| ttcatgcaga tcaacaggtg taac | 384 |

<210> SEQ ID NO 73
<211> LENGTH: 334
<212> TYPE: DNA
<213> ORGANISM: Gluconobacter suboxydans

<400> SEQUENCE: 73

| | |
|---|---|
| ggcggctcat aacatacagg ccaatgccat ctgccccaca gtcgtctgga cgcccatggg | 60 |
| tgaacgcgtc tggagcgttg ggaacaagct ggaaaagcta ctggaaaaga tccccgctgg | 120 |
| ccgtgtcgca acaccggaag atgtcgcgga tatagttctg tatctcgcct ccgacgcgtc | 180 |
| gagcatggtc aacgggcagg aaatatttgt cgatggcgga tacacagccc tttaggccgc | 240 |
| cacatcttca aataaagaca tgtgatttta cggttttaac aaggccatgt gcagggaatg | 300 |
| gcctgcgcat ttcatgcaga tcaacaggtg taac | 334 |

<210> SEQ ID NO 74
<211> LENGTH: 284
<212> TYPE: DNA
<213> ORGANISM: Gluconobacter suboxydans

<400> SEQUENCE: 74

```
cgcccatggg tgaacgcgtc tggagcgttg ggaacaagct ggaaaagcta ctggaaaaga    60
tccccgctgg ccgtgtcgca acaccggaag atgtcgcgga tatagttctg tatctcgcct   120
ccgacgcgtc gagcatggtc aacgggcagg aaatatttgt cgatggcgga tacacagccc   180
tttaggccgc cacatcttca aataaagaca tgtgatttta cggttttaac aaggccatgt   240
gcagggaatg gcctgcgcat ttcatgcaga tcaacaggtg taac                     284

<210> SEQ ID NO 75
<211> LENGTH: 234
<212> TYPE: DNA
<213> ORGANISM: Gluconobacter suboxydans

<400> SEQUENCE: 75
ctggaaaaga tccccgctgg ccgtgtcgca acaccggaag atgtcgcgga tatagttctg    60
tatctcgcct ccgacgcgtc gagcatggtc aacgggcagg aaatatttgt cgatggcgga   120
tacacagccc tttaggccgc cacatcttca aataaagaca tgtgatttta cggttttaac   180
aaggccatgt gcagggaatg gcctgcgcat ttcatgcaga tcaacaggtg taac          234

<210> SEQ ID NO 76
<211> LENGTH: 184
<212> TYPE: DNA
<213> ORGANISM: Gluconobacter suboxydans

<400> SEQUENCE: 76
tatagttctg tatctcgcct ccgacgcgtc gagcatggtc aacgggcagg aaatatttgt    60
cgatggcgga tacacagccc tttaggccgc cacatcttca aataaagaca tgtgatttta   120
cggttttaac aaggccatgt gcagggaatg gcctgcgcat ttcatgcaga tcaacaggtg   180
taac                                                                 184

<210> SEQ ID NO 77
<211> LENGTH: 134
<212> TYPE: DNA
<213> ORGANISM: Gluconobacter suboxydans

<400> SEQUENCE: 77
aaatatttgt cgatggcgga tacacagccc tttaggccgc cacatcttca aataaagaca    60
tgtgatttta cggttttaac aaggccatgt gcagggaatg gcctgcgcat ttcatgcaga   120
tcaacaggtg taac                                                      134

<210> SEQ ID NO 78
<211> LENGTH: 84
<212> TYPE: DNA
<213> ORGANISM: Gluconobacter suboxydans

<400> SEQUENCE: 78
aataaagaca tgtgatttta cggttttaac aaggccatgt gcagggaatg gcctgcgcat    60
ttcatgcaga tcaacaggtg taac                                           84

<210> SEQ ID NO 79
<211> LENGTH: 34
<212> TYPE: DNA
<213> ORGANISM: Gluconobacter suboxydans

<400> SEQUENCE: 79
gcctgcgcat ttcatgcaga tcaacaggtg taac                                34
```

<210> SEQ ID NO 80
<211> LENGTH: 51
<212> TYPE: DNA
<213> ORGANISM: Gluconobacter suboxydans

<400> SEQUENCE: 80
attccgaagg cggccccgaa ttccggaggg aacattatga ctgaatccag t        51

<210> SEQ ID NO 81
<211> LENGTH: 101
<212> TYPE: DNA
<213> ORGANISM: Gluconobacter suboxydans

<400> SEQUENCE: 81
attccgaagg cggccccgaa ttccggaggg aacattatga ctgaatccag tcagacatct    60
ccagaacttc ttctggcgct tgagggaatc tccaagagtt t                        101

<210> SEQ ID NO 82
<211> LENGTH: 151
<212> TYPE: DNA
<213> ORGANISM: Gluconobacter suboxydans

<400> SEQUENCE: 82
attccgaagg cggccccgaa ttccggaggg aacattatga ctgaatccag tcagacatct    60
ccagaacttc ttctggcgct tgagggaatc tccaagagtt ttccgggagt ccgggcgttg   120
cggaatgtca gcctcagcct ggagcgtgga g                                  151

<210> SEQ ID NO 83
<211> LENGTH: 201
<212> TYPE: DNA
<213> ORGANISM: Gluconobacter suboxydans

<400> SEQUENCE: 83
attccgaagg cggccccgaa ttccggaggg aacattatga ctgaatccag tcagacatct    60
ccagaacttc ttctggcgct tgagggaatc tccaagagtt ttccgggagt ccgggcgttg   120
cggaatgtca gcctcagcct ggagcgtgga gaaatccatg ctctgctggg ggaaaacggc   180
gctggaaaat ccacgatcat c                                             201

<210> SEQ ID NO 84
<211> LENGTH: 251
<212> TYPE: DNA
<213> ORGANISM: Gluconobacter suboxydans

<400> SEQUENCE: 84
attccgaagg cggccccgaa ttccggaggg aacattatga ctgaatccag tcagacatct    60
ccagaacttc ttctggcgct tgagggaatc tccaagagtt ttccgggagt ccgggcgttg   120
cggaatgtca gcctcagcct ggagcgtgga gaaatccatg ctctgctggg ggaaaacggc   180
gctggaaaat ccacgatcat caagatcatg gcggtatcc agtctcagga tgaagggcag   240
atctttctca a                                                        251

<210> SEQ ID NO 85
<211> LENGTH: 301
<212> TYPE: DNA
<213> ORGANISM: Gluconobacter suboxydans

<400> SEQUENCE: 85
attccgaagg cggccccgaa ttccggaggg aacattatga ctgaatccag tcagacatct    60

-continued

```
ccagaacttc ttctggcgct tgagggaatc tccaagagtt ttccgggagt ccggcgttg      120 cggaatgtca gcctcagcct ggagcgtgga gaaatccatg ctctgctggg ggaaaacggc     180
gctggaaaat ccacgatcat caagatcatg ggcggtatcc agtctcagga tgaagggcag    240
atctttctca acggaaagga gcgccacttc tccagctaca aggatgccat cagcgcaggt    300
a                                                                     301
```

<210> SEQ ID NO 86
<211> LENGTH: 351
<212> TYPE: DNA
<213> ORGANISM: Gluconobacter suboxydans

<400> SEQUENCE: 86

```
attccgaagg cggccccgaa ttccggaggg aacattatga ctgaatccag tcagacatct      60
ccagaacttc ttctggcgct tgagggaatc tccaagagtt ttccgggagt ccggcgttg     120 cggaatgtca gcctcagcct ggagcgtgga gaaatccatg ctctgctggg ggaaaacggc    180
gctggaaaat ccacgatcat caagatcatg ggcggtatcc agtctcagga tgaagggcag    240
atctttctca acggaaagga gcgccacttc tccagctaca aggatgccat cagcgcaggt    300
atcgggattg tttttcagga attcagcctg attcctgaac tcgatgccgt g             351
```

<210> SEQ ID NO 87
<211> LENGTH: 396
<212> TYPE: DNA
<213> ORGANISM: Gluconobacter suboxydans

<400> SEQUENCE: 87

```
attccgaagg cggccccgaa ttccggaggg aacattatga ctgaatccag tcagacatct      60
ccagaacttc ttctggcgct tgagggaatc tccaagagtt ttccgggagt ccggcgttg     120 cggaatgtca gcctcagcct ggagcgtgga gaaatccatg ctctgctggg ggaaaacggc    180
gctggaaaat ccacgatcat caagatcatg ggcggtatcc agtctcagga tgaagggcag    240
atctttctca acggaaagga gcgccacttc tccagctaca aggatgccat cagcgcaggt    300
atcgggattg tttttcagga attcagcctg attcctgaac tcgatgccgt ggataatatt    360
ttcctcggtc gtgagatgcg gaacgctctt ggcttt                               396
```

GLUCONOBACTER SUBOXYDANS SORBITOL DEHYDROGENASE, GENES AND METHODS OF USE THEREOF

BACKGROUND OF THE INVENTION

1. Field of the Invention

The invention relates to the fields of molecular biology, bacteriology and industrial fermentation. More specifically, the invention relates to the identification and isolation of nucleic acid sequences and proteins for subunits of a novel, membrane bound sorbitol dehydrogenase in *Gluconobacter suboxydans*. The invention further relates to the fermentative production of L-sorbose from D-sorbitol and the subsequent production of 2-keto-L-gulonic acid.

2. Related Art

Sorbitol dehydrogenase (SDH) is an enzyme responsible for the efficient conversion of D-sorbitol into L-sorbose during sorbose fermentation in the process of the manufacturing of 2-keto-L-gulonic acid (2-KLG), an important precursor for vitamin C synthesis. Gluconobacter possesses several SDHs, which may be categorized according to their cofactor requirement: (1) NAD-dependent, (2) NADP-dependent and (3) NAD(P)-independent types. Among them, NAD(P)-independent enzyme is believed to be directly involved in efficient production of sorbose during industrial sorbose fermentation (Cummins. J. T. et al.,*J Biol. Chem.*, 224, 323; 226, 3 01 (1957)).

The process of manufacturing L-sorbose from D-sorbitol is typically performed by fermentation with an acetic acid bacterium such as *Gluconobacter suboxydans* and *Acetobacter xylinum*. At room temperature, 96–99% of conversion is made in less than 24 hours (Liebster, J. et al., *Chem. List.*, 50:395 (1956)).

L-sorbose produced by the action of SDH is a substrate in the production of 2-keto-L-gulonic acid (2-KLG). A variety of processes for the production of 2KLG are known. For example, the fermentative production of 2-KLG via oxidation of L-sorbose to 2-KLG via a sorbosone intermediate is described for processes utilizing a wide range of bacteria: *Gluconobacter oxydans* (U.S. Pat. Nos. 4,935,359; 4,960, 695; 5,312,741; and 5,541,108); *Pseudogluconobacter saccharoketogenes* (U.S. Pat. No. 4,877,735; European Pat. No. 221 707); *Pseudomonas sorbosoxidans* (U.S. Pat. Nos. 4,933,289 and 4,892,823); mixtures of microorganisms from these and other genera, such as Acetobacter, Bacillus, Serratia, Mycobacterium, and Streptomyces (U.S. Pat. Nos. 3,912,592; 3,907,639; and 3,234,105); and novel bacterial strains (U.S. Pat. No. 5,834,231).

A number of enzymes involved in the fermentative oxidation of sorbitol, sorbose and sorbosone are identified in the literature. U.S. Pat. Nos. 5,888,786; 5,861,292; 5,834,263 and 5,753,481 disclose nucleic acid molecules encoding and/or isolated proteins for L-sorbose dehydrogenase and L-sorbosone dehydrogenase; and U.S. Pat. No. 5,747,301 discloses an enzyme with specificity for sorbitol dehydrogenase.

In addition to distinguishing Gluconobacter SDH's on the basis of cofactor requirements, other physical characteristics may be found in the literature that distinguish these different enzymes. For example, the sorbitol dehydrogenase identified in U.S. Pat. No. 5,747,301 is distinguished on the basis of subcellular location (membrane-bound) and a haloenzyme molecular weight of 800±50 kDa (10 homologous subunits of 79±5 kDa). The membrane-bound D-sorbitol dehydrogenase isolated by Shinagawa et al.(E. Shinagawa, K. Matsushita, 0. Adachi and M. Ameyama (Agric. Biol. Chem., 46, 135–141, 1982)) consisted of three kinds of subunits with molecular weights of 63,000, 51,000 and 17,000.

In an effort to improve the productivity of commercial fermentation in the production of 2 KLG, the inventors have identified a novel, membrane-bound sorbital dehydrogenase in a strain of G. suboxydans that is distinct from others described in the literature (Choi, E. S. et al., *FEMS Microbiol.* Lett., 125:45 (1995)).

SUMMARY OF THE INVENTION

This invention pertains to a novel, membrane-bound sorbitol dehydrogenase of *Gluconobacter suboxydans*. The isolated sorbitol dehydrogenase enzyme comprises three subunits: a first subunit of 75 kDa containing pyrroloquinoline quinone (PQQ) as cofactor; a second subunit of 50 kDa being a cytochrome c; and a third subunit of 29 kDa playing a very important role in the stability and the catalytic activity of the enzyme.

The present invention provides nucleic acid molecules for the 3 protein subunits of the Gluconobacter sorbitol dehydrogenase described herein. In a first specific embodiment, the invention provides an isolated nucleic acid molecule drawn to the first SDH subunit (75 kDA) identified by SEQ ID NO:1. In a second specific embodiment, the invention provides an isolated nucleic acid molecule drawn to the second SDH subunit (50 kDA) identified by SEQ ID NO:2. In a third specific embodiment the invention provides an isolated nucleic acid molecule drawn to the third SDH subunit (29 kDA) identified by SEQ ID NO:3. Other related embodiments are drawn to vectors, processes for producing the same and host cells carrying said vectors.

The invention also provides isolated nucleic acid molecules encoding the three subunits of the SDH of the invention. In one specific embodiment, the invention provides a cloned nucleic acid molecule encoding the 75 kDa and 50 kDa subunits. The structural genes for the first and the second subunit of sorbitol dehydrogenase are 2,265 bp and 1,437 bp, respectively, in size and are clustered in the cloned nucleic acid molecule which is a 5.7 kb PstI DNA fragment that defines the operon. In another specific embodiment, the invention provides a cloned nucleic acid molecule encoding the third, 29 kDa, SDH subunit protein. The structural gene coding for the third subunit is 921 bp in size and found in a 4.5 kb ClaI DNA fragment. Other related embodiments are drawn to vectors, processes to make the same and host cells containing said vectors.

The invention is also drawn to isolated polypeptides for the three subunits of the SDH described herein.

The invention also provides a method for the production of D-sorbose comprising: (a) transforming a host cell with at least one isolated nucleotide sequence selected from the group consisting of a polynucleotide comprising the polynucleotide sequence of SEQ ID NO:1; a polynucleotide comprising the polynucleotide sequence of SEQ ID NO:2; and a polynucleotide comprising the polynucleotide sequence of SEQ ID NO: 3; and (b) selecting and propagating said transformed host cell.

Another aspect of the invention is drawn to a method for production of 2-KLG comprising: (a) transforming a host cell with at least one isolated nucleotide sequence selected from the group consisting of a polynucleotide comprising the polynucleotide sequence of SEQ ID NO:1; a polynucleotide comprising the polynucleotide sequence of SEQ ID NO:2; and a polynucleotide comprising the polynucleotide sequence of SEQ ID NO: 3; and (b) selecting and propagating said transformed host cell.

BRIEF DESCRIPTION OF THE FIGURES

FIGS. 8A–8G presents the nucleotide sequence of 4,830 bases (SEQ ID NO:7) of the 5.7 kb PstI fragment. The deduced amino acid sequence for the first and the second subunit is shown below the nucleotide sequence. The N-terminal amino acid sequence obtained by the N-terminal amino acid sequencing of the purified sorbitol dehydrogenase is underlined. Signal sequence cleavage site is marked as a triangle. The heme-binding sequences are underlined with dotted lines. Potential ribosome-binding sequences (SD) are enclosed in boxes. The transcription termination stem-and-loop structure is indicated by arrows. The complete coding sequence for the first subunit gene is located at position 665–2,929 (SEQ ID NO:1), with the signal sequence located at position 665–766, and the coding sequence for the mature protein of the SDH first subunit located at position 767–2,929 (SEQ ID NO:22). The complete coding sequence for the second subunit gene is located at position 2,964–4,400 (SEQ ID NO:2), with the signal sequence located at position 2,964–3,071, and the coding sequence for the mature protein of the SDH second subunit located at position 3,072–4,400 (SEQ ID NO:23).

FIGS. 10A–10D presents the nucleotide sequence (SEQ ID NO:8) of DNA fragment containing the third subunit gene of sorbitol dehydrogenase. The deduced amino acid sequence is shown below the nucleotide sequence. Signal sequence cleavage site is marked as a triangle. Potential ribosome-binding sequence (SD) is enclosed in box. The complete coding sequence for the third subunit gene is located at position 1,384–2,304 (SEQ ID NO:3), with the signal sequence located at position 1,384–1,461, and the coding sequence for the mature protein of the SDH third subunit located at position 1,462–2,304 (SEQ ID NO:24).

DETAILED DESCRIPTION OF THE PREFERRED EMBODIMENTS

1. Definitions

Figure 1A:
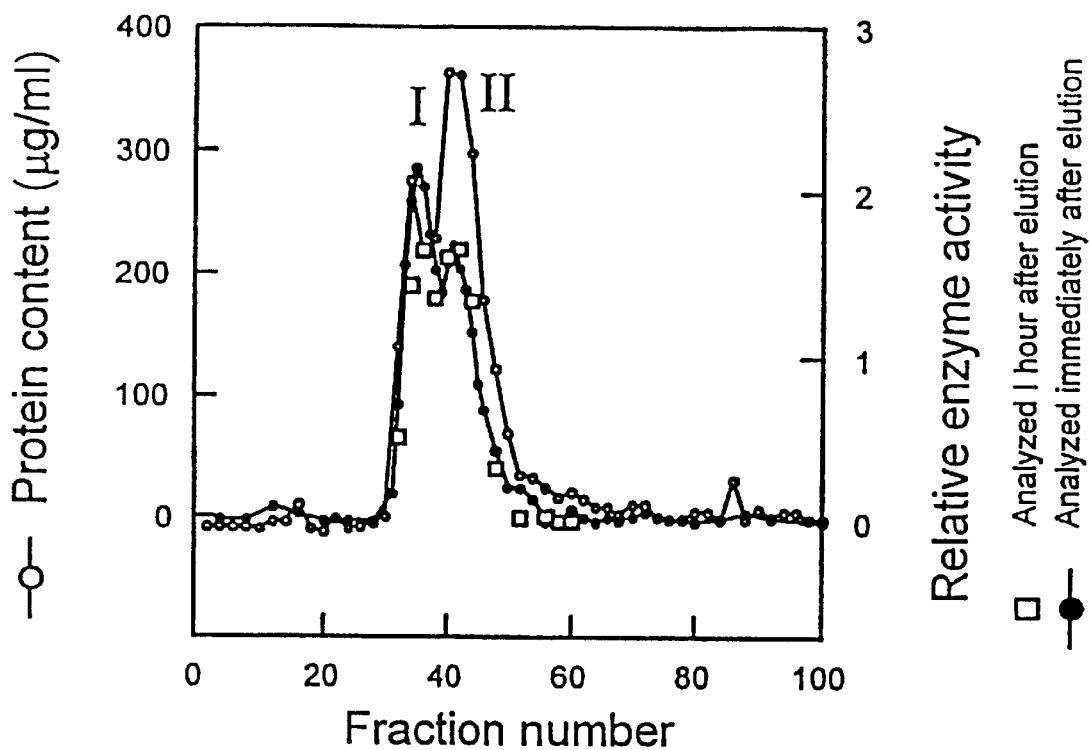
FIG. 1 presents DEAE-TSK column chromatography using a sodium acetate buffer of pH 5.0 (A) and pH 6.0 (B).

Cloning Vector: A plasmid or phage DNA or other DNA sequence which is able to replicate autonomously in a host cell, and which is characterized by one or a small number of restriction endonuclease recognition sites at which such DNA sequences may be cut in a determinable fashion without loss of an essential biological function of the vector, and into which a DNA fragment may be spliced in order to bring about its replication and cloning. The cloning vector may further contain a marker suitable for use in the identification of cells transformed with the cloning vector. Markers, for example, provide tetracycline resistance or ampicillin resistance.

Expression: Expression is the process by which a polypeptide is produced from a structural gene. The process involves transcription of the gene into mRNA and the translation of such mRNA into polypeptide(s).

Expression Vector: A vector similar to a cloning vector but which is capable of enhancing the expression of a gene which has been cloned into it, after transformation into a host. The cloned gene is usually placed under the control of (i.e., operably linked to) certain control sequences such as promoter sequences. Promoter sequences may be either constitutive or inducible.

Gene: A DNA sequence that contains information needed for expressing a polypeptide or protein.

Host: Any prokaryotic or eukaryotic cell that is the recipient of a replicable expression vector or cloning vector. A "host," as the term is used herein, also includes prokaryotic or eukaryotic cells that can be genetically engineered by well known techniques to contain desired gene(s) on its chromosome or genome. For examples of such hosts, see Sambrook et al., *Molecular Cloning: A Laboratory Manual*, Second Edition, Cold Spring Harbor Laboratory, Cold Spring Harbor, N.Y. (1989).

Homologous/Nonhomologous: Two nucleic acid molecules are considered to be "homologous" if their nucleotide sequences share a similarity of greater than 50%, as determined by HASH-coding algorithms (Wilber, W. J. and Lipman, D. J., *Proc. Natl. Acad. Sci.* 80:726–730 (1983)). Two nucleic acid molecules are considered to be "nonhomologous" if their nucleotide sequences share a similarity of less than 50%.

Mutation: As used herein, the term refers to a single base pair change, insertion or deletion in the nucleotide sequence of interest.

Mutagenesis: As used herein, the term refers to a process whereby a mutation is generated in DNA. With "random" mutatgenesis, the exact site of mutation is not predictable, occurring anywhere in the chromosome of the microorganism, and the mutation is brought about as a result of physical damage caused by agents such as radiation or chemical treatment.

Operon: As used herein, the term refers to a unit of bacterial gene expression and regulation, including the structural genes and regulatory elements in DNA.

Parental Strain: As used herein, the term refers to a strain of microorganism subjected to some form of mutagenesis to yield the microorganism of the invention.

Phenotype: As used herein, the term refers to observable physical characteristics dependent upon the genetic constitution of a microorganism.

Promoter: A DNA sequence generally described as the 5' region of a gene, located proximal to the start codon. The transcription of an adjacent gene(s) is initiated at the promoter region. If a promoter is an inducible promoter, then the rate of transcription increases in response to an inducing agent. In contrast, the rate of transcription is not regulated by an inducing agent if the promoter is a constitutive promoter.

Recombinant Host: According to the invention, a recombinant host may be any prokaryotic or eukaryotic cell which contains the desired cloned genes on an expression vector or cloning vector. This term is also meant to include those prokaryotic or eukaryotic cells that have been genetically engineered to contain the desired gene(s) in the chromosome or genome of that organism.

Recombinant Vector: Any cloning vector or expression vector which contains the desired cloned gene(s).

2. Isolation and Purification of Sorbitol Dehydrogenase

The present invention isolates and purifies SDH from the cytoplasmic membrane of *G. suboxydans* KCTC (Korea Culture Type Collection) 2111 (equivalent to ATCC 621) using a series of column chromatographic steps. Biochemical properties of the purified enzyme are provided, as well as the isolation of each subunit and a determination of the N-terminal amino acid sequence of each subunit using an amino acid sequence analyzer (Applied Biosystems, 477A).

The newly characterized enzyme is different from the reported FAD-dependent SDH from *G. suboxydans* IFO 3254 strain (Shinagawa, E. et al., *Agric. Biol. Chem.*, 46:135 (1982)), containing pyrroloquinoline quinone (PQQ) as a cofactor and comprising three subunits (Choi, E. S. etal., *FEMS Microbiol. Lett.*, 125:45 (1995)).

The SDH of the invention may be isolated using standard protein techniques. Briefly, *G. suboxydans* KCTC 2111 is cultured in SYP medium (5% D-sorbitol, 1% Bacto-Peptone, 0.5% yeast extract) and the cells are lysed in a 10 mM sodium acetate buffer solution (pH 5.0). After centrifuged at 12,000 g to remove cell debris, the supernatant is centrifuged in an ultracentrifuge to recover cytoplasmic membrane fraction. Purification is completed by solubilizing the cytoplasmic membrane fraction with 1.5% n-octylglucoside (Boehringer Mannheim) and passage over a series of chromatographic columns, including CM-TSK 650 (S) (Merck), DEAE-TSK 650 (S) (Merck), Mono-S (Pharmacia) and Superose 12 (Pharmacia).

The purified enzyme is active towards polyols such as D-sorbitol (100%), D-mannitol (68%) and D-ribitol (70%). Activity of the enzyme increases up to nine fold when pyrroloquinoline quinone (PQQ) is added, suggesting that PQQ is a cofactor for the enzyme; fluorescence spectrum analysis confirmed that the purified enzyme contains pyrroloquinoline quinone (PQQ). The absorption spectrum analysis of the purified enzyme demonstrates that this enzyme contains cytochrome c. When the purified enzyme is subjected to polyacrylamide gel electrophoresis (PAGE) at pH 4.3 (Reisfeld, R. A. et al., *Nature*, 195:281 (1962)), it forms a single activity band after activity staining on the gel.

The initial SDS-PAGE analysis of the purified enzyme showed that the enzyme comprised three subunits of 75 kDa, 50 kDa and 14 kDa which were named the first subunit, the second subunit, and the third subunit, respectively (Choi, E. S. et al., *FEMS Microbiol. Lett.*, 125:45 (1995)). In a further study of the enzyme, however, it was discovered that another subunit of 29 kDa played a very important role in the stability and the catalytic activity of SDH. That is, while investigating a variety of pH conditions in an effort to increase protein separation capability during purification on DEAE-TSK column, it was discovered that the partially resolved activity peaks eluting at pH 5.0 were completely resolved into two separate activity peaks when eluted at pH 6.0. The early eluting activity peak quickly lost enzyme activity and the late eluting activity peak remained stable. By SDS-PAGE analysis of these two peaks, it was found that the peak with stable enzyme activity contained an additional subunit of 29 kDa in addition to the 75 and 50 kDa subunits, whereas the one that quickly lost enzyme activity contained only 75 and 50 kDa subunits. This additional subunit of 29 kDa was renamed the third subunit: it is uncertain whether the 14 kDa subunit previously assigned the third subunit is a true subunit of the enzyme when comparing the relative amount with other subunits on the acrylamide gel. It was also found that a further increase of the pH ofthe elution buffer to pH 6.5 resulted in a complete separation of three subunits into individual subunits.

When different combinations of two or three subunits were tested for the restoration of enzyme activity by the Ferric-Dupanol assay method (Wood, W. A. et al., *Meth. Enzymol*, 5:287 (1962)), it was found that enzyme activity was fully restored only in the presence of the third subunit of 29 kDa. Therefore, it was concluded that the third subunit of 29 kDa plays important roles in the stability and the catalytic activity of SDH.

The Michaelis-Menten constants, when using D-sorbitol as substrate, was determined to be Km=120 mM and Vmax= $3.9 \times 10^{-5}$ M/min. Dichlorophenol indophenol (DCIP) or ferricyanide worked effectively as electron acceptor of the enzyme. When phenazine methosulfate (PMS) was added as an electron mediator, the enzyme activity increased. Calcium or magnesium ion addition significantly increased purified enzyme activity, whereas copper ion addition seriously inhibited activity.

Further details ofthe purification and characterization ofthe SDH enzyme of the invention are provided in Example 1.

3. Nucleic Acid Molecules of the Invention

The invention provides isolated nucleic acid molecules encoding one or more of the three subunits of the SDH enzyme described herein. Methods and techniques designed for the manipulation of isolated nucleic acid molecules are well known in the art. For example, methods for the isolation, purification and cloning of nucleic acid molecules, as well as methods and techniques describing the use of eukaryotic and prokaryotic host cells and nucleic acid and protein expression therein, are described by Sambrook, et al., *Molecular Cloning: A Laboratory Manual*, Second Edition, Cold Spring Harbor, N.Y., 1989, and Current Protocols in Molecular Biology, Frederick M. Ausubel et al. Eds., John Wiley & Sons, Inc., 1987, the disclosure of which is hereby incorporated by reference.

More particularly, the invention provides several isolated nucleic acid molecules encoding the individual 75 kDa, 50 kDa, and 29 kDa subunit proteins of SDH enzyme of the invention. Additionally, the invention provides several isolated nucleic acid molecules encoding one or more of subunit proteins of the SDH enzyme of the invention. For the purposes of clarity, the particular isolated nucleic molecules ofthe invention are described. Thereafter, specific properties and characteristics of these isolated nucleic acid molecules are described in more detail.

Unless otherwise indicated, all nucleotide sequences determined by sequencing a DNA molecule herein were determined using an automated DNA sequencer (such as the Model 373A from Applied Biosystems, Inc.), and all amino acid sequences of polypeptides encoded by DNA molecules determined herein were predicted by translation of a DNA sequence determined as above. Therefore, as is known in the art for any DNA sequence determined by this automated approach, any nucleotide sequence determined herein may contain some errors. Nucleotide sequences determined by automation are typically at least about 90% identical, more typically at least about 95% to at least about 99.9% identical to the actual nucleotide sequence of the sequenced DNA molecule. The actual sequence can be more precisely determined by other approaches including manual DNA sequencing methods well known in the art. As is also known in the art, a single insertion or deletion in a determined nucleotide sequence compared to the actual sequence will cause a frame shift in translation of the nucleotide sequence such that the predicted amino acid sequence encoded by a determined nucleotide sequence will be completely different from the amino acid sequence actually encoded by the sequenced DNA molecule, beginning at the point of such an insertion or deletion.

In one embodiment, the invention provides an isolated nucleic acid molecule for the first (75 kDa) subunit of the SDH enzyme of the invention comprising a polynucleotide sequence selected from the group consisting of (a) the polynucleotide of SEQ ID NO:1; (b) a polynucleotide fragment at least about 20 nucleotides in length of the polynucleotide of SEQ ID NO:1; (c) a polynucleotide encoding the amino acid sequence of SEQ ID NO:4; and (d) a polynucleotide encoding a fragment at least about 10 amino acids in length of the amino acid sequence of SEQ ID NO:4.

In another embodiment, the invention provides an isolated nucleic acid molecule for the first (75 kDa) subunit of the SDH enzyme of the invention comprising a polynucleotide at least about 95% identical to the isolated nucleic acid sequence for the first (75 kDa) subunit of the SDH enzyme of the invention described above.

Another embodiment of the invention provides an isolated nucleic acid molecule for the second (50 kDa) subunit of the SDH enzyme of the invention comprising a polynucleotide sequence selected from the group consisting of: (a) the polynucleotide, or fragment thereof, of SEQ ID NO:2; (b) a polynucleotide fragment at least about 20 nucleotides in length of the polynucleotide of SEQ ID NO:2; (c) a polynucleotide encoding the amino acid sequence of SEQ ID NO:5; and (d) a polynucleotide encoding a fragment at least about 10 amino acids in length of the amino acid sequence of SEQ ID NO:5.

In another embodiment, the invention provides an isolated nucleic acid molecule for the second (50 kDa) subunit of the SDH enzyme of the invention comprising a polynucleotide at least about 95% identical to the isolated nucleic acid sequence for the second (50 kDa) subunit of the SDH enzyme of the invention described above.

Another embodiment of the invention provides an isolated nucleic acid molecule for the third (29 kDa) subunit of the SDH enzyme of the invention comprising a polynucleotide sequence selected from the group consisting of: (a) the polynucleotide of SEQ ID NO:3; (b)a polynucleotide fragment at least about 20 nucleotides in length of the polynucleotide of SEQ ID NO:3; (c) a polynucleotide encoding the amino acid sequence of SEQ ID NO:6; and (d) a polynucleotide encoding a fragment at least about 10 amino acids in length of the amino acid sequence of SEQ ID NO:6.

In another embodiment, the invention provides an isolated nucleic acid molecule for the third (29 kDa) subunit of the SDH enzyme of the invention comprising a polynucleotide at least about 95% identical to the isolated nucleic acid sequence for the third (29 kDa) subunit of the SDH enzyme of the invention described above.

Another embodiment the invention provides an isolated nucleic acid molecule encoding both the first (75 kDa) and second (50 kDa) subunit proteins of the SDH enzyme of the invention comprising a polynucleotide sequence selected from the group consisting of: (a) the polynucleotide of SEQ ID NO:7; and (b) a polynucleotide fragment at least about 20 nucleotides in length of the polynucleotide of SEQ ID NO:7.

In another embodiment, the invention provides an isolated nucleic acid molecule for the first (75 kDa) and second (50 kDa) subunit proteins of the SDH enzyme of the invention comprising a polynucleotide at least about 95% identical to the isolated nucleic acid sequence for the first (75 kDa) and second (50 kDa) subunit proteins of the SDH enzyme of the invention.

Another embodiment of the invention provides an isolated nucleic acid molecule for the third (29 kDa) subunit of the SDH enzyme of the invention comprising a polynucleotide sequence selected from the group consisting of: (a) the polynucleotide of SEQ ID NO:8; and (b) a polynucleotide fragment at least about 20 nucleotides in length of the polynucleotide of SEQ ID NO:8.

In another embodiment, the invention provides an isolated nucleic acid molecule for the third (29 kDa) subunit of the SDH enzyme of the invention comprising an isolated nucleic acid molecule at least about 95% identical to the isolated nucleic acid molecule for the third (29 kDa) subunit of the SDH enzyme of the invention described above.

By "isolated" nucleic acid molecule is intended a nucleic acid molecule, DNA or RNA, which has been removed from its native environment. For example, recombinant DNA molecules contained in a vector are considered isolated for the purposes of the present invention. Further examples of isolated DNA molecules include recombinant DNA molecules maintained in heterologous host cells or purified (partially or substantially) DNA molecules in solution. Isolated RNA molecules include in vivo or in vitro RNA transcripts of the DNA molecules of the present invention. Isolated nucleic acid molecules according to the present invention further include such molecules produced synthetically.

RNA vectors may also be utilized with the SDH nucleic acid molecules disclosed in the invention. These vectors are based on positive or negative strand RNA viruses that naturally replicate in a wide variety of eukaryotic cells (Bredenbeek, P. J. and Rice, C. M., *Virology* 3:297-310 (1992)). Unlike retroviruses, these viruses lack an intermediate DNA life-cycle phase, existing entirely in RNA form. For example, alpha viruses are used as expression vectors for foreign proteins because they can be utilized in a broad range of host cells and provide a high level of expression; examples of viruses of this type include the Sindbis virus and Semliki Forest virus (Schlesinger, S., *TIBTECH* 11:18–22 (1993); Frolov, I., et al., *Proc. Natl. Acad. Sci.* (USA) 93:11371–11377 (1996)). As exemplified by Invitrogen's Sinbis expression system, the investigator may conveniently maintain the recombinant molecule in DNA form (pSinrep5 plasmid) in the laboratory, but propagation in RNA form is feasible as well. In the host cell used for expression, the vector containing the gene of interest exists completely in RNA form and may be continuously propagated in that state if desired.

In another embodiment, the invention further provides variant nucleic acid molecules that encode portions, analogs or derivatives ofthe isolated nucleic acid molecules described herein. Variants include those produced by nucleotide substitutions, deletions or additions, which may involve one or more nucleotides. The variants may be altered in coding regions, non-coding regions, or both. Alterations in the coding regions may produce conservative or non-conservative amino acid substitutions, deletions or additions.

Variants of the isolated nucleic acid molecules of the invention may occur naturally, such as a natural allelic variant. By an "allelic variant" is intended one of several alternate forms of a gene occupying a given locus on a chromosome of an organism. *Genes II*, Lewin, B., ed., John Wiley & Sons, New York (1985). Non-naturally occurring variants may be produced using art-known mutagenesis techniques.

Isolated nucleic acid molecules of the invention also include polynucleotide sequences that are 95%, 96%, 97%, 98% and 99% identical to the isolated nucleic acid molecules described herein. Computer programs such as the BestFit program (Wisconsin Sequence Analysis Package, Version 10 for Unix, Genetics Computer Group, University Research Park, 575 Science Drive, Madison, Wis. 53711) may be used to determine whether any particular nucleic acid molecule is at least 95%, 96%, 97%, 98% or 99% identical to the nucleotide sequences disclosed herein or the the nucleotides sequences of the deposited clones described herein. BestFit uses the local homology algorithm of Smith and Waterman, *Advances in Applied Mathematics* 2: 482–489 (1981), to find the best segment of homology between two sequences.

By way of example, when a computer alignment program such as BestFit is utilized to determine 95% identity to a reference nucleotide sequence, the percentage of identity is calculated over the full length of the reference nucleotide sequence and gaps in homology of up to 5% of the total number of nucleotides in the reference sequence are allowed. Thus, per 100 base pairs analyzed, 95% identity indicates that as many as 5 of 100 nucleotides in the subject sequence may vary from the reference nucleotide sequence.

The invention also encompasses fragments ofthe nucleotide sequences and isolated nucleic acid molecules described herein. In a preferred embodiment the invention provides for fragments that are at least 20 bases in length. The length of such fragments may be easily defined algebraically. For example, SEQ ID NO:1 provides for an isolated nucleotide molecule that is 2, 265 bases in length. A fragment (F1) of SEQ ID NO:1 at least 20 bases in length may be defined as F1=20+X, wherein X is defined to be zero or any whole integer from 1 to 2,245. Similarly, fragments for other isolated nucleic acid molecules described herein may be defined as follows: for SEQ ID NO:2 which is 1,437 bases in length, a fragment (F2) of SEQ ID NO:2 at least 20 bases in length may be defined as F2=20+X, wherein X is defined to be zero or any whole integer from 1 to 1,417; for SEQ ID NO:3 which is 921 bases in length, a fragment (F3) of SEQ ID NO:3 at least 20 bases in length may be defined as F3=20+X, wherein X is defined to be zero or any whole integer from 1 to 901; for SEQ ID NO:7 which is 4,830 bases in length, a fragment (F7) of SEQ ID NO:7 at least 20 bases in length may be defined as F7=20+X, wherein X is defined to be zero or any whole integer from 1 to 4,810; and for SEQ ID NO:8 which is 2,700 bases in length, a fragment (F8) of SEQ ID NO:8 at least 20 bases in length may be defined as F8=20+X, wherein X is defined to be zero or any whole integer from 1 to 2,680. As will be understood by those skilled in the art, the isolated nucleic acid sequence fragments of the invention may single stranded or double stranded molecules.

The invention discloses isolated nucleic acid sequences encoding the three subunit proteins of the SDH enzyme ofthe invention. Computer analysis provides information regarding the open reading frames, putative signal sequence and mature protein forms of each subunit. Genes encoding the first (75 kDa) and second (50 kDa) subunits are completely contained in a 5.7 kb Pst I fragment of the lambda GEM 5-1 clone, which was deposited in bacteria under the accession number KCTC 0593BP on Mar. 25, 1999 and as DNA under accession number KCTC 0597BP on Apr. 2, 1999 with the Korean Collection for Type Cultures (KCTC), Korea esearch Institute of Bioscience and Biotechnology (KRIBB), 52, Oun-Dong, Yusong-Ku, Taejon 305-33, Republic of Korea. The third (29 kDa) subunit gene is contained in a sequence 4.5 kb in length, referred to as Cla I-#69, which was deposited in bacteria under the accession number KCTC 0594BP on Mar. 25, 1999 and as DNA under accession number KCTC 0598BP on Apr. 2, 1999 with the Korean Collection for Type Cultures (KCTC), Korea Research Institute of Bioscience and Biotechnology (KRIBB), 52, Oun-Dong, Yusong-Ku, Taejon 305-33, Republic of Korea.

Thus, the invention provides an isolated nucleic acid molecule (KCTC 0597BP) carried in the novel strain KCTC 0593BP, and the invention also provides an isolated nucleic acid molecule (KCTC 0598BP) carried in the novel strain KCTC 0594BP.

Sequence obtained from the lambda GEM 5-1, 5.7 kb Pst I fragment is presented in FIG. 8 and assigned SEQ IDNO:7. The complete coding sequence for the first subunit gene is located at position 665–2,929,(SEQ ID NO:1), with the signal sequence located at position 665–766, and the coding sequence for the mature protein of the SDH first subunit located at position 767–2,929 (SEQ ID NO:22). The complete coding sequence for the second subunit gene is located at position 2,964–4,400 (SEQ ID NO:2), withthe signal sequence located at position 2,964–3,071, and the coding sequence for the mature protein of the SDH second subunit located at position 3,072–4,400 (SEQ ID NO:23).

Thus, another embodiment ofthe invention provides isolated nucleic acid molecules derived from sequence obtained from the lambda GEM 5-1, 5.7 kb Pst I fragment that is presented in FIG. 8 and identified as SEQ ID NO:7. Such isolated nucleic acid molecules include the following: (1) nucleotides 1–664 of SEQ ID NO:7 identified as SEQ ID NO:28; (2) nucleotides 50–664 of SEQ ID NO:7 identified as SEQ ID NO:29; (3) nucleotides 100–664 of SEQ ID NO:7 identified as SEQ ID NO:30; (4) nucleotides 150–664 of SEQ ID NO:7 identified as SEQ ID NO:31; (5) nucleotides 200–664 of SEQ ID NO:7 identified as SEQ ID NO:32; (6) nucleotides 250–664 ofSEQ ID NO:7 dentified as SEQ ID NO:33; (7) nucleotides 300–664 of SEQ ID NO:7 identified as SEQ ID NO:34; (8) nucleotides 350–664 of SEQ ID NO:7 identified as SEQ ID NO:35; (9) nucleotides 400–664 of SEQ ID NO:7 identified as SEQ ID NO:36; (10) nucleotides 450–664 of SEQ ID NO:7 identified as SEQ ID NO:37; (11) nucleotides 500–664 of SEQ ID NO:7 identified as SEQ ID NO:38; (12) nucleotides 550–664 of SEQ ID NO:7 identified as SEQ ID NO:39; (13) nucleotides 600–664 of SEQ ID NO:7 identified as SEQ ID NO:40; (14) the nucleotide sequence encoding the full length subunit 1 protein of the SDH of the invention from nucleotides 665–2,929 of SEQ ID NO:7 identified as SEQ ID NO:1; (15) the nucleotide sequence encoding the mature form of the subunit 1 protein of the SDH of the invention from nucleotides 767–2,929 of SEQ ID NO:7 identified as SEQ ID NO:22; (16) the nucleotide sequence encoding the full length subunit 2 protein of the SDH of the invention from nucleotides 2,964–4,400 of SEQ ID NO:7 identified as SEQ ID NO:2; (17) the nucleotide sequence encoding the mature form of the subunit 2 protein of the SDH of the invention from nucleotides3, 072–4,400 of SEQ ID NO:7 identified as SEQ ID NO:23; (18) nucleotides 2,930–2,963 of SEQ ID NO:7 identified as SEQ ID NO:41; (19) nucleotides 4,401–4,451 of SEQ ID NO:7 identified as SEQ ID NO:42; (20) nucleotides 4,401–4,501 of SEQ ID NO:7 identified as SEQ ID NO:43; (21) nucleotides 4,401–4,551 of SEQ ID NO:7 identified as SEQ ID NO:44; (22) nucleotides 4,401–4,601 of SEQ ID NO:7 identified as SEQ ID NO:45; (23) nucleotides 4,401–4,651 of SEQ ID NO:7 identified as SEQ ID NO:46; (24) nucleotides 4,401–4,701 of SEQ ID NO:7 identified as SEQ ID NO:47; (25) nucleotides 4,401–4,751 of SEQ ID NO:7 identified as SEQ ID NO:48; (26) nucleotides 4,401–4,801 of SEQ ID NO:7 identified as SEQ ID NO:49; and (27) nucleotides 4,401–4,830 of SEQ ID NO:7 identified as SEQ ID NO:50.

The sequence obtained from the Cla I-#69 clone is presented in FIG. 10 and assigned SEQ ID NO:8. The complete coding sequence for the third subunit gene is located at position 1,384–2,304 (SEQ ID NO:3), with the signal sequence located at position 1,384–1,461, and the coding sequence for the mature protein of the SDH third subunit located at position 1,462–2,304 (SEQ ID NO:24).

Thus, another embodiment of the invention provides isolated nucleic acid molecules derived from sequence obtained from the Cla I-#69 clone that is presented in FIG. 10 and assigned SEQ ID NO:8. Such isolated nucleic acid molecules include the following: (1) nucleotides 1–1,383 of SEQ ID NO:8 identified as SEQ ID NO:51; (2) nucleotides 50–1,383 of SEQ ID NO:8 identified as SEQ ID NO:52; (3) nucleotides 100–1,383 of SEQ ID NO:8 identified as SEQ ID NO:53; (4) nucleotides 150–1,383 of SEQ ID NO:8 identified as SEQ ID NO:54; (5) nucleotides 200–1,383 of SEQ ID NO:8 identified as SEQ ID NO:55; (6) nucleotides 250–1,383 of SEQ ID NO:8 identified as SEQ ID NO:56; (7) nucleotides 300–1,383 of SEQ ID NO:8 identified as SEQ ID NO:57; (8) nucleotides 350–1,383 of SEQ ID NO:8 identified as SEQ ID NO:58; (9) nucleotides 400–1,383 of SEQ ID NO:8 identified as SEQ ID NO:59; (10) nucleotides 450–1,383 of SEQ ID NO:8 identified as SEQ ID NO:60; (11) nucleotides 500–1,383 of SEQ ID NO:8 identified as SEQ ID NO:61; (12) nucleotides 550–1,383 of SEQ ID NO:8 identified as SEQ ID NO:62; (13) nucleotides 600–1,383 of SEQ ID NO:8 identified as SEQ ID NO:63; (14) nucleotides 600–1,383 of SEQ ID NO:8 identified as SEQ ID NO:64; (15) nucleotides 650–1,383 of SEQ ID NO:8 identified as SEQ ID NO:65; (16) nucleotides 700–1,383 of SEQ ID NO:8 identified as SEQ ID NO:66; (17) nucleotides 750–1,383 of SEQ ID NO:8 identified as SEQ ID NO:67; (18) nucleotides 800–1,383 of SEQ ID NO:8 identified as SEQ ID NO:68; (19) nucleotides 850–1,383 of SEQ ID NO:8 identified as SEQ ID NO:69; (20) nucleotides 900–1,383 of SEQ ID NO:8 identified as SEQ ID NO:70; (21) nucleotides 950–1,383 of SEQ ID NO:8 identified as SEQ ID NO:71; (22) nucleotides 1,000–1,383 of SEQ ID NO:8 identified as SEQ ID NO:72; (23) nucleotides 1,050–1,383 of SEQ ID NO:8 identified as SEQ ID NO:73; (24) nucleotides 1,100–1,383 of SEQ ID NO:8 identified as SEQ ID NO:74; (25) nucleotides 1,150–1,383 of SEQ ID NO:8 identified as SEQ ID NO:75; (26) nucleotides 1,200–1,383 of SEQ ID NO:8 identified as SEQ ID NO:76; (27) nucleotides 1,250–1,383 of SEQ ID NO:8 identified as SEQ ID NO:77; (28) nucleotides 1,300–1,383 of SEQ ID NO:8 identified as SEQ ID NO:78; (29) nucleotides 1,350–1,383 of SEQ ID NO:8 identified as SEQ ID NO:79;(30) the nucleotide sequence encoding the full length SDH subunit 3 protein of the invention from nucleotides 1,384–1,461 of SEQ ID NO:8 identified as SEQ ID NO:3; (31) the nucleotide sequence encoding the mature form ofthe SDH subunit 3 protein of the invention from nucleotides 1,462–2,304 of SEQ ID NO:8 identified as SEQ ID NO:24; (32) nucleotides 2,305–2,355 of SEQ ID NO:8 identified as SEQ ID NO:80; (33) nucleotides 2,305–2,405 of SEQ ID NO:8 identified as SEQ ID NO:81; (34) nucleotides 2,305–2,455 of SEQ ID NO:8 identified as SEQ ID NO:82; (35) nucleotides 2,305–2,505 of SEQ ID NO:8 identified as SEQ ID NO:83; (32) nucleotides 2,305–2,555 of SEQ ID NO:8 identified as SEQ ID NO:84; (32) nucleotides 2,305–2,605 of SEQ ID NO:8 identified as SEQ ID NO:85; (32) nucleotides 2,305–2,655 of SEQ ID NO:8 identified as SEQ ID NO:86; and (33) nucleotides 2,305–2,700 of SEQ ID NO:8 identified as SEQ ID NO:87.

The invention also includes recombinant constructs comprising one or more of the sequences as broadly described above. The constructs comprise a vector, such as a plasmid or viral vector, into which a sequence of the invention has been inserted, in a forward or reverse orientation. In a preferred aspect of this embodiment, the construct further comprises regulatory sequences, including, for example, a promoter, operably linked to the sequence. Large numbers of suitable vectors and promoters are known to those of skill in the art and are commercially available. The following vectors are provided by way of example: Bacterial-pET (Novagen), pQE70, pQE60, pQE-9 (Qiagen), pBs, phagescript, psiX174, pBlueScript SK, pBsKS, pNH8a, pNH16a, pNH18a, pNH46a (Stratagene); pTrc99A, pKK223-3, pKK23 3-3, pDR540, pRIT5 (Pharmacia); and Eukaryotic-pWLneo, pSV2cat, pOG44, pXT1, pSG (Stratagene) pSVK3, pBPV, pMSG, pSVL (Pharmacia). Thus, these and any other plasmids or vectors may be used as long as they are replicable and viable in the host.

Promoter regions can be selected from any desired gene using CAT (chloramphenicol transferase) vectors or other vectors with selectable markers. Two appropriate vectors are pKK232-8 and pCM7. Particular named bacterial promoters include lacI, lacZ, T3, T7, gpt, lambda $P_R$, $P_L$ and trp. Eukaryotic promoters include CMV immediate early, HSV thymidine kinase, early and late SV40, LTRs from retrovirus, and mouse metallothionein-I. Selection of the appropriate vector and promoter is well within the level of ordinary skill in the art.

In another embodiment, the invention provides processes for producing the vectors described herein which comprises: (a) inserting the isolated nucleic acid molecule of the invention into a vector; and (b) selecting and propagating said vector in a host cell.

Representative examples of appropriate hosts include, but are not limited to, bacterial cells, such as Gluconobacter, Brevibacterium, Corynebacterim, *E. coli*, Streptomyces, *Salmonella typhimurium*, Acetobacter, Pseudomonas, Pseudogluconobacter, Bacillus and Agrobacterium cells; fungal and yeast organisms including Saccharomyces, Kluyveromyces, Aspergillus and Rhizopus; insect cells such as Drosophila S2 and Spodoptera Sf9 cells; animal cells such as CHO, COS and Bowes melanoma cells; and plant cells. Appropriate culture mediums and conditions for the above-described host cells are known in the art.

4. Polypeptides of the Invention

The invention provides isolated polypeptide molecules for the SDH enzyme of the invention. Methods and techniques designed for the manipulation of isolated polypeptide molecules are well known in the art. For example, methods for the isolation and purification of polypeptide molecules are described Current Protocols in Protein Science, John E. Coligan et al. Eds., John Wiley & Sons, Inc., 1997, the disclosure of which is hereby incorporated by reference.

More particularly, the invention provides several isolated polypeptide molecules encoding the individual 75 kDa, 50 kDa, and 29 kDa subunit proteins of SDH enzyme of the invention. For the purposes of clarity, the particular isolated polypeptide molecules ofthe invention are described. Thereafter, specific properties and characteristics of these isolated polypeptide molecules are described in more detail.

In one embodiment, the invention provides an isolated polypeptide comprising a polypeptide sequence selected from the group consisting of: (a) the polypeptide sequence encoded in the polynucleotide sequence of SEQ ID NO:1; (b) the polypeptide sequence of SEQ ID NO:4; and (c) a polypeptide at least about 10 amino acids long from the polypeptide sequence of SEQ ID NO:4.

In another embodiment, the invention provides an isolated polypeptide comprising a polypeptide sequence selected from the group consisting of: (a) the polypeptide sequence encoded in the polynucleotide sequence of SEQ ID NO:2; (b) the polypeptide sequence of SEQ ID NO:5; and (c) a polypeptide at least about 10 amino acids long from the polypeptide sequence of SEQ ID NO:5.

In yet another embodiment, the invention provides an isolated polypeptide comprising a polypeptide sequence selected from the group consisting of: (a) the polypeptide sequence encoded in the polynucleotide sequence of SEQ ID NO:3; (b) the polypeptide sequence of SEQ ID NO:6; and (c) a polypeptide at least about 10 amino acids long from the polypeptide sequence of SEQ ID NO:6.

Other embodiments of the invention include an isolated polypeptide sequence comprising the polypeptide encoded by the isolated nucleic acid sequence SEQ ID NO:7; an isolated polypeptide sequence comprising the polypeptide encoded by the isolated nucleic acid sequence SEQ ID NO:8; an isolated polypeptide sequence comprising the polypeptide encoded by the DNA clone contained in KCTC Deposit No. 0593BP; and an isolated polypeptide sequence comprising the polypeptide encoded by the DNA clone contained in KCTC Deposit No. 0594BP.

The term "isolated polypeptide" is used herein to mean a polypeptide removed from its native environment. Thus, a polypeptide produced and/or contained within a recombinant host cell is considered isolated for purposes of the present invention. Also intended as an "isolated polypeptide" are polypeptides that have been purified, partially or substantially, from a recombinant host cell.

Polypeptides of the present invention include naturally purified products, products of chemical synthetic procedures, and products produced by recombinant techniques from a prokaryotic or eukaryotic host, including, for example, bacterial, yeast, higher plant, insect and mammalian cells. Depending upon the host employed in a recombinant production procedure, the polypeptides of the present invention may be glycosylated or may be non-glycosylated. In addition, polypeptides of the invention may also include an initial modified methionine residue, in some cases as a result of host-mediated processes.

The isolated polypeptides of the invention also include variants of those polypeptides described above. The term "variants" is meant to include natural allelic variant polypeptide sequences possessing conservative or nonconservative amino acid substitutions, deletions or insertions. The term "variants" is also meant to include those isolated polypeptide sequences produced by the hand of man, through known mutagenesis techniques or through chemical synthesis methodology. Such man-made variants may include polypeptide sequences possessing conservative or non-conservative amino acid substitutions, deletions or insertions.

Whether a particular amino acid is conservative or non-conservative is well known to those skilled in the art. Conservative amino acid substitutions do not significantly affect the folding or activity of the protein. For exemplary purposes, Table 1 presents a list of conservative amino acid substitutions.

TABLE 1

Conservative Amino Acid Substitutions

| | |
|---|---|
| Aromatic | Phenylalanine |
| | Tryptophan |
| | Tyrosine |
| Hydrophobic | Leucine |
| | Isoleucine |
| | Valine |
| Polar | Glutamine |
| | Asparagine |
| Basic | Arginine |
| | Lysine |
| | Histidine |
| Acidic | Aspartic Acid |
| | Glutamic Acid |
| Small | Alanine |
| | Serine |
| | Threonine |
| | Methionine |
| | Glycine |

Amino acids in the protein of the present invention that are essential for function can be identified by methods known in the art, such as site-directed mutagenesis or alanine-scanning mutagenesis (Cunningham and Wells, *Science* 244:1081–1085 (1989)).

Isolated polypeptide molecules of the invention also include polypeptide sequences that are 95%, 96%, 97%, 98% and 99% identical to the isolated polypeptide molecules described herein. Computer programs such as the BestFit program (Wisconsin Sequence Analysis Package, Version 10 for Unix, Genetics Computer Group, University Research Park, 575 Science Drive, Madison, Wis. 53711) may be used to determine whether any particular polypeptide molecule is at least 95%, 96%, 97%, 98% or 99% identical to the polypeptide sequences disclosed herein or the the polypeptide sequences encoded by the isolated DNA molecule of the deposited clones described herein. BestFit uses the local homology algorithm of Smith and Waterman, *Advances in Applied Mathematics* 2: 482–489 (1981), to find the best segment of homology between two sequences.

By way of example, when a computer alignment program such as BestFit is utilized to determine 95% identity to a reference polypeptide sequence, the percentage of identity is calculated over the full length of the reference polypeptide sequence and gaps in homology of up to 5% of the total number of amino acids in the reference sequence are allowed. Thus, per 100 amino acids analyzed, 95% identity indicates that as many as 5 of 100 amino acids in the subject sequence may vary from the reference polypeptide sequence.

The invention also encompasses fragments of the polypeptide sequences and isolated polypeptide molecules described herein. In a preferred embodiment the invention provides for fragments that are at least 10 amino acids in length. The length of such fragments may be easily defined algebraically. For example, SEQ ID NO:4 provides for an isolated polypeptide molecule that is 754 amino acids in length. A fragment (F4) of SEQ ID NO:4 at least 10 amino acids in length may be defined as F4=10+X, wherein X is defined to be zero or any whole integer from 1 to 744. Similarly, fragments for other isolated polypeptide molecules described herein may be defined as follows: for SEQ ID NO:5 which is 478 amino acids in length, a fragment (F5) of SEQ ID NO:5 at least 10 amino acids in length may be defined as F5=10+X, wherein X is defined to be zero or any whole integer from 1 to 468; and for SEQ ID NO:6 which is 306 amino acids in length, a fragment (F6) of SEQ ID NO:6 at least 10 amino acids in length may be defined as F6=10+X, wherein X is defined to be zero or any whole integer from 1 to 296.

Particularly preferred embodiments of the invention provide isolated polypeptides such as the following: (1) the full length polypeptide the SDH subunit 1 of the invention, encoded by the isolated nucleic acid molecule of SEQ ID NO:1 and identified by SEQ ID NO:4; (2) the full length polypeptide the SDH subunit 2 of the invention, encoded by the isolated nucleic acid molecule of SEQ ID NO:2 and identified by SEQ ID NO:5; (3) the full length polypeptide the SDH subunit 3 of the invention, encoded by the isolated nucleic acid molecule of SEQ ID NO:3 and identified by SEQ ID NO:6; (4) the mature form of the SDH subunit 1 polypeptide of the invention, encoded by the isolated nucleic acid molecule of SEQ ID NO:22 and identified by SEQ ID NO:25; (5) the mature form of the SDH subunit 2 polypeptide of the invention, encoded by the isolated nucleic acid molecule of SEQ ID NO:24 and identified as SEQ ID NO:26; and the mature form of the SDH subunit 3 polypeptide of the invention, encoded by the isolated nucleic acid molecule of SEQ ID NO:23 and identified as SEQ ID NO:27.

The invention also provides a process for producing a polypeptide comprising: (a) growing the host cell containing the isolated nucleic acid molecule of SEQ ID NO:1 or variants thereof; (b) expressing the polypeptide encoded by said isolated nucleic acid molecule; and (c) isolating said polypeptide.

In another embodiment, the invention provides a process for producing a polypeptide comprising: (a) growing the host cell containing the isolated nucleic acid molecule of SEQ ID NO:2 or variants thereof; (b) expressing the polypeptide encoded by said isolated nucleic acid molecule; and (c) isolating said polypeptide.

Another process provided by the invention is for the production of a polypeptide which comprises: (a) growing the host cell containing the isolated nucleic acid molecule of SEQ ID NO:3 or variants thereof; (b) expressing the polypeptide encoded by said isolated nucleic acid molecule; and (c) isolating said polypeptide.

Representative examples of appropriate hosts include, but are not limited to, bacterial cells, such as Gluconobacter, Brevibacterium, Corynebacterim, *E. coli*, Streptomyces, *Salmonella typhimurium*, Acetobacter, Pseudomonas, Pseudogluconobacter, Bacillus and Agrobacterium cells; fungal and yeast organisms including Saccharomyces, Kluyveromyces, Aspergillus and Rhizopus; insect cells such as Drosophila S2 and Spodoptera Sf9 cells; animal cells such as CHO, COS and Bowes melanoma cells; and plant cells. Appropriate culture mediums and conditions for the above-described host cells are known in the art.

The polypeptide may be expressed in a modified form, such as a fusion protein, and may include not only secretion signals, but also additional heterologous functional regions. For instance, a region of additional amino acids, particularly charged amino acids, may be added to the N-terminus of the polypeptide to improve stability and persistence in the host cell, during purification, or during subsequent handling and storage. Also, peptide moieties may be added to the polypeptide to facilitate purification. Such regions may be removed prior to final preparation of the polypeptide. The addition of peptide moieties to polypeptides to engender secretion or excretion, to improve stability and to facilitate purification, among others, are familiar and routine techniques in the art.

Polypeptides of the invention may be recovered and purified from recombinant cell cultures by well-known methods including ammonium sulfate or ethanol precipitation, acid extraction, anion or cation exchange chromatography, phosphocellulose chromatography, hydrophobic interaction chromatography, affinity chromatography, hydroxylapatite chromatography and lectin chromatography. Most preferably, high performance liquid chromatography ("HPLC") is employed for purification.

5. Production of L-Sorbose and 2-Keto-L-Gulonic Acid

The invention provides processes for the production of L-sorbose and 2-keto-L-gulonic acid, which are useful in the production of vitamin C.

In one embodiment, the invention provides a process for the production of L-sorbose from D-sorbitol comprising: (a) transforming a host cell with at least one isolated nucleotide sequence selected from the group consisting of: (i) a polynucleotide comprising the polynucleotide sequence of SEQ ID NO:1; (ii) a polynucleotide comprising the polynucleotide sequence of SEQ ID NO:2; and (iii) a polynucleotide comprising the polynucleotide sequence of SEQ ID NO: 3; and (b) selecting and propagating said transformed host cell.

In another embodiment, the invention provides a process for the production of 2-keto-L-gulonic acid comprising: (a) transforming a host cell with at least one isolated nucleotide sequence selected from the group consisting of: (i) a polynucleotide comprising the polynucleotide sequence of SEQ ID NO:1; (ii) a polynucleotide comprising the polynucleotide sequence of SEQ ID NO:2; and (iii) a polynucleotide comprising the polynucleotide sequence of SEQ ID NO: 3; and (b) selecting and propagating said transformed host cell.

Suitable bacteria for use as host cells in the processes provided herein for the production of L-sorbose and 2-keto-L-gulonic acid are known to those skilled in the art. Such bacteria include, but are not limited to, *Escherichia coli*, Brevibacterium, Corynebacterium, Gluconobacter, Acetobacter, Pseudomonas and Pseudogluconobacter.

Other host cells for expression of the SDH enzyme of the invention include: strains identified in U.S. Pat. No. 5,834,231; *Glucanobacter oxydans* DSM 4025 (U.S. Pat. No. 4,960,695); *Gluconobactor oxydans* TIOO (*Appl. Environ. Microbiol.* 63:454–460 (1997)); *Pseudogluconobacter saccharoketogenes* IFO 14464 (European Patent No. 221 707); *Pseudomonas sorbosoxidans* (U.S. Pat. No. 4,933,289); and *Acetobacter liquefaciens* IFO 12258 (*Appl Environ. Microbiol.* 61:413–420 (1995)).

In other embodiments of the invention, a variety of fermentation techniques known in the art may be employed in processes of the invention drawn to the production of L-sorbose and 2-keto-L-gulonic acid. Generally, L-sorbose and 2-keto-L-gulonic acid may be produced by fermentation processes such as the batch type or of the fed-batch type. In batch type fermentations, all nutrients are added at the beginning of the fermentation. In fed-batch or extended fed-batch type fermentations one or a number of nutrients are continuously supplied to the culture, right from the beginning of the fermentation or after the culture has reached a certain age, or when the nutrient(s) which are fed were exhausted from the culture fluid. A variant of the extended batch of fed-batch type fermentation is the repeated fed-batch or fill-and-draw fermentation, where part of the contents of the fermenter is removed at some time, for instance when the fermenter is full, while feeding of a nutrient is continued. In this way a fermentation can be extended for a longer time.

Another type of fermentation, the continuous fermentation or chemostat culture, uses continuous feeding of a complete medium, while culture fluid is continuously or semi-continuously withdrawn in such a way that the volume of the broth in the fermenter remains approximately constant. A continuous fermentation can in principle be maintained for an infinite time.

In a batch fermentation an organism grows until one of the essential nutrients in the medium becomes exhausted, or until fermentation conditions become unfavorable (e.g. the pH decreases to a value inhibitory for microbial growth). In fed-batch fermentations measures are normally taken to maintain favorable growth conditions, e.g. by using pH control, and exhaustion of one or more essential nutrients is prevented by feeding these nutrient(s) to the culture. The microorganism will continue to grow, at a growth rate dictated by the rate of nutrient feed. Generally a single nutrient, very often the carbon source, will become limiting for growth. The same principle applies for a continuous fermentation, usually one nutrient in the medium feed is limiting, all other nutrients are in excess. The limiting nutrient will be present in the culture fluid at a very low concentration, often unmeasurably low. Different types of nutrient limitation can be employed. Carbon source limitation is most often used. Other examples are limitation by the nitrogen source, limitation by oxygen, limitation by a specific nutrient such as a vitamin or an amino acid (in case the microorganism is auxotrophic for such a compound), limitation by sulphur and limitation by phosphorous.

Illustrative examples of suitable supplemental carbon sources include, but are not limited to: other carbohydrates, such as glucose, fructose, mannitol, starch or starch hydrolysate, cellulose hydrolysate and molasses; organic acids, such as acetic acid, propionic acid, lactic acid, formic acid, malic acid, citric acid, and fumaric acid; and alcohols, such as glycerol.

Illustrative examples of suitable nitrogen sources include, but are not limited to: ammonia, including ammonia gas and aqueous ammonia; ammonium salts of inorganic or organic acids, such as ammonium chloride, ammonium nitrate, ammonium phosphate, ammonium sulfate and ammonium acetate; urea; nitrate or nitrite salts, and other nitrogen-containing materials, including amino acids as either pure or crude preparations, meat extract, peptone, fish meal, fish hydrolysate, corn steep liquor, casein hydrolysate, soybean cake hydrolysate, yeast extract, dried yeast, ethanol-yeast distillate, soybean flour, cottonseed meal, and the like.

Illustrative examples of suitable inorganic salts include, but are not limited to: salts of potassium, calcium, sodium, magnesium, manganese, iron, cobalt, zinc, copper and other trace elements, and phosphoric acid.

Illustrative examples of appropriate trace nutrients, growth factors, and the like include, but are not limited to: coenzyme A, pantothenic acid, biotin, thiamine, riboflavin, flavine mononucleotide, flavine adenine dinucleotide, other vitamins, amino acids such as cysteine, sodium thiosulfate, p-aminobenzoic acid, niacinamide, and the like, either as pure or partially purified chemical compounds or as present in natural materials. Cultivation of the inventive microorganism strain may be accomplished using any of the submerged fermentation techniques known to those skilled in the art, such as airlift, traditional sparged-agitated designs, or in shaking culture.

The culture conditions employed, including temperature, pH, aeration rate, agitation rate, culture duration, and the like, may be determined empirically by one of skill in the art to maximize L-sorbose and 2-keto-L-gulonic acid production. The selection of specific culture conditions depends upon factors such as the particular inventive microorganism strain employed, medium composition and type, culture technique, and similar considerations.

Illustrative examples of suitable methods for recovering 2-KLG are described in U.S. Pat. Nos. 5,474,924; 5,312,741; 4,960,695; 4,935,359; 4,877,735; 4,933,289; 4,892,823; 3,043,749; 3,912,592; 3,907,639 and 3,234,105.

According to one such method, the microorganisms are first removed from the culture broth by known methods, such as centrifugation or filtration, and the resulting solution concentrated in vacuo. Crystalline 2-KGL is then recovered by filtration and, if desired, purified by recrystallization. Similarly, 2-KGL can be recovered using such known methods as the use of ion-exchange resins, solvent extraction, precipitation, salting out and the like.

When 2-KGL is recovered as a free acid, it can be converted to a salt, as desired, with sodium, potassium, calcium, ammonium or similar cations using conventional methods. Alternatively, when 2-KGL is recovered as a salt, it can be converted to its free form or to a different salt using conventional methods.

All patents and publications referred to herein are expressly incorporated by reference. Having now generally described the invention, the same will be more readily understood through reference to the following Examples which are provided by way of illustration, and are not intended to be limiting of the present invention, unless specified.

EXAMPLES

Example 1

Isolation and Characterization of SDH from *G. suboxydans* KCTC 2111

An improved method for the purification of the pyrroloquinoline quinone (PQQ)-dependent SDH of the invention from *G. suboxydans* KCTC 2111 is presented. Improvements over the original purification scheme (Choi, E. S. et al., *FEMS Microbiol. Lett.*, 125:45 (1995)) relate to greater subunit resolution and improved stability of enzyme activity.

Step 1: Cultivation of *G. suboxydans* KCTC 2111

*G. suboxydans* KCTC 21 11 was inoculated into 5 ml of SYP medium (5% D-sorbitol, 1% BactoPeptone and 0.5% yeast extract) and incubated at 30° C. for 20 hours. One milliliter (ml) of this culture were transferred to 50 ml of the same medium in a 500 ml flask and cultivated at 30° C. for 20 hours on a rotary shaker (180 rpm). The culture thus prepared was used as an inoculum for a 5 L jar fermentor containing 3 L of the same medium, and the 3 L culture was grown to early stationary phase.

Step 2: Preparation of the Membrane Fraction

Cells were harvested by centrifugation at 12,000 g for 10 min, washed once with 10 mM sodium acetate buffer (pH 5.0) and disrupted with glass beads (0.1 mm in diameter) in a bead beater (Edmund Buhler, Vi 4) for 90 sec at 4° C. The homogenate thus prepared was centriftiged at 12,000 g for 5 min to remove cell debris and glass beads. The resulting supernatant was centrifuged at 100,000 g for 60 min, and a crude membrane fraction was obtained as a precipitate.

Step 3: Solubilization of SDH from the Membrane Fraction

The crude membrane fraction was resuspended at 40 mg of protein per ml and solubilized with 1.5% n-octyl glucoside by stirring for 2 hours at 4° C. The resultant suspension was centrifuged at 12,000 g for 10 min to give a supernatant, designated as the solubilized SDH fraction. All the solutions employed in the purification procedures contained 0.75% n-octyl glucoside.

Step 4: Enzyme Activity Assay

Enzyme activity was assayed spectrophotometrically using 2,6-dichlorophenol indophenol (DCIP) as an artificial electron acceptor and phenazine methosulphate (PMS) as an electron mediator. The reaction mixture contained 50 mM sodium acetate buffer (pH 5.0), 10 mM $MgCl_2$, 5 mM $CaCl_2$, 5 mM KCN, 0.1 mM PMS, 0.12 mM DCIP, 250 mM D-sorbitol, 0.75% n-octyl glucoside and enzyme solution in a total volume of 1.0 ml. The molar extinction coefficient of $\epsilon=5,600$ cm$^{-1}$ M$^{-1}$ for DCIP at pH 5.0 was employed. One unit of enzyme activity was defined as the amount of enzyme catalyzing reduction of 1 μmol of DCIP per min.

Enzyme activity was determined also by the Ferric-Dupanol method (Wood, W.A. et al., *Meth. Enzymol.* 5:287 (1962)) for the reconstituted subunits described in step 6 of Example 1. Subunit proteins were preincubated either singly or in different combinations for 5 min at 25° C. The reaction was started by the addition of 10 mM (final concentration) of potassium ferricyanide and 250 mM (final concentration) D-sorbitol. After an appropriate time, the reaction was stopped by adding the ferric sulfate-Dupanol solution ($Fe_2(SO_4)_3 \cdot nH_2O$ 5 g/L, Dupanol (sodium lauryl sulfate) 3 g/L and 85% phosphoric acid 95 ml/L), and the absorbance of the Prussian color was determined at 660 nm in a spectrophotometer.

Step 5: Ion-exchange Chromatography

The solubilized fraction was loaded onto a CM-TSK 650 (S) (Merck) column (2.5×20 cm) equilibrated with 10 mM sodium acetate (pH 5.0). The CM-TSK column was eluted with a linear gradient (from 10 mM to 500 mM) of sodium acetate. Active fractions were pooled and concentrated by ultrafiltration using a membrane filter (Amicon, YM 10) and loaded onto a DEAE-TSK 650 (S) (Merck) column (2.5×20 cm). The DEAE-TSK column was eluted isocratically with a 10 mM sodium acetate buffer of either pH 5.0 or pH 6.0.

Figure 1B:
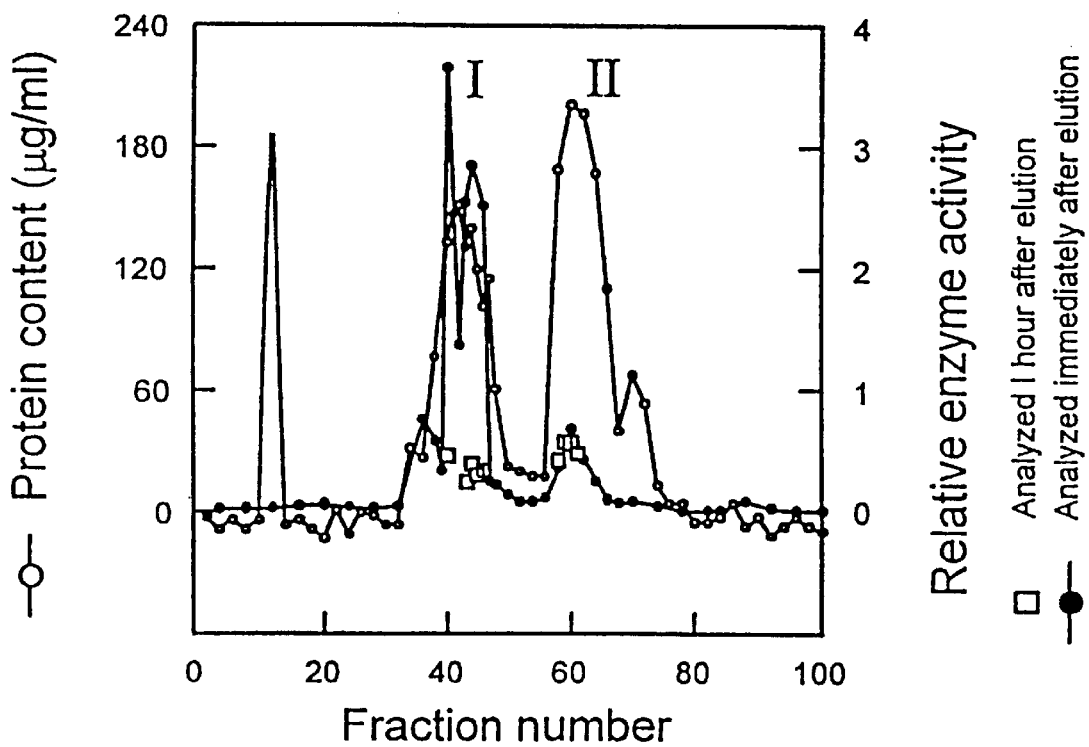

As shown in FIG. 1, when eluted at pH 6.0 (FIG. 1-B), the resolution of the activity peaks was much higher than with an elution at pH 5.0 (FIG. 1-A), and the enzyme activity peaks I and II were completely separated. When the enzyme activity of the fractions was measured immediately after the elution and one hour after the elution, it was found that the enzyme activity of the fractions in peaks I and II eluting together at pH 5.0 did not differ signficantly with time. In the case of the fractions in peaks I and II eluting separately at pH 6.0, however, the enzyme activity in peak I decreased to less than one tenth of the original value within one hour after the elution, whereas the enzyme activity in the peak II remained unchanged.

Figure 2A:
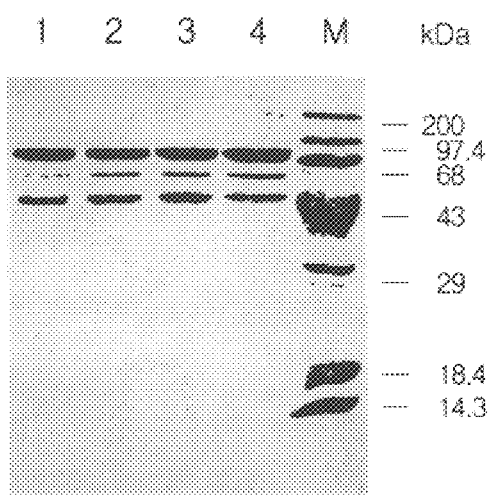
FIG. 2 presents SDS-PAGE analysis of peak I (A) and peak II fractions (B) separated by DEAE-TSK column chromatography.
Figure 2B:
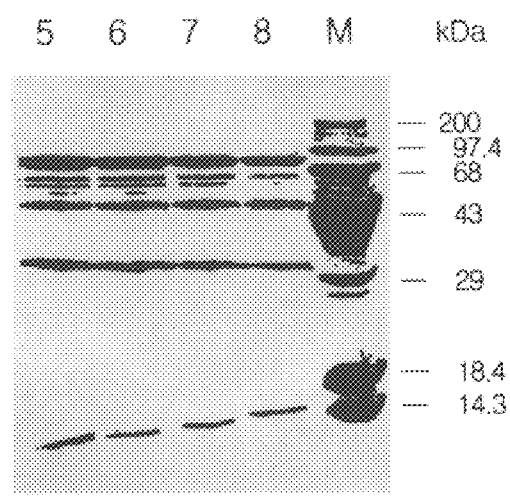

Fractions containing peaks I and II eluted at pH 6.0 on DEAE-TSK colunn were analyzed by SDS-PAGE (Laemmli, U. K., *Nature*, 227, 680 (1970)) (FIG. 2). FIG. 2-A shows fractions of peak I. Column M shows standard molecular weight markers. As shown in columns 1 through 4, the 75 kDa first subunit band and the 50 kDa second subunit band could be observed but the 29 kDa third subunit band was not observed. In this case, one hour after elution, the enzyme activity was reduced by more than ten fold. FIG. 2-B shows the fractions of peak II. Column M shows standard molecular weight markers. As shown in columns 5 through 8, it was observed that fractions of peak II contained the 29 kDa third subunit band in addition to the 75 kDa and 50 kDa subunits. This observation indicated that the 29 kDa third subunit might play an important role in the stability of SDH.

Step 6: SDH Reconstitution with Different Subunits

Since the increase of the pH of the elution buffer from 5.0 to 6.0 during DEAE column chromatography increased the resolution of the chromatographic peaks, the pH of the elution buffer was further increased to pH 6.5. Partially purified SDH provided by CM-TSK 650 (S) column chromatography as described in step 5 of Example 1 was loaded onto DEAE-TSK 650 (S) column (2.5×16.5 cm) pre-equilibrated with 20 mM sodium phosphate buffer (pH 6.5), and the column was isocratically eluted with 180 ml of the same buffer followed by a gradient elution with 160 ml each of 20 mM and 500 mM of sodium phosphate buffer (pH 6.5). Column fractions were analyzed by SDS-PAGE.

Figure 3:
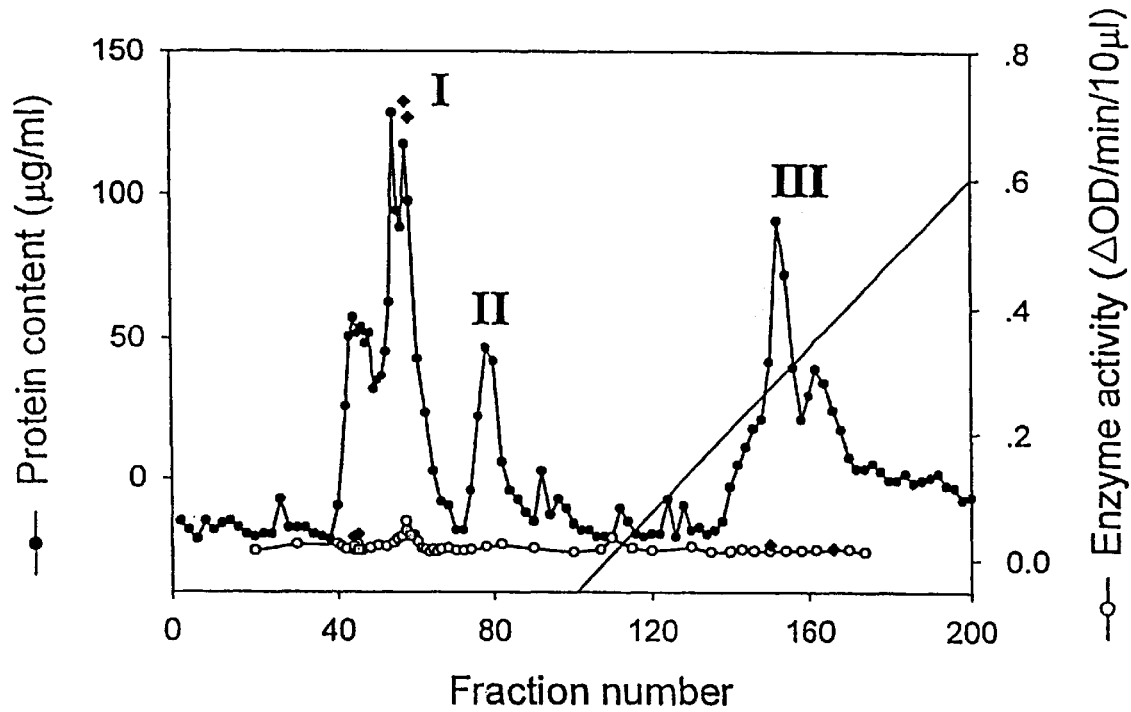
FIG. 3 presents DEAE-TSK column chromatography using a sodium phosphate buffer of pH 6.5.
Figure 4:
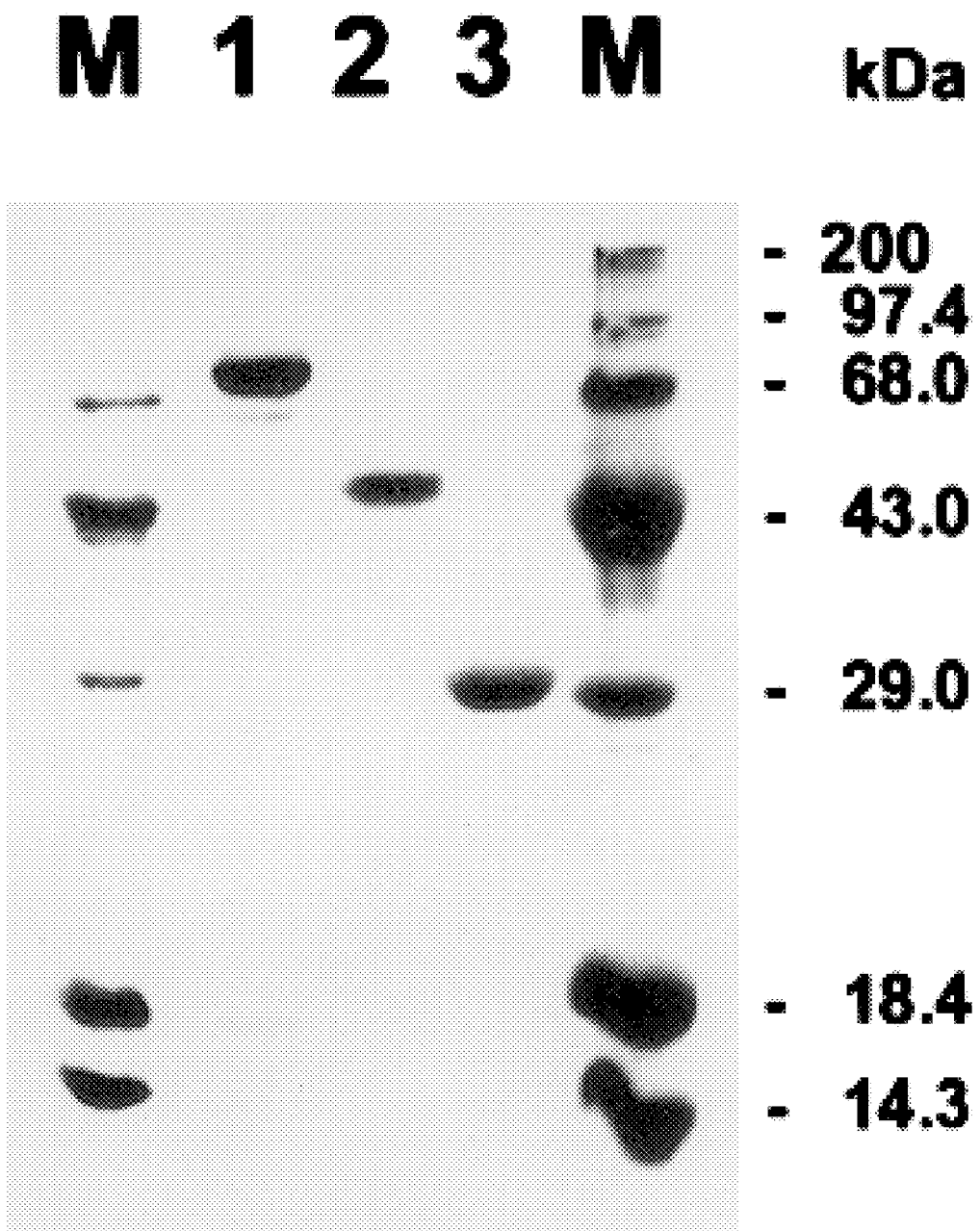
FIG. 4 presents SDS-PAGE analysis of column fractions of peak I (lane 1), peak II (lane 3) and peak III (lane 2) separated by DEAE-TSK column chromatography at pH 6.5. Lane M denotes molecular weight standard markers.

As shown FIG. 3, the first subunit of 75 kDa eluted first (peak I) followed by the third subunit of 29 kDa (peak II) during the isocratic elution, and the second subunit of 50 kDa eluted later during the gradient elution (peak III). As shown in FIG. 4, the SDS-PAGE analysis of the three peaks indicated that the three subunits were essentially pure and completely separated from each other.

Since the three subunits could be purified and separated into individual species under non-denaturing conditions, reconstitution experiments were conducted to determine the role of each subunit for catalytic activity of the SDH enzyme. Approximately 100 pmoles of each subunit obtained from the DEAE column by elution at pH 6.5 were preincubated either singly or in different combinations and assayed for the enzyme activity by Ferric-Dupanol method as described in step 4 of Example 1 (Table 2). Each subunit alone showed a very low level of activity. When the first and the second subunits were reconstituted, enzyme activity increased by two times compared with the first subunit alone. When the third subunit was added to the first subunit, and to the mixture of the first and the second subunits, the enzyme activity increased by about 30 and 20 times, respectively, These results indicated that the third subunit plays an important role for the catalytic activity of SDH as well as the stability of the enzyme.

TABLE 2

| Subunit (kDa) | SDH enzyme activity ($OD_{660}$) |
| --- | --- |
| 75 | 0.029 |
| 50 | 0.002 |
| 29 | 0.004 |
| 75 + 50 | 0.051 |
| 75 + 29 | 0.944 |
| 75 + 50 + 29 | 0.692 |

Example 2

Determination of the N-terminal Amino Acid Sequences of the SHD Subunits

The purified SDH prepared in Example 1 was subjected to SDS-PAGE (12.5% gel), and the separated proteins were electroblotted onto apolyvinylidene difluoride (PVDF) membrane (Bollag, D. M. and Edelstein, S. J., *Protein Methods*, Wiley-Liss, Inc.,8(1991)). After visualization with ponceau S stain, the section of membrane containing each SDH subunit was cut into pieces, and the membrane pieces for each subunit were applied directly to an amino acid sequence analyzer (Applied Biosystems, Model 477A) for N-terminal amino acid sequence analysis.

The resultant data for the first and the third subunits are shown in Table 3 (SEQ ID Nos:9 and 11). The N-terminal amino acid sequence of the second subunit could not be obtained, most likely because of a blocked N-terminus. A similar finding of ablocked N-terminus was reported for the cytochrome c subunit of the alcohol dehydrogenase complex of another acetic acid bacterium, *Acetobacter pasteurianus* (Takemura, H. et al., *J Bacteriol.* 175, 21, 6857 (1993)), where the blockage of the N-terminus was ascribed to the modification of glutamate residue at the N-terminus to a pyroglutamate residue, which is recalcitrant to the Edman degradation during N-terminal amino acid sequencing.

Therefore, in order to obtain N-terminal sequence for the second subunit of purified SDH, the isolated SDH protein was first treated with pyroglutamate aminopeptidase to release the potentially blocked N-terminus. Briefly, about 50 pg of purified SDH from Example 1 was dissolved in a digestion buffer (100 mM sodium phosphate buffer, 10 mM EDTA, 5 mM dithiothreitol and 5% (v/v) glycerol, pH 8.0) and incubated with 3.75 μg of pyroglutarnate aminopeptidase (Boehringer Mannheim) at 4° C. for 18 hours, followed by an additional incubation for 4 hours at 25° C. After incubation, the reaction mixture was subjected to SDS-PAGE, electroblotted onto a PVDF membrane, and the second subunit band on the membrane was excised and analyzed for the N-terminal amino acid sequence as described above. Ten residues of N-terminal amino acid sequence is shown in Table 3 as Sequence ID. No:10.

TABLE 3

| Sequence ID No. | N-terminal amino acid sequence |
| --- | --- |
| SEQ ID NO: 9 | EDTGTAITNADQHPG |
| SEQ ID NO: 10 | DADDALIQRG |
| SEQ ID NO: 11 | AGTPLKIGVSFQEMNNPYFVTMKDA |

Example 3
Determination of Internal Amino Acid Sequence for the Third Subunit

Figure 5:
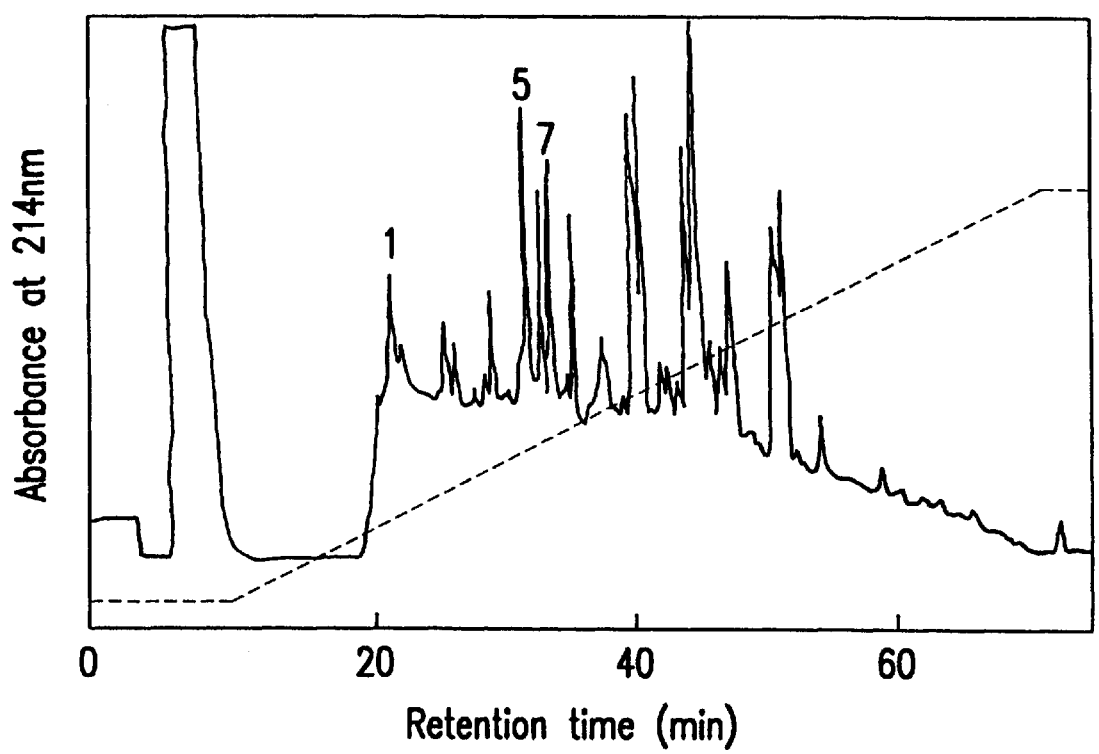
FIG. 5 presents an HPLC chromatogram of a tryptic digest of peak II protein from DEAE-TSK column chromatography at pH 6.5. The dotted line indicates the concentration gradient of acetonitrile in the mobile phase.

For the third subunit, internal amino acid sequences were also determined in addition to the N-terminal amino acid sequence for the facilitated cloning of the corresponding gene. About 7 μg of the third subunit protein isolated as described in step 6 of Example 1, was digested with trypsin (Boehringer Mannheim) as previously described (Matsudaira, P. T., *A Practical Guide to Protein and Pept Purification for Mcrosequencing Academic Press* p. 37 (1989)). The tryptic digest was separated by HPLC using a Brownlee SPHERI-5 RP 18 column (0.2×22 cm), and the column was eluted with a linear gradient of 15–70% acetonitrile for 60 minutes at 210 microliter/minute. The elution was monitored at 214 nrn, and the well separated three peptide peaks were collected (designated 1, 5 and 7 in FIG. 5) and analyzed for their amino acid sequence as described in (Example 2). The internal amino acid sequences for the peaks, 1, 5 and 7 are shown below in Table 4 (SEQ ID NO: 12, 13, and 14), respectively.

TABLE 4

| Sequence ID No. | Internal amino acid sequence |
| --- | --- |
| SEQ ID NO: 12 | HSDIK |
| SEQ ID NO: 13 | NYDAGFK |
| SEQ ID NO: 14 | KWGAGVPK |

Example 4
Primer Design and Isolation of a 1.53 kb DNA Fragment Containing a Portion of the SDH Gene Based on the N-terminal amino acid sequence of the first subunit (SEQ ID NO:9), two degenerate primers, primer 1 (5'- CCGGAATTC GAA(G) GAT(C) ACI GGI ACI GC-3') (SEQ ID NO:15) and primer 2 (5'-ATT(C,A) ACI AAT(C) GCI GAT(C) CAAG) CAT(C) CC-3')(SEQ ID NO:16), were synthesized.

The genomic DNA isolated from *G. suboxydans* KCTC 2111 using the method of Takeda and Shimizu (Takeda and Shimizu, *J Ferm. Bioeng.*, 72:1 (1991)) was partially digested with BamHI. The plasmid pBluescript SK (Stratagene) was restricted with Nael and BamHI and the BamHI partial digest of genomic DNA was ligated to the BamHI site of the plasmid.

Thirty cycles of polymerase chain reaction (PCR) was performed in accordance with the single specific primer PCR (SSP-PCR) method (White, B., SSP-PCR and genome walking, in *Method in Mol. Biol.*, PCR protocols, Humana Press, 15:339 (1993)) to isolate a clone (#SDH2-1) 1.53 kb in size.

The ligation reaction mixture prepared above was amplified with a gene specific primer, the primer 1, and the T7 primer of the vector. Although the generic T7 primer anneals to the ends of all ligated fragments, the resulting products increase only linearly. However, simultaneous annealing of the gene specific primer 1 and T7 primer to the specific product results in exponential amplification of the specific primary product. Secondary PCR carried out with a nested primer, the gene specific primer 2, and the T7 primer generated a specific secondary product, which confirmed the specificity of the primary PCR.

The PCR product was ligated to plasmid pT7 Blue (Novagen) and transformed into *Escherichia coli* DH5a by SEM protocol (Inoue, H. et al., *Gene*, 96:23 (1990)). Transformants were cultivated in an LB medium (1% Bacto-Tryptone, 0.5% yeast extract and 1% NaCl) supplemented with 100 μg/ml of ampicillin. Subsequently, the plasmid was extracted by alkaline lysis method (Sambrook, J. et al., *Molecular Cloning*, CSH Press, p. 125 (1988)).

PCR with primer 1 or primer 2 together with the T7 primer using this plasmid as a template yielded a positive reaction. Partial nucleotide sequencing of #SDH2-1 fragment further confirmed that the derived amino acid sequence downstream of the primer 1 binding site matched with the experimentally determined N-terminal amino acid sequence. However, #SDH2-1 contained only a part of the first subunit gene.

Example 5
Isolation of Lambda GEM5-1 Clone Containing SDH Subunit Genes Using the 1.53 kb DNA Fragment as a Probe The #SDH2-1 isolated in Example 4 was labeled with DIG Labeling and Detection Kit (The DIG System User's Guide for Filter Hybridization. p. 6–9, Boehringer Mannheim (1993)).

To construct a genomic DNA library of G. suboxydans KCTC 2111, the genomic DNA isolated from G. suboxydans KCTC 2111 using the method described in Example 4 was partially digested with Sau3AI. Partially digested DNA was electrophoresed in a 0.8% agarose gel and the DNA of 15 to 23 kb in size was eluted using QLAEX II Gel Extraction Kit (QIAGEN). The eluted DNA was then ligated into the BamHI site of Lambda GEM-11 vector (Promega). The ligation mixture was packaged into phage lambda particles using the Packagene In Vitro Packaging System (Promega) according to the instruction manual. *E. coli* LE392 cells were grown in TB medium (1% Bacto-Tryptone and 0.5% NaCl) supplemented with 0.2% maltose and 10 mM $MgSO_4$, at 30° C. and stored at 4° C. when the $OD_{600}$ had reached 0.6. The packaging mixture was added to the cell suspension, and the mixture was incubated for 30 min at 37° C. to allow infection. To this mixture, 3 ml of molten (45° C.) TB top agar (0.8% Bacto-Agar in T13 medium containing 10 mM $MgSO_4$) was added, vortexed gently and immediately poured onto LB plates. The plates were incubated inverted at 37° C. overnight.

The lambda phage plaques were immobilized on nylon membranes (Amersham) and the membranes were prehybridized in a hybridization oven (Hybaid) using a prehybridization solution (5×SSC, 1% (w/v) blocking reagent, 0.1% N-lauroylsarcosine, 0.02% SDS and 50% (v/v) formamide) at 42° C. for 3 hours. Then the membranes were hybridized using a hybridization solution (DIG-labeled #SDH2-1 probe diluted in the prehybridization solution) at 42° C. for 16 hours. Eleven plaques among about 20,000 plaques of the lambda phage gave positive signals by plaque hybridization (The DIG System User's Guide for Filter Hybridization. Boehringer Mannheim (1993)) with the DIG-labeled #SDH2-1 probe.

Figure 6:
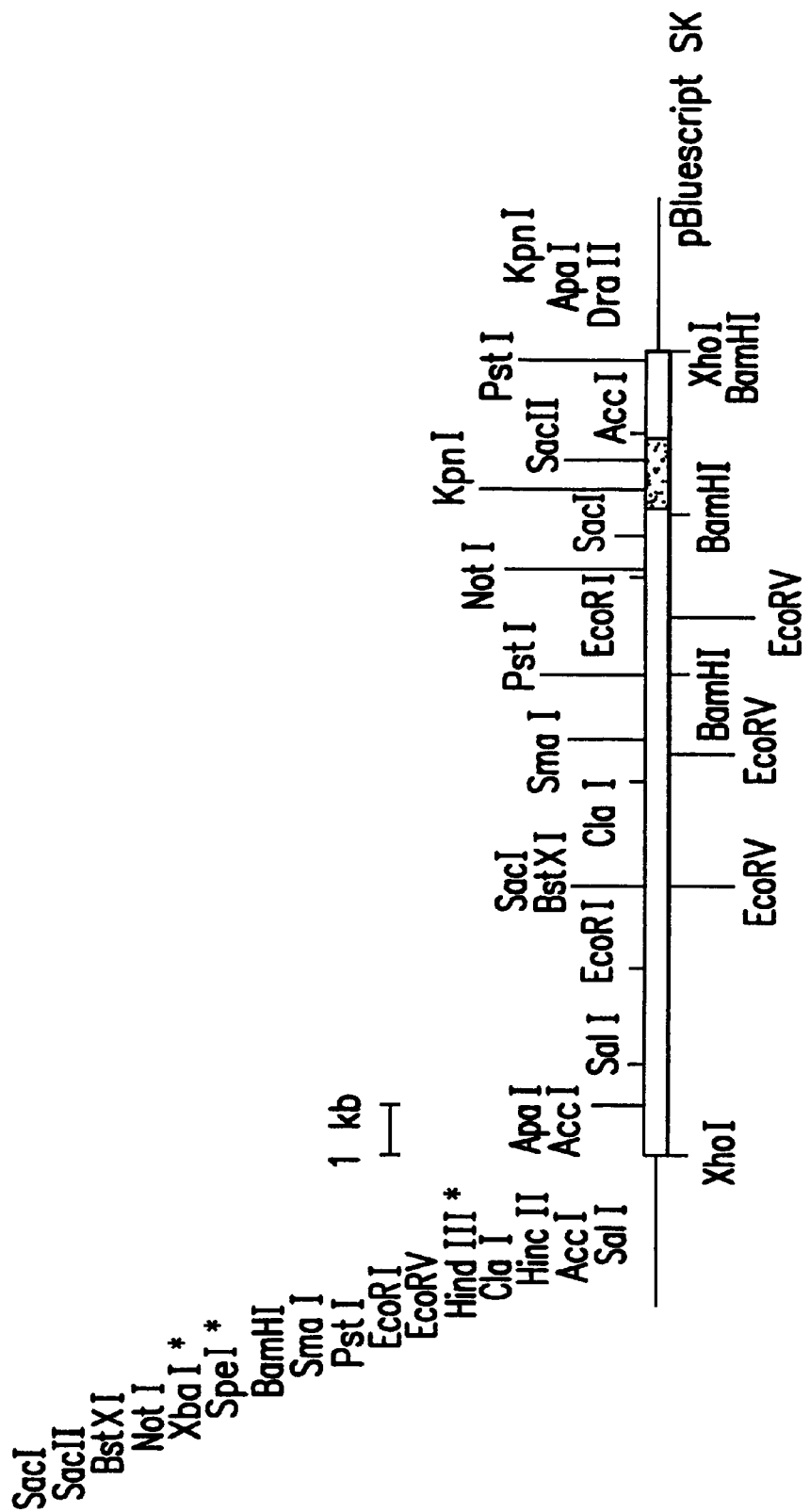
FIG. 6 presents a restriction enzyme map of the Lambda GEM 5- 1. The 1.53 kb DNA fragment (#SDH 2-1) used as probe is shown as solid bar.

The lambda DNAs were isolated from positive lambda clones and purified with Lambda DNA Purification Kit (Stratagene). The isolated lambda DNAs were digested with BamHl and subjected to a 0.7% agarose gel electrophoresis. The DNA fragments separated on the gel were transferred onto a nylon membrane and analyzed again by, Southern hybridization with #SDH2-1 as probe under the same condition as described above. A clone which gave a positive signal was selected, and the insert DNA of 15 kb was excised with XhoI from this clone and subsequently cloned into the XhoI site of pbluescript SK give Lambda GEM 5-1. The Lambda GEM 5-1 clone was mapped by digestion with several different restriction enzymes. FIG. 6 presents the restriction enzyme map of Lambda GEM 5-1.

Figure 7:
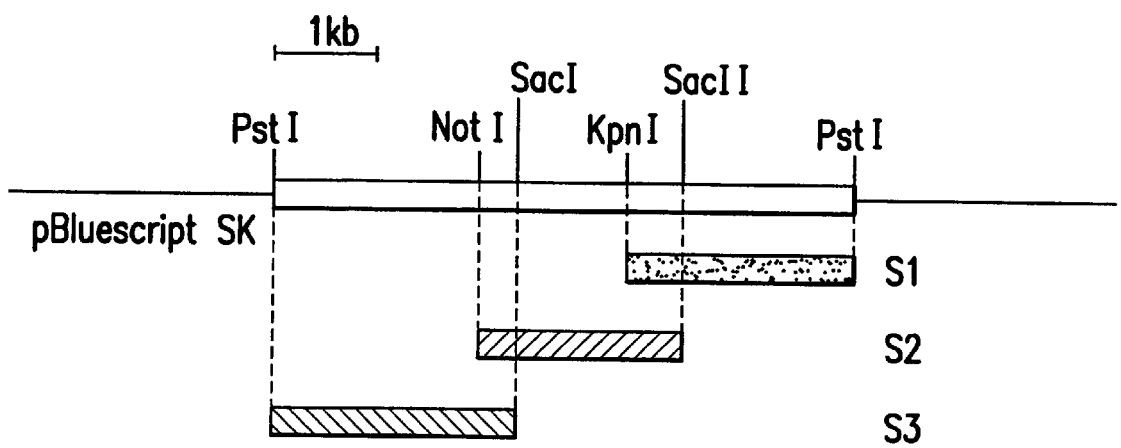
FIG. 7 presents the locations of SI, S2 and S3 DNA fragments generated with different sets of restriction enzymes from 5.7 kb Pstl fragment of Lambda GEM 5-1.

Example 6
Determination of the Nucleotide Sequence of the 5.7 kb Pstl Fragment in the Lambda GEM 5-1 Clone The positive clone, Lambda GEM 5-1, obtained in Example 5 was mapped with several different restriction enzymes and analyzed by Southern hybridization as described in Example 5. A 5.7 kb Pstl fragment hybridizing with #SDH2-1 was subcloned, and the nucleotide sequence was determined. To make the DNA sequencing simpler, three overlapping subclones, S1, S2 and S3, were constructed using restriction enzyme sets, KpnI-Pstl, NotI-SacII and Pstl-SacI, respectively, as shown in FIG. 7. A set of deletion clones was prepared for each subclone using Exo III-Mungbean Deletion Kit (Stratagene). The nucleotide sequencing reaction was done by Dye Terminator Cycle Sequencing Ready Reaction Kit (Applied Biosystems), and the sequence was determined in an automatic DNA sequencer (Applied Biosystems, Model 373A).

FIG. 8 shows the nucleotide sequence of 4,830 bp in the 5.7 kb Pstl fragment (SEQ ID NO:7). The sequenced DNA contains two open reading frames (ORFs) of 2,265 and 1,437 nucleotides. The first ORF encodes the first subunit. The first subunit gene is preceded by a Shine-Dalgarno sequence, "AGGA" positioned at 651–654 bp. The 34 amino acid signal sequence of the first subunit is positioned at 665–766 bp of SEQ ID NO:7. The coding sequence of the mature part of the first subunit protein is positioned at 767–2,929 bp of SEQ ID NO:7, which encodes a 720 amino acid polypeptide whose derived N-terminal amino acid sequence is in perfect agreement with 15 amino acid residues obtained by N-terminal amino sequence analysis.

The first ORF was followed by the second ORF, the two ORF's being interrupted by a short intergenic region. The second ORF encodes the second subunit. The Shine-Dalgamo sequence (AGGA) of the second subunit gene is found at 2,950–2,953 bp SEQ ID NO:8, and the structural gene is positioned at 2,964–4,400 bp of SEQ ID NO:8. The second subunit gene encodes a 478 amino acid polypeptide, including a signal sequence of 36 amino acids. The derived amino acid sequence of the mature polypeptide showed a perfect match with the experimentally obtained sequence for the sample treated with pyroglutamate aminopeptidase. Downstream of the stop codon of the second subunit gene, inverted repeat sequences are found.

The calculated molecular weights of the mature proteins of the first and the second subunit are 79 kDa and 48 kDa, respectively, which are in good agreement with the experimental values of 75 kDa and 50 kDa, respectively, as determined by SDS-PAGE.

In addition it was also found that signature PQQ-binding sequences, consensus sequences appearing characteristically in the amino- and carboxy-terminals of PQQ-dependent dehydrogenases, are present in the first subunit gene. In Table 5, the signature PQQ-binding sequence in amino-terminal part is shown as Sequence ID NO:17, and the signature sequence existing in the carboxy-terminal part is shown as Sequence ID No:18 (Here, X represents an arbitrary amino acid.). The amino-terminal signature sequence occurs at position 812–898 bp, and the carboxy-terminal signature sequence occurs at position 1,490–1,555 bp. These data provide additional evidence that the first subunit contains pyrroloquinoline quinone (PQQ) as cofactor.

TABLE 5

| | |
|---|---|
| [D/E/N]-W-X-X-X-G-[R/K]-X-X-X-X-X-X-[F/Y/W]-S-X-X-X-X-[L/I/V/M]-X-X-X-N-X-X-L-[R/K] | [SEQ ID NO: 17] |
| W-X-X-X-X-Y-D-X-X-X-[D/N]-[L/I/V/M/F/Y]-[L/I/V/M/F/Y]-[L/I/N/M/F/Y]-[L/I/V/M/F/Y]-X-X-G-X-X-[S/T/A]-P | [SEQ ID NO: 18] |

In addition, it was also discovered that a single heme-binding sequence occured at position 2,612–2,626 bp in the first subunit gene (SEQ ID NO:19 in Table 6 below), and three heme-binding sequence occurred at the following positions: 3,129–3,143; 3,573–3,587 and 3,981–3,995 bp in the second subunit gene (Here, $X_A$ represents an arbitrary amino acid. $X_B$, is an arbitrary amino acid different from $X_A$.).

TABLE 6

| | |
|---|---|
| C-$X_A$-$X_B$-C-H | [SEQ ID NO: 19] |

A database search for homologous sequences determined that the DNA sequence of the first subunit gene showed a great degree of similarity to many dehydrogenases containing pyrroloquinoline quinone (PQQ) as cofactor: In particular, the alcohol dehydrogenases of *Acetobacter polyoxogenes* (Tamaki, T. et al., Biochim. Biophys. Acta, 1088, 292 (1991)) and *Acetobacter aceti* (Inoue, T. et al., *J Bacteriol*, 171, 3115 (1989)) are 77% and 70% identical, respectively, to the first subunit gene. A search of the database with the second subunit gene provided the greatest degree of similarity, matching the cytochrome c of *G. suboxydans* IFO 12528 (Takeda and Shimizu, *J Ferm. Bioeng.*, 72:1 (1991)) with a nucleotide sequence identity of 83% and an amino acid sequence identity of 88%.

Example 7
Primer Design and PCR Cloning of 320 bp DNA Fragment Containing a Portion of the Third Subunit Gene The nucleotide sequence analysis of the first and the second subunit genes described in Example 6 indicated that the isolated operon clone did not contain the third subunit gene. Further sequencing of the 5' and 3' flanking regions also failed to show the presence of the third subunit. Therefore, in order to isolate the gene encoding the third subunit, degenerate primers were synthesize based on the amino acid sequence information, in order to generate by PCR a short DNA fragment containing a portion of third subunit gene for use as probe.

Based on the N-terminal amino acid sequence (SEQ ID NO:1) of the mature third subunit protein obtained in Example 2 and one of the internal amino acid sequence (SEQ ID NO:13) of the tryptic peptides obtained in Example 3, two degenerate primers, primer 3 (5'-GGGAATTC TTT (C) CAA(G) GAA(G) ATG AAT(C) AA-3') (SEQ ID NO:20) and primer 4(5'-GGGAATTC TT GAA A(G)CC NGC A(G)TC A(G)TA-3')(SEQ ID NO:21), respectively, were synthesized.

A PCR reaction was done with primers 3 and 4 using genomic DNA of G. suboxydans KCTC 21 1 1 prepared by the method of Takeda and Shimizu (Takeda and Shimizu, J. Ferm. Bioeng., 72 1 (1991)) as template. The reaction generated a 320 bp DNA fragement. This 320 bp PCR product was ligated to pBluescript SK (Stratagene) and transformed into E. coli DH5α by the SEM protocol (Inoue, H. et al., Gene. 96, 23 (1990)). Transformants were cultivated in an LB medium supplemented with 100 μg/ml of ampicillin. Subsequently, the plasmid was extracted by the alkaline lysis method (Sambrook, J. et al., Molecular Cloning, CSH Press, (1988)). Subcloning was verified by performing a PCR reaction with primer 3 and primer 4 using this plasmid DNA as a template. Partial nucleotide sequencing of the 320 bp fragment further confirmed that the derived amino acid sequence downstream of the primer 3 binding site matched with the experimentally determined N-terminal amino acid sequence. However, the 320 bp fragment contained only the N-terminal part of the third subunit gene.

Figure 9:
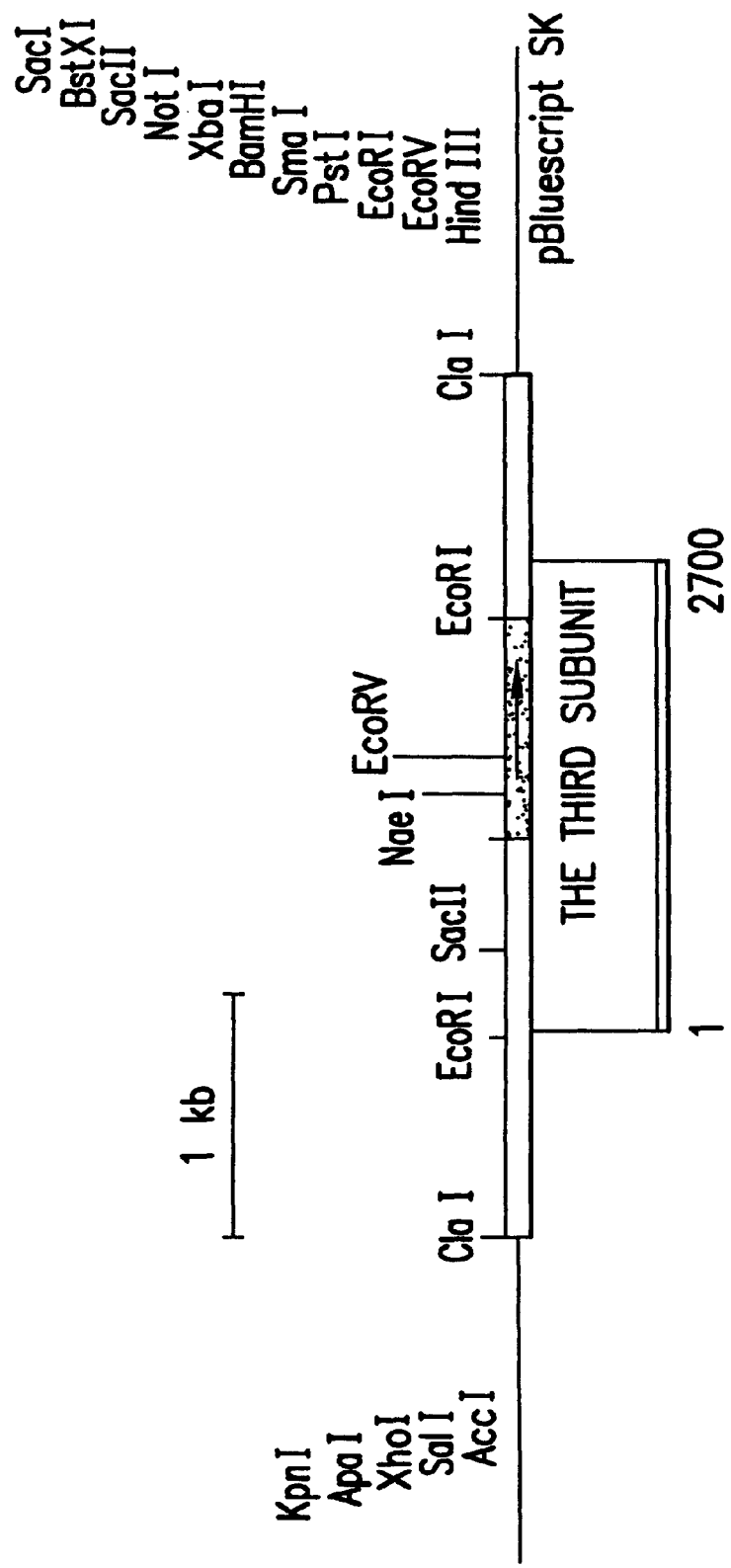
FIG. 9 presents a restriction enzyme map of ClaI-#69. The closed box represents the coding region of the third subunit gene of sorbitol dehydrogenase.

Example 8
Isolation of the third Subunit Gene Using 320 bp DNA Fragment as Probe The 320 bp DNA fragment isolated in (Example 7) was labeled with DIG Labeling and Detection Kit (*The DIG System User's Guide for Filter Hybridzation*. p6–9, Boehringer Mannheim (1993)). The genomic DNA isolated from G. suboxydans KCTC 2111 using the method of Takeda and Shimizu (Takeda and Shimizu, J. Ferm. Bioeng., 72, ((1991)) was digested with BamHI, ClaI, EcoRI, HindIII, PstI, or XhoI, electrophoresed in a 0.8% agarose gel and transferred to a nylon membrane (NYTRAN, Schleicher & Schuell) as described (Southern, E. M., J. Mol. Biol. 98,503 (1975)). The membrane was prehybridized in a hybridization oven (Hybaid) using a prehybridization solution (5×SSC, 1% (w/v) blocking reagent, 0.1% N-lauroylsarcosine, 0.2% SDS and 50% (v/v) formamide) at 42° C. for 2 hours. Then the membrane was hybridized using a hybridization solution (DIG-labeled probe diluted in the prehybridization solution) at 42° C. for 12 hours. Southern hybridization gave a strong discrete signal for each enzyme used. DNA corresponding to the positive signal at 4.5 kb ClaI was eluted and cloned into pBluescript SK to construct a mini-library. The mini-library was screened for the positive clone by repeating the Southern hybridization as described above. A clone which gave a positive signal was selected and designated ClaI-#69. FIG. 9 presents the restriction enzyme map of ClaI-#69.

Example 9
Nucleotide Sequence Analysis of the 4.5 kb ClaI Fragment Containing the Third Subunit The nucleotide sequence of the third subunit gene in the 4.5 kb ClaI-#69 clone was determined and analyzed. To facilitate the DNA sequencing, several overlapping restriction fragments were subcloned, and the nucleotide sequence of each clone determined. The nucleotide sequencing reaction was done by Dye Terminator Cycle Sequencing Ready Reaction Kit (Applied Biosystems), and the sequence was determined in an automatic DNA sequencer (Applied Biosystems, Model 373A).

FIG. 10 shows the nucleotide sequence of 2700 bp of the 4.5 kb ClaI fragment (SEQ ID NO:8). The sequenced DNA contains an open reading frame (ORF) of 921 nucleotides, which encodes the third subunit polypeptide. The third subunit gene is preceded by a potential Shine-Dalgarno sequence (AGG) positioned at 1,375–1,377 bp. The amino acid signal sequence of the third subunit polypeptide is positioned at 1,384–1,461 bp. The coding sequence of the mature part of the third subunit protein is positioned at 1,462–2,304 bp, encoding a 280 amino acid polypeptide whose derived N-terminal amino acid sequence was in perfect agreement with the 25 amino acid residues obtained by N-terminal amino sequence analysis. The calculated molecular weight of the mature protein of the third subunit is 29,552 Da, which was in good agreement with the experimental value of 29 kDa determined by SDS-PAGE.

---

What is claimed is:

1. An isolated nucleic acid molecule comprising a polynucleotide sequence at least 95% identical to the polynucleotide sequence of SEQ ID NO:1.

2. A vector comprising the nucleic acid molecule of claim 1.

3. A process for producing a vector in a host cell which comprises:
   (a) inserting the polynucleotide of claim 1 into a vector; and
   (b) selecting and propagating said vector in a host cell.

4. A host cell comprising the vector of claim 2.

5. An isolated nucleic acid molecule comprising a polynucleotide sequence at least 95% identical to the polynucleotide sequence of SEQ ID NO:2.

6. A vector comprising the nucleic acid molecule of claim 5.

7. A process for producing a vector in a host cell which comprises:
   (a) inserting the polynucleotide of claim 5 into a vector; and
   (b) selecting and propagating said vector in a host cell.

8. A host cell comprising the vector of claim 6.

9. An isolated nucleic acid molecule comprising a polynucleotide sequence at least 95% identical to the nucleic acid molecule sequence of SEQ ID NO:7.

10. A vector comprising the nucleic acid molecule of claim 9.

11. A process for producing a vector in a host cell which comprises:
    (a) inserting the polynucleotide of claim 9 into a vector; and
    (b) selecting and propagating said vector in a host cell.

12. A host cell comprising the vector of claim 10.

13. The nucleic acid molecule of claim 9 wherein said polynucleotide is at least 95% identical to the complete nucleotide sequence of the DNA clone contained in KCTC Deposit No. 0597BP.

14. An isolated nucleic acid molecule comprising a polynucleotide sequence selected from the group consisting of:
    (a) the nucleotide sequence encoding the full length subunit 1 protein of the sorbitol dehydrogenase (SDH)

of the invention from nucleotides 665–2,929 of SEQ ID NO: 7 which portion is identified as SEQ ID NO: 1;

(b) the nucleotide sequence encoding the mature form of the subunit 1 protein of the SDH of the invention from nucleotides 767–2,929 of SEQ ID NO: 7 which portion is identified as SEQ ID NO: 22;

(c) the nucleotide sequence encoding the full length subunit 2 protein of the SDH of the invention from nucleotides 2,964–4,400 of SEQ ID NO: 7 which portion is identified as SEQ ID NO: 2; and (d) the nucleotide sequence encoding the mature form of the subunit 2 protein of the SDH of the invention from nucleotides 3,072–4,400 of SEQ ID NO: 7 which portion is identified as SEQ ID NO: 23.

15. An isolated nucleic acid molecule comprising a polynucleotide sequence at la 95% identical to the polynucleotide sequence of SEQ ID NO:3.

16. A vector comprising the nucleic acid molicule of claim 15.

17. A process for producing a vector in a host cell which comprises:

(a) inserting the nucleic acid molecule of claim 15 into a vector; and (b) selecting and propagating said vector in a host cell.

18. A host cell comprising the vector of claim 16.

19. An isolated nucleic acid molecule comprising a polynucleotide sequence at least 95% identical to the nucleic acid molecule of SEQ ID NO:8.

20. A vector comprising the nucleic acid molecule of claim 19.

21. A process for producing a vector in a host cell which comprises:

(a) inserting the nucleic acid molecule of claim 19 into a vector; and (b) selecting and propagating said vector in a host cell.

22. A host cell comprising the vector of claim 20.

23. The nucleic acid molecule of claim 19 wherein said polynucleotide is at least 95% identical to the complete nucleotide sequence of the DNA clone contained in KCTC Deposit No. 0598BP.

24. A process for producing a polypeptide comprising:

(a) growing the host cell of claim 18;

(b) expressing the polypeptide of encoded by said vector in said host cell; and (c) isolating said polypeptide.

25. An isolated nucleic acid molecule comprising a polynucleotide sequence selected from the group consisting of:

(a) the nucleotide sequence encoding the full length SDH subunit 3 protein of the invention from nucleotides 1,384–2,304 of SEQ ID NO: 8 which portion is identified as SEQ ID NO: 3; and (b) the nucleotide sequence encoding the mature form of the SDH subunit 3 protein of the invention from nucleotides 1,462–2,304 of SEQ ID NO: 8 which portion is identified as SEQ ID NO: 24.

26. A process for the production of L-sorbose from D-sorbitol comprising:

(a) propagating a host cell in an appropriate culture media, said host cell being transformed with:

(i) an isolated polynucleotide comprising a polynucleotide sequence at least 95% identical to the polynucleotide sequence of SEQ ID NO: 1;

(ii) an isolated polynucleotide comprising a polynucleotide sequence at least 95% identical to the polynucleotide sequence of SEQ ID NO: 2; and (iii) an isolated polynucleotide comprising a polynucleotide sequence at least 95% identical to the polynucleotide sequence of SEQ ID NO: 3; and (b) recovering and separating said L-sorbose from said culture media.

27. A process for the production of L-sorbose from D-sorbitol comprising:

(a) propagating a Gluconobacter host cell in an appropriate culture media, said host cell being transformed with at least one isolated polynucleotide selected from the group consisting of:

(i) an isolated polynucleotide comprising a polynucleotide sequence at least 95% identical to the polynucleotide sequence of SEQ ID NO: 1;

(ii) an isolated polynucleotide comprising a polynucleotide sequence at least 95% identical to the polynucleotide sequence of SEQ ID NO: 2; and (iii) an isolated polynucleotide comprising a polynucleotide sequence at least 95% identical to the polynucleotide sequence of SEQ ID NO: 3; and (b) recovering and separating said L-sorbose from said culture media.

28. A process for the production of 2-keto-L-gulonic acid comprising:

(a) propagating a host cell in an appropriate culture media, said host cell being transformed with:

(i) an isolated polynucleotide comprising a polynucleotide sequence at least 95% identical to the polynucleotide sequence of SEQ ID NO: 1;

(ii) an isolated polynucleotide comprising a polynucleotide sequence at least 95% identical to the polynucleotide sequence of SEQ ID NO: 2; and (iii) an isolated polynucleotide comprising a polynucleotide sequence at least 95% identical to the polynucleotide sequence of SEQ ID NO: 3; and (b) recovering and separating said 2-keto-L-gulonic acid from said culture media.

29. A process for the production of 2-keto-L-gulonic acid comprising:

(a) propagating a Gluconobacter host cell in an appropriate culture media, said host cell being transformed with at least one isolated polynucleotide selected from the group consisting of:

(i) an isolated polynucleotide comprising a polynucleotide sequence at least 95% identical to the polynucleotide sequence of SEQ ID NO: 1;

(ii) an isolated polynucleotide comprising a polynucleotide sequence at least 95% identical to the polynucleotide sequence of SEQ ID NO: 2; and (iii) an isolated polynucleotide comprising a polynucleotide sequence at least 95% identical to the polynucleotide sequence of SEQ ID NO: 3; and (b) recovering and separating said 2-keto-L-gulonic acid from said culture media.

* * * * *

UNITED STATES PATENT AND TRADEMARK OFFICE
CERTIFICATE OF CORRECTION

PATENT NO. : 6,204,040 B1
DATED : March 20, 2001
INVENTOR(S) : Choi et al.

It is certified that error appears in the above-identified patent and that said Letters Patent is hereby corrected as shown below:

Column 1,
Line 38, please delete "2KLG" and insert therein -- 2-KLG --.

Column 2,
Line 6, please delete "2KLG" and insert therein -- 2KLG --.

Column 6,
Line 5, please delete "ofthe" and insert therein -- of the --.
Line 25, please delete "ofthe" and insert therein -- of the --.
Line 50, please delete "ofthe" and insert therein -- of the --.

Column 8,
Line 1, please delete "ofthe" and insert therein -- of the --.
Line 55, please delete "ofthe" and insert therein -- of the --.

Column 9,
Line 28, please delete "ofthe" and insert therein -- of the --.
Line 55, please delete "fragments of the invention may single stranded" and insert therein -- fragments of the invention may be single stranded --.
Line 59, please delete "ofthe" and insert therein -- of the --.

Column 10,
Line 18, please delete "SEQ IDNO:7" and insert therein -- SEQ ID NO:7 --.
Line 25, please delete "withthe" and insert therein -- with the --.
Line 29, please delete "ofthe" and insert therein -- of the --.
Line 40, please delete "ofSEQ ID NO: 7" and insert therein -- of SEQ ID NO: 7 --.
Line 40, please delete "dentified" and insert therein -- identified --.

Column 11,
Line 61, please delete "ofthe" and insert therein -- of the --.

Column 12,
Line 43, please delete "Corynebacterim" and insert therein -- Corynebacterium --.
Line 65, please delete "ofthe" and insert therein -- of the --.

Column 17,
Line 4, after "fermentation" please insert a comma to read -- In a batch fermentation, --.

UNITED STATES PATENT AND TRADEMARK OFFICE
CERTIFICATE OF CORRECTION

PATENT NO. : 6,204,040
DATED : March 20, 2001
INVENTOR(S) : Choi et al.

It is certified that error appears in the above-identified patent and that said Letters Patent is hereby corrected as shown below:

Column 18,
Line 16, please delete "2-KGL" and insert therein -- 2-KLG --.
Line 29, please deleta "SDHfrom" and insert therein --SDH from --.

Column 22,
Line 5, please delete "was" and insert therein -- were --.
Line 23, please delete "DH5a" and insert therein -- DH5$a$ --.
Line 50, please delete "QLAEX II" and insert therein -- QIAEX II --.

Column 23,
Line 17, before "Southern" please delete the comma to read -- again by Southern hybridization --.
Line 45, please delete "simpler" and insert therein -- more simple --.

Column 24,
Line 4, please delete "Shine-Dalgamo" and insert therein -- Shine Delgarno --.
Line 31, before "cofactor" please insert -- a --.

Column 25,
Line 12, before "third" please insert -- the --.

Claim 15, column 103
Line 17, please delete "a polynucleotide sequence at la 95% identical" and insert therein -- a polynucleotide sequence at least 95% identical --.

UNITED STATES PATENT AND TRADEMARK OFFICE
CERTIFICATE OF CORRECTION

PATENT NO. : 6,204,040
DATED : March 20, 2001
INVENTOR(S) : Choi et al.

It is certified that error appears in the above-identified patent and that said Letters Patent is hereby corrected as shown below:

Claim 16, column 103,
Line 19, please delete "molicule" and insert therein -- molecule --.

Signed and Sealed this

Twenty-seventh Day of November, 2001

Attest:

*Nicholas P. Godici*

NICHOLAS P. GODICI
*Attesting Officer*     *Acting Director of the United States Patent and Trademark Office*